(12) United States Patent
Li et al.

(10) Patent No.: US 7,501,446 B2
(45) Date of Patent: Mar. 10, 2009

(54) PRENYLATION INHIBITORS AND METHODS OF THEIR SYNTHESIS AND USE

(75) Inventors: Francine Feirong Li, Raleigh, NC (US);
Kenneth S. Rehder, Durham, NC (US);
Michael Gordon Campbell, Sagamore Hills, OH (US); Celeste Patrice Viscardi, Raleigh, NC (US); Jon-Paul Strachan, Durham, NC (US);
Zhengming Guo, Raleigh, NC (US)

(73) Assignee: PPD Discovery, Inc., Morrisville, NC (US)

( * ) Notice: Subject to any disclaimer, the term of this patent is extended or adjusted under 35 U.S.C. 154(b) by 0 days.

(21) Appl. No.: 11/618,932

(22) Filed: Jan. 1, 2007

(65) Prior Publication Data

US 2007/0149549 A1      Jun. 28, 2007

Related U.S. Application Data

(60) Division of application No. 10/636,327, filed on Aug. 6, 2003, now Pat. No. 7,166,619, which is a continuation-in-part of application No. 10/336,285, filed on Jan. 3, 2003, now Pat. No. 6,649,638, which is a continuation-in-part of application No. 10/219,628, filed on Aug. 14, 2002, now abandoned.

(51) Int. Cl.
*A61K 31/4439* (2006.01)
*C07D 401/14* (2006.01)

(52) U.S. Cl. .................................... 514/341; 546/275.4

(58) Field of Classification Search .............. 546/275.4; 514/341
See application file for complete search history.

(56) References Cited

U.S. PATENT DOCUMENTS

| | | | |
|---|---|---|---|
| 3,985,376 A | 10/1976 | Baumann et al. | |
| 4,826,868 A | 5/1989 | Wachter et al. | |
| 5,134,142 A | 7/1992 | Matsuo et al. | |
| 5,164,381 A | 11/1992 | Wachter et al. | |
| 5,420,141 A | 5/1995 | Boigegrain et al. | |
| 5,633,388 A | 5/1997 | Diana et al. | |
| 5,840,653 A | 11/1998 | Ganzer et al. | |
| 6,191,147 B1 | 2/2001 | Brown et al. | |
| 6,511,994 B2 | 1/2003 | Kim et al. | |
| 6,914,069 B2 * | 7/2005 | Shroff et al. | ................ 514/341 |
| 2002/0193407 A1 | 12/2002 | Kim et al. | |

FOREIGN PATENT DOCUMENTS

| | | |
|---|---|---|
| EP | 679644 | 11/1995 |
| WO | 9852940 | 11/1998 |
| WO | 03/030898 | 4/2003 |

OTHER PUBLICATIONS

Marzinzik et al., "Key Intermediates in Combinatorial Chemistry: Access to Various Heterocycles from α,β-Unsaturated Ketones on the Solid Phase", J. Org. Chem., 1998, vol. 63, pp. 723-727.
Marzinzik et al., "Solid Support Synthesis of Highly Functionalized Pyrazoles and Isoxazoles; Scaffolds for Molecular Diversity", Tetrahedron Letters, 1996, vol. 37, No. 7, pp. 1003-1006.
CA 138:39281, Kim et al. 2002.
Marzinzik et al., Key Intermediates in Combinatorial Chemistry: Access to Various Heterocycles from alpha,beta-Unsaturated Ketones on the Solid Phase, J. Org. Chem. 63:723-727 (1998).
Marzinzik et al., Solid Support Synthesis of Highly Functionalized Pyrazoles and Isoxazoles; Scaffolds for Molecular Diversity, Tetrhedron Letters 37(7):1003-06 (1996).
Kim et al., Chemical Abstracts 138:39281 (2000).

* cited by examiner

*Primary Examiner*—Patricia L Morris
(74) *Attorney, Agent, or Firm*—Sheridan Ross P.C.

(57) ABSTRACT

The present invention is directed to compounds useful in the treatment of diseases associated with prenylation of proteins and pharmaceutically acceptable salts thereof, to pharmaceutical compositions comprising same, and to methods for inhibiting protein prenylation in an organism using the same.

2 Claims, 17 Drawing Sheets

PRENYLATION INHIBITORS AND METHODS OF THEIR SYNTHESIS AND USE

CROSS REFERENCE TO RELATED APPLICATIONS

This application is a divisional of U.S. patent application Ser. No. 10/636,327, filed Aug. 6, 2003, now U.S. Pat. No. 7,166,619, which is a continuation-in-part of U.S. patent application Ser. No. 10/336,285, now U.S. Pat. No. 6,649,638, filed Jan. 3, 2003, which is a continuation-in-part of U.S. patent application Ser. No. 10/219,628, filed Aug. 14, 2002, now abandoned. Each of these priority documents is incorporated herein, in its entirety, by reference.

FIELD OF THE INVENTION

This present invention relates to a class of novel compounds useful in the treatment of diseases associated with the prenylation of proteins.

BACKGROUND OF THE INVENTION

The mammalian Ras proteins are a family of guanosine triphosphate (GTP) binding and hydrolyzing proteins that regulate cell growth and differentiation. Their overproduction or mutation can lead to uncontrolled cell growth, and has been implicated as a cause or aggravating factor in a variety of diseases including cancer, restenosis, psoriasis, endometriosis, atherosclerosis, viral or yeast infection, and corneal neovascularization.

Ras proteins share characteristic C-terminal sequences termed the CAAX motif, wherein C is Cys, A is an amino acid, usually an aliphatic amino acid, and X is an aliphatic amino acid or other type of amino acid. The biological activity of the proteins is dependent upon the post-translational modification of these sequences by isoprenoid lipids. For proteins having a C-terminal CAAX sequence, this modification, which is called prenylation, occurs in at least three steps: the addition of either a 15 carbon (farnesyl) or 20 carbon (geranylgeranyl) isoprenoid to the Cys residue, the proteolytic cleavage of the last three amino acids from the C-terminus, and the methylation of the new C-terminal carboxylate. Zhang and Casey, $Ann.\ Rev.\ Biochem.$ 1996, 65, 241-269. The prenylation of some proteins may include a fourth step; the palmitoylation of one or two Cys residues N-terminal to the farnesylated Cys.

Ras-like proteins terminating with XXCC or XCXC motifs can also be prenylated and are modified by geranylgeranylation on the Cys residues. These proteins do not require an endoproteolytic processing step. While some mammalian cell proteins terminating in XCXC are carboxymethylated, it is not clear whether carboxymethylation follows prenylation of proteins terminating with XXCC motifs. Clarke, $Ann.\ Rev.\ Biochem.$, 1992, 61, 355-386. For all Ras-like proteins, however, addition of the isoprenoid is the first step of prenylation, and is required for the subsequent steps. Cox and Der, $Critical\ Rev.\ Oncogenesis,$ 1992, 3, 365-400; and Ashby et al., $Curr.\ Opinion\ Lipidology,$ 1998, 9, 99-102.

Three enzymes have been found to catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are present in both yeast and mammalian cells. Schafer and Rine, $Annu.\ Rev.\ Genet.,$ 1992, 30, 209-237. U.S. Pat. No. 5,578,477 discloses a method of purifying FPTase using recombinant technology and yeast host cells. Such techniques are useful in the elucidation of the enzyme structures.

FPTase and GGPTase-I are $\alpha/\beta$ heterodimeric enzymes that share a common $\alpha$ subunit; the $\beta$ subunits are distinct but share approximately 30% amino acid identity. Brown and Goldstein, $Nature,$ 1993, 366, 14-15; Zhang et al., $J.\ Biol.\ Chem.,$ 1994, 269, 3175-3180. GGPTase II has different $\alpha$ and $\beta$ subunits, and complexes with a third component (REP, Rab Escort Protein) that presents the protein substrate to the $\alpha/\beta$ catalytic subunits. GGPTase proteins, and the nucleic acid sequence encoding them, are disclosed by U.S. Pat. No. 5,789,558 and WO 95/20651. U.S. Pat. No. 5,141,851 discloses the structure of a FPTase protein.

Each of these enzymes selectively uses farnesyl diphosphate or geranylgeranyl diphosphate as the isoprenoid donor, and selectively recognizes the protein substrate. FPTase farnesylates CAAX-containing proteins that end with Ser, Met, Cys, Gln or Ala. GGPTase-I geranylgeranylates CAAX-containing proteins that end with Leu or Phe. For FPTase and GGPTase-I, CAAX tetrapeptides comprise the minimum region required for interaction of the protein substrate with the enzyme. GGPTase-II modifies XXCC and XCXC proteins, but its interaction with protein substrates is more complex, requiring protein sequences in addition to the C-terminal amino acids for recognition. Enzymological characterization of FPTase, GGPTase-I and GGPTase-II has demonstrated that it is possible to selectively inhibit only one of these enzymes. Moores e al., $J.\ Biol\ Chem.,$ 1991, 266, 17438.

GGPTase-I transfers a geranylgeranyl group from the prenyl donor geranylgeranyl diphosphate to the cysteine residue of substrate CAAX protein. Clarke, $Annu.\ Rev.\ Biochem.,$ 1992, 61, 355-386; Newman and Magee, $Biochim.\ Biophys.\ Acta,$ 1993, 1155, 79-96. Known targets of GGPTase-I include the gamma subunits of brain heterotrimeric G proteins and Ras-related small GTP-binding proteins such as RhoA, RhoB, RhoC, CDC42Hs, Rac1, Rac2, Rap1A and Rap1B. The proteins RhoA, RhoB, RhoC, Rac1, Rac2 and CDC42Hs have roles in the regulation of cell shape. Ridley and Hall, $Cell,$ 1992, 70, 389-399; Ridley et al, $Cell,$ 1992, 70, 401-410; Bokoch and Der, $FASEB\ J.,$ 1993, 7, 750-759. Rac and Rap proteins play roles in neutrophil activation.

It has been found that the ability of Ras proteins to affect cell shape is dependant upon Rho and Rac protein function. See, e.g., Mackey and Hall, $J.\ Biol.\ Chem.,$ 1998, 273, 20688-20695. It thus follows that because Rho and Rac proteins require geranylgeranylation for function, an inhibitor of GGPTase-I would block the functions of these proteins, and may be useful as, for example, an anticancer agent. This notion is supported by recently reported research.

For example, GGPTase-I inhibitors can arrest human tumor cells that lack p53 in G0/G1, and induce the accumulation of $p21^{WAP}$. This suggests that these inhibitors could be used to restore growth arrest in cells lacking functional p53. Vogt et al., $J.\ Biol.\ Chem.,$ 1997, 272, 27224-27229. Noteworthy in this regard are reports indicating that K-Ras, the form of Ras gene most associated with human cancers, can be modified by GGPTase-I in cells where FPTase is inhibited. Whyte et al., $J.\ Biol.\ Chem.,$ 1997, 272, 14459-14464. Since geranylgeranylated Ras has been reported to be as efficient as the farnesylated form in cell transformation studies, K-Ras cancers could be treated with GGPTase-I inhibitors. Lerner et al., $J.\ Biol.\ Chem.,$ 1995, 270, 26770-26773.

In addition to cancer, there are other pathological conditions for which GGPTase inhibitors may be used as intervention agents. These include, for example, the intimal hyperplasia associated with restenosis and atherosclerosis. Pulmonary artery smooth muscle cells seem particularly sensitive to inhibition of GGPTase-I, and treatment of such cells with a GGPTase inhibitor resulted in a superinduction of their inducible nitric-oxide synthase (NOS-2) by interleukin-1β. Finder et al., *J. Biol. Chem.*, 1997, 272, 13484-13488.

GGPTase inhibitors may also be used as anti-fungal agents. In *S. cerievisiae* and *Candida albicans*, and apparently most other fungi, cell wall biosynthesis is controlled by a Rho-type protein that is modified by the fungal GGPTase-I. Qadota et al., *Science*, 1996, 272, 279-281. Selective inhibition of the fungal enzyme would diminish cell wall integrity, and thus be lethal to fungal cells.

Numerous other prenylation inhibitors have been studied. Some examples of these are disclosed by U.S. Pat. Nos. 5,420,245; 5,574,025; 5,523,430; 5,602,098; 5,631,401; 5,705,686; 5,238,922; 5,470,832; and 6,191,147; and by European Application Nos. 856,315 and 537,008. The effectiveness and specificity of these inhibitors vary widely, as do their chemical structures, and many of them are difficult to synthesize and purify.

Therefore, there is a need for new, more effective prenyl-protein transferase inhibitors.

SUMMARY OF THE INVENTION

The present invention provides a group of structurally-related compounds disclosed below that are effective as inhibitors of protein prenylation.

The present invention also provides a composition comprising a compound of the present invention, or a pharmaceutically-acceptable salt thereof, and a pharmaceutically-acceptable carrier.

The present invention also provides a method for inhibiting protein prenylation comprising contacting an isoprenoid transferase with a compound of the present invention or a pharmaceutically-acceptable salt thereof. As used herein, an "isoprenoid transferase" refers to any enzyme capable of transferring an isoprenoid group, for example, farnesyl or geranylgeranyl, to a protein, e.g., Ras or Ras-like proteins. Such isoprenoid transferases include FPTase, GGPTase I and GGPTase II. Unless the context requires otherwise, the term "contacting" refers to providing conditions to bring the compound into proximity to an isoprenoid transferase to allow for inhibition of activity of the isoprenoid transferase. For example, contacting a compound of the present invention with an isoprenoid transferase can be accomplished by administering the compound to an organism, or by isolating cells, e.g., cells in bone marrow, and admixing the cells with the compound under conditions sufficient for the compound to diffuse into or be actively taken up by the cells, in vitro or ex vivo, into the cell interior. When ex vivo administration of the compound is used, for example, in treating leukemia, the treated cells can then be reinfused into the organism from which they were taken.

Such method for inhibiting protein prenylation can be used, for example, in prevention and/or treatment of a disease or condition in a plant or animal that is caused, aggravated or prolonged by Ras or Ras-like protein prenylation. In animals, such diseases include, but are not limited to, cancer, restenosis, psoriasis, endometriosis, atherosclerosis, ischemia, myocardial ischemic disorders such as myocardial infarction, high serum cholesterol levels, viral infection, fungal infections, yeast infections, bacteria and protozoa infections, and disorders related to abnormal angiogenesis including, but not limited to, corneal neovascularization. In plants, such diseases include yeast and viral infections.

DETAILED DESCRIPTION OF THE INVENTION

Figure 1:
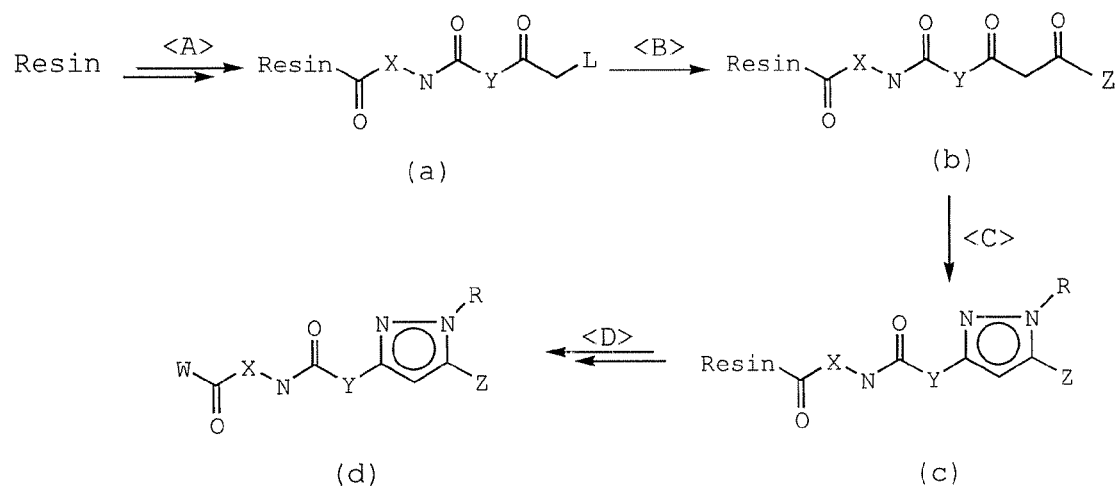
FIG. 1 illustrates a general synthetic approach for the production of prenylation inhibitors of the present invention having a central pyrazole ring.

As used herein, the term "organism" includes plants and animals. Exemplary animals include mammals, fish, birds, insects, and arachnids. Humans can be treated with the compounds of the invention arid fall within the mammal subcategory.

As used herein, the term "CAAX" means a C-terminal peptide sequence wherein C is Cys, A is an amino acid, usually an aliphatic amino acid, and X is another amino acid, usually Leu or Phe.

As used herein, the term "CAAX protein" means a protein comprising a CAAX sequence.

As used herein, the term "XXCC" means a C-terminal peptide sequence wherein C is Cys and X is another amino acid, usually Leu or Phe.

As used herein, the term "XXCC protein" means a protein comprising a XXCC sequence.

As used herein, the term "XCXC" means a C-terminal peptide sequence wherein C is Cys and X is another amino acid, usually Leu or Phe.

As used herein, the term "XCXC protein" means a protein comprising a XCXC sequence.

As used herein, the term "Ras or Ras-like protein" encompasses Ras proteins, brain heterotrimeric G proteins, and other GTP-binding proteins such as members of the Rho, Rac and Rab family including, but not limited to, RhoA, RhoB, RhoC, CDC42Hs, Rac1, Rac2, Rap1A and Rap1B. A Ras or Ras-like protein may be a CAAX, XXCC, or XCXC protein. The term "Ras or Ras-like protein" as used herein also encompasses Rheb, inositol-1,4,5,triphosphate-5-phosphatase, and cyclic nucleotide phosphodiesterase and isoforms thereof, including nuclear lamin A and B, fungal mating factors, and several proteins in visual signal transduction.

As used herein, the term "Ras or Ras-like protein prenylation" means the prenylation of a Ras or Ras-like protein that is catalyzed or caused by GGPTase I, GGPTase II, or FPTase.

As used herein, the term "prenylation inhibitor" means a compound or mixture of compounds that inhibits, restrains, retards, blocks or otherwise affects protein prenylation, preferably Ras or Ras-like protein prenylation. A prenylation inhibitor may inhibit, restrain, retard, or otherwise affect the activity of GGPTase I, GGPTase II, and/or FPTase.

As used herein, the term "a pharmaceutically-acceptable salt thereof" refers to salts prepared from pharmaceutically-acceptable nontoxic acids or bases including inorganic acids and bases and organic acids and bases. Examples of such inorganic acids are hydrochloric, hydrobromic, hydriodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, tartaric, citric and galacturonic. Examples of suitable inorganic bases include metallic salts made from aluminum, calcium, lithium, magnesium, potassium, sodium, and zinc. Appropriate organic bases may be selected, for example, from N,N-dibenzylethylenediamine, chlorprocaine, choline, diethanolamine, ethylenediamine, meglumaine (N-methylglucamine), lysine and procaine. Preferred salts of the compounds of this invention are TFA and acetate salts.

The phrase "therapeutically effective amount of prenylation inhibitor" as used herein means that amount of prenylation inhibitor which alone or in combination with other drugs provides a therapeutic benefit in the treatment, management, or prevention of conditions in a plant or animal that are caused, aggravated or prolonged by Ras or Ras-like protein prenylation. Such conditions include, but are not limited to, cancer, restenosis, psoriasis, endometriosis, atherosclerosis, ischemia, myocardial ischemic disorders such as myocardial infarction, high serum cholesterol levels, viral infection, fungal infections, yeast infections, bacteria and protozoa infections, and undesired angiogenesis, abnormal angiogenesis or abnormal proliferation such as, but not limited to, corneal neovascularization. Other conditions include abnormal bone resorption and conditions related thereto.

"Alkyl" groups according to the present invention are aliphatic hydrocarbons which can be straight, branched or cyclic. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, propyl, i-propyl, n-butyl, t-butyl, bicycloheptane (norbornane), cyclobutane, dimethyl-cyclobutane, cyclopentane, cyclohexane, fluoromethyl, difluoromethyl, trifluoromethyl, chloromethyl, trichloromethyl, and pentafluoroethyl. Preferably, alkyl groups have from about 1 to about 20 carbon atom chains, more preferably from about 1 to about 10 carbon atoms, still more preferably from about 1 to about 6 carbon atoms, and most preferably from about 1 to about 4 carbon atoms.

"Aryl" groups are monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl.

"Heteroaryl" refers to monocyclic or bicyclic aromatic ring having at least one heteroatom selected from nitrogen, sulfur, phosphorus and oxygen. Preferred heteroaryls are 5- and 6-membered aromatic rings which contain from about 1 to about 3 heteroatoms. Examples of heteroaryl groups include, but are not limited to, pyridinyl, imidazolyl, pyrimidinyl, pyrazolyl, (1,2,3)- and (1,2,4)-triazolyl, pyrazinyl, tetrazolyl, furyl, thienyl, isoxazolyl, oxazolyl, pyrrolyl, thiazolyl, pyrrole, thiophenyl, furanyl, pyridazinyl, isothiazolyl, and S-triazinyl.

"N-heteroaryl" refers to monocyclic or bicyclic aromatic ring having at least one nitrogen atom in the aromatic ring moiety. Exemplary N-heteroaryls include, but are not limited to, pyridinyl, imidazolyl, pyrrimidinyl, pyrazolyl, (1,2,3)- and (1,2,4)-triazolyl, pyrazinyl, tetrazolyl, isoxazolyl, oxazolyl, pyrrolyl, pyrrole, pyridazinyl, and isothiazolyl. Preferably, N-heteroaryl is pyridinyl. More preferably, N-heteroaryl is pyridin-3-yl.

The term "aryl containing at least one nitrogen substituent" refers to an aryl moiety having a substituent such as an amino, including mono-, di-, and tri-alkyl amino groups; amido; or $C_1$-$C_4$ alkyl groups having an amino or an amido substituent. Preferably, an "aryl containing at least one nitrogen substituent" is an aryl moiety having amino, amido or $C_1$-$C_2$ alkyl having an amino or amido substituent; more preferably amino, amido or $C_1$ alkyl having an amino or amido substituent; still more preferably an amino or amido substituent; and most preferably an amino substituent.

The term "peptoids" or "polypeptoids" refers to poly-(N-substituted glycine) chains. These peptidomimetic molecules have a number of particular advantages as discussed below. For example, peptoids are synthetic and non-natural polymers with controlled sequences and lengths, that may be made by automated solid-phase organic synthesis to include a wide variety of side-chains having different chemical functions. Peptoids have a number of notable structural features in comparison to peptides. For example, peptoids lack amide protons; thus, no intrachain hydrogen-bond network along the polymer backbone is possible, unless hydrogen-bond donating side-chains are put in the peptoid chain. In addition, whereas the side-chain ("R") groups on biosynthetically produced peptides must be chosen from among the 20 amino acids, peptoids can include a wide variety of different, non-natural side-chains because in peptoid synthesis the R group can be introduced as a primary amine. This is in contrast to synthetic peptides for which the incorporation of non-natural side-chains requires the use of non-natural a-protected amino acids. Polypeptoid (or peptoids) can be synthesized in a sequence-specific fashion using an automated solid-phase protocol, e.g., the sub-monomer synthetic route. See, for example, Wallace et al., *Adv. Amino Acid Mimetics Peptidomimetics*, 1999, 2, 1-51 and references cited therein, all of which are incorporated herein in their entirety by this reference.

The flexibility of sub-monomer synthesis allows attachment of side-chains that satisfy the requirements of specific needs, e.g., hydrophilicity or hydrophobicity. Another advantage of the peptoid synthetic protocol is that it allows easy production of peptoid-peptide chimerae. In a single automated solid-phase protocol, one can alternate the addition of peptoid monomers with the addition of (α-Fmoc-protected peptide monomers, the latter added by standard Fmoc coupling protocols employing activating agents such as pyBrop or pyBop (i.e., 1H-benzotriazol-1-yloxy-tris(pyrrolidino) phosphonium hexafluorophosphate).

Unless otherwise stated, the term "aromatic group" refers to aryl and heteroaryl groups.

The terms "substituted," "substituted derivative" and "derivative" when used to describe a chemical moiety means that at least one hydrogen bound to the unsubstituted chemical moiety is replaced with a different atom or a chemical moiety. Examples of substituents include, but are not limited to, alkyl, halogen, nitro, cyano, heterocycle, aryl, heteroaryl, amino, amide, hydroxy, ester, ether, carboxylic acid, thiol, thioester, thioether, sulfoxide, sulfone, carbamate, peptidyl, $PO_3H_2$, and mixtures thereof.

The term "cancer" encompasses, but is not limited to, myeloid leukemia; malignant lymphoma; lymphocytic leukemia; myeloproliferative diseases; solid tumors including benign tumors, adenocarcinomas, and sarcomas; and blood-borne tumors. The term "cancer" as used herein includes, but is not limited to, cancers of the cervix, breast, bladder, colon, stomach, prostate, larynx, endometrium, ovary, oral cavity, kidney, testis and lung.

The terms "compound of the present invention," "compound of this invention," "compound of the invention," "prenylation inhibitor of the present invention," "prenylation inhibitor of this invention," and "prenylation inhibitor of the invention" are used interchangeably to refer to the compounds and complexes disclosed herein, and to their pharmaceutically acceptable salts, solvates, hydrates, polymorphs, and clatherates thereof, and to crystalline and non-crystalline forms thereof.

The present invention is based upon the discovery that certain pyrazole-based compounds are potent prenylation inhibitors. These compounds inhibit the activity of one or more of the following: GGPTase I, GGPTase II, and FPTase. In one particular embodiment, the compounds of the present invention, under the assay conditions disclosed in the Examples section, have an $IC_{50}$ value for GGPTase I of about 25 μM or less, more preferably about 10 μM or less, more preferably about 5 μM or less, more preferably about 10 nanomolar or less and most preferably between about 1 nanomolar and about 2 nanomolar.

This invention is further based upon the recognition that protein prenylation, in particular prenylation of CAAX, XXCC and/or XCXC proteins, is associated with a variety of diseases and/or conditions in plants and animals. In animals, such diseases include, but are not limited to, cancer, restenosis, psoriasis, endometriosis, atherosclerosis, ischemia, myocardial ischemic disorders such as myocardial infarction, high serum cholesterol levels, viral infection, fungal infections, yeast infections, bacteria and protozoa infections, proliferative disorders, and disorders related to abnormal angiogenesis including, but not limited to, corneal neovascularization. In plants, such diseases include yeast and viral infections.

Compounds of the present invention useful for inhibition of protein prenylation are shown below. It should be recognized that reference to a compound, identification of a general chemical structure or a specific compound below and in the claims refers to the compound itself, as well as pharmaceutically acceptable salts thereof. Moreover, to the extent the structure of elements in the definitions of the R groups permits more than one site of attachment to the main structure, preferred sites of attachment for such elements are shown below in the exemplary specific structures an/or are dictated by the various methods of synthesis shown below.

One embodiment of the present invention includes compounds that may be used for inhibiting protein prenylation having the general structure of Formula I:

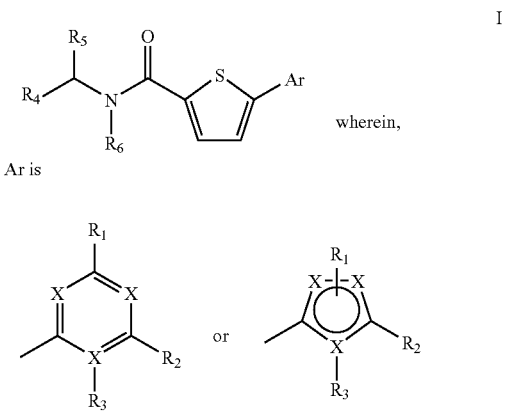

wherein,

Ar is

Each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine,$CH_2COOH$, $N(CH_3)_2$, $CH_2CH_2SCH_3$ or $CH_2$-piperidinyl;

$R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is absent, H, $NH_2$, $CON(CH_3)_2$, $CO_2H$, CN, $CH_2OH$, $CONH_2$, $CSNH_2$, CONHOH, $C(NH)NH_2$, $CONHNH_2$, $CONHCH_3$, $CH_2OCH_3$, CONH-cyclohexyl, $CO_2CH_3$,

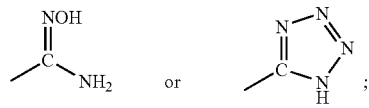

$R_5$ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2$-imidazole, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-indole, $CH_2$-thiophene, $CH_2$-cyclohexane, 4-chlorobenzyl, phenyl, 2-hydroxybenzyl, 4-tertbutoxybenzyl, $CH_2$-benzylimidazole, 4-aminobenzyl, $CH_2$-pryid-3-yl, $CH_2$-pryid-2-yl, $CH_2OH$, $(CH_2)_3NHC(NH)NH_2$ or $CH_2CH(CH_3)_2$; and, $R_6$ is H, methyl, ethyl, propyl, isopropyl, $CH_2CO_2H$, $CH_2CO_2Et$, benzyl, or $CH_2$-(2-methoxynaphthyl); or, $R_5$ and $R_6$ together form:

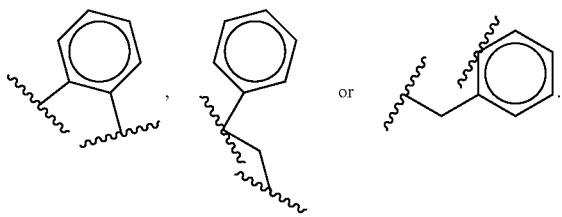

Another embodiment of the present invention includes compounds that may be used for inhibiting protein prenylation having the general structure of Formula II:

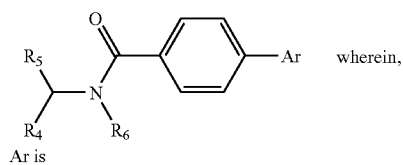 II wherein, Ar is

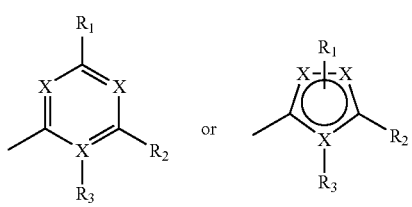

Each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine,$CH_2COOH$, $N(CH_3)_2$, $CH_2CH_2SCH_3$ or $CH_2$-piperidinyl;

$R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is absent, H, $NH_2$, $CON(CH_3)_2$, $CO_2H$, CN, $CH_2OH$, $CONH_2$, $CSNH_2$, CONHOH, $C(NH)NH_2$, $CONHNH_2$, $CONHCH_3$, $CH_2OCH_3$, CONH-cyclohexyl, $CO_2CH_3$,

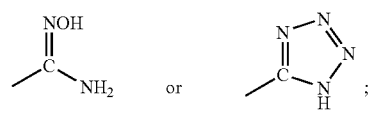

$R_5$ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2$-imidazole, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-indole, $CH_2$-thiophene, $CH_2$-cyclohexane, 4-chlorobenzyl, phenyl, 2-hydroxybenzyl, 4-tertbutoxybenzyl, $CH_2$-benzylimidazole, 4-aminobenzyl, $CH_2$-pryid-3-yl, $CH_2$-pryid-2-yl, $CH_2OH$, $(CH_2)_3NHC(NH)NH_2$ or $CH_2CH(CH_3)_2$; and, $R_6$ is H, methyl, ethyl, propyl, isopropyl, $CH_2CO_2H$, $CH_2CO_2Et$, benzyl, or $CH_2$-(2-methoxynaphthyl); or, $R_5$ and $R_6$ together form:

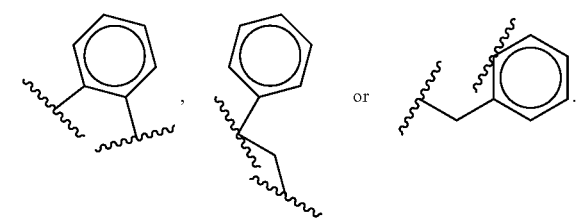

Another embodiment of the present invention includes compounds that may be used for inhibiting protein prenylation having the general structure of Formula III:

wherein

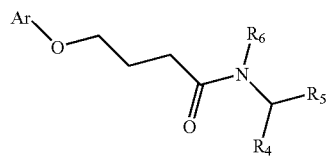

III

Ar is

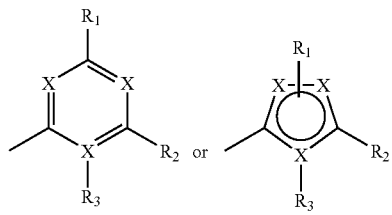

Each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine, $CH_2COOH$, $N(CH_3)_2$, $CH_2CH_2SCH_3$ or $CH_2$-piperidinyl;

$R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is absent, H, $NH_2$, $CON(CH_3)_2$, $CO_2H$, CN, $CH_2OH$, $CONH_2$, $CSNH_2$, CONHOH, $C(NH)NH_2$, $CONHNH_2$, $CONHCH_3$, $CH_2OCH_3$, CONH-cyclohexyl, $CO_2CH_3$,

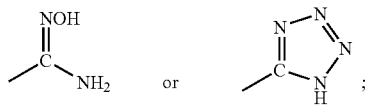

$R_5$ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2$-imidazole, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-indole, $CH_2$-thiophene, $CH_2$-cyclohexane, 4-chlorobenzyl, phenyl, 2-hydroxybenzyl, 4-tertbutoxybenzyl, $CH_2$-benzylimidazole, 4-aminobenzyl, $CH_2$-pryid-3-yl, $CH_2$-pryid-2-yl, $CH_2OH$, $(CH_2)_3NHC(NH)NH_2$ or $CH_2CH(CH_3)_2$; and, $R_6$ is H, methyl, ethyl, propyl, isopropyl, $CH_2CO_2H$, $CH_2CO_2Et$, benzyl, or $CH_2$-(2-methoxynaphthyl); or, $R_5$ and $R_6$ together form:

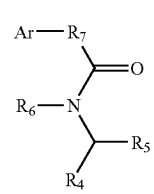

Another embodiment of the present invention includes compounds that may be used for inhibiting protein prenylation having the general structure of Formula IV:

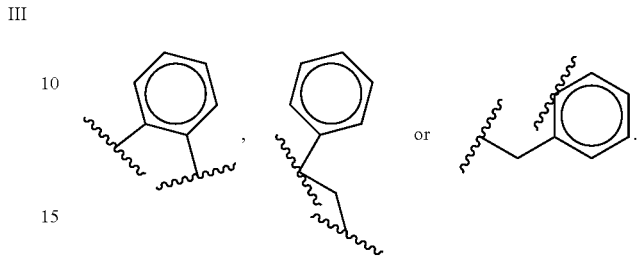

IV wherein

Ar is

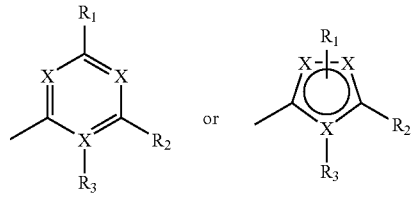

Each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine, $CH_2COOH$, $N(CH_3)_2$, $CH_2CH_2SCH_3$ or $CH_2$-piperidinyl;

$R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is absent, H, $NH_2$, $CON(CH_3)_2$, $CO_2H$, CN, $CH_2OH$, $CONH_2$, $CSNH_2$, CONHOH, $C(NH)NH_2$, $CONHNH_2$, $CONHCH_3$, $CH_2OCH_3$, CONH-cyclohexyl, $CO_2CH_3$,

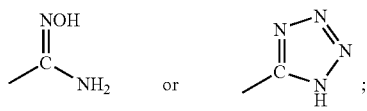

$R_5$ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2$-imidazole, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-indole, $CH_2$-thiophene, $CH_2$-cyclohexane, 4-chlorobenzyl, phenyl, 2-hydroxybenzyl, 4-tertbutoxybenzyl, $CH_2$-benzylimidazole, 4-aminobenzyl, $CH_2$-pryid-3-yl, $CH_2$-pryid-2-yl, $CH_2OH$, $(CH_2)_3NHC(NH)NH_2$ or $CH_2CH(CH_3)_2$;

$R_6$ is H, methyl, ethyl, propyl, isopropyl, $CH_2CO_2H$, $CH_2CO_2Et$, benzyl, or $CH_2$-(2-methoxynaphthyl); or, $R_5$ arid $R_6$ together form:

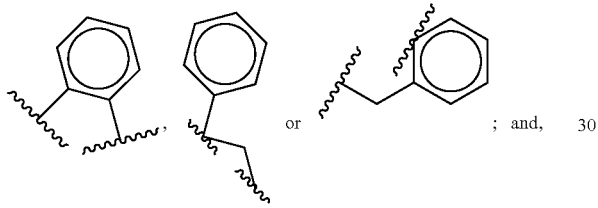

$R_7$ is absent, $NH(CH_2)_3$, $NHCOCH_2$, $NHCOCH_2CH_2$, NH-piperidine-$CH_2$, NHCO-pyridine, NHCONH-cyclohexane, O—$CH_2$, O—$(CH_2)_4$, CONH-cyclopentane, $CH_2NHCH_2CH_2$, $CH_2N^+H_2Cl^-CH_2CH_2$, $CH_2N(CH_2COOH)CH_2CH_2$, $CH_2N(CH_2CH_2N(CH_3)_2)CH_2CH_2$, $NHCH(CH_3)CH_2CH_2$, $CH_2$-Piperidine, $CH_2NHCH_2CH(CH_3)CH_2$, $CH_2NHCH(CONH_2)$, $CH_2N(CH_3)CH_2CH_2$, $CH_2N(CH_2CH_3)CH_2CH_2$, $CH_2N(CH_2CH_2$-morpholine$)CH_2CH_2$, $OCH_2CH(OH)CH_2$, $OCH_2COCH_2$, $OCH_2CH_2CH(OH)$, $OCH_2CH_2C(CH_3)_2$, $CH_2N(CH_2CH_2OCH_3)CH_2CH_2$,

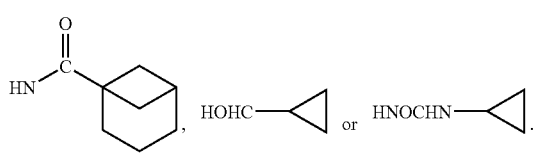

Another embodiment of the present invention includes compounds that may be used for inhibiting protein prenylation having the general structure of Formula V:

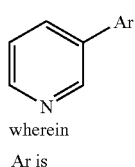

wherein
Ar is:

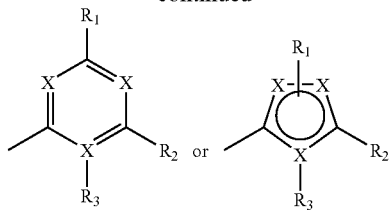

Each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

$R_2$ is $NH_2$, $CO_2CH_3$, $C(O)N_3$, $C(O)NH$-cyclohexane, 4-aminophenyl, $CH_2CNHNH_2$, $O(CH_2)_3CONHCOCH(NH_2)$benzyl, OH, $OCH_2CH_3$, $(CH_2)_4COOH$, $O(CH_2)_3COOH$, $O(CH_2)_4COOH$, $O(CH_2)_3COOCH_2CH_3$, $CH_2NHCH_2CH_2N(CH_3)_2$, benzamide, benzoic acid, thiophene carboxylic acid or urea-cyclopropane carboxylic acid; and, $R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$ Another embodiment of the present invention includes compounds that may be used for inhibiting protein prenylation having the general structure of Formula VI:

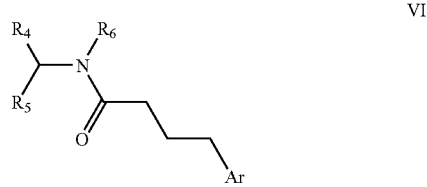

wherein,
Ar is:

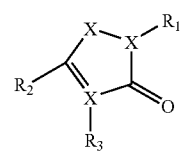

Each X is independently C or N;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl;

R₂ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine, CH₂COOH, N(CH₃)₂, CH₂CH₂SCH₃ or CH₂-piperidinyl;

R₃ is absent, H, CH₂CH₂OH, CH₂CH₂OCH₃, CH₂CH₂N(CH₃)₂, CH₂CH₂NHCH₃, CH₂OH, (CH₂)₃OH, CH₂CH₂CO₂H, CH₂CO₂H, CH₂CH₂SOCH₃, CH₂CH₂SO₂CH₃, CH₂CH₂SH or CH₂CH₂SCH₃;

R₄ is absent, H, NH₂, CON(CH₃)₂, CO₂H, CN, CH₂OH, CONH₂, CSNH₂, CONHOH, C(NH)NH₂, CONHNH₂, CONHCH₃, CH₂OCH₃, CONH-cyclohexyl, CO₂CH₃,

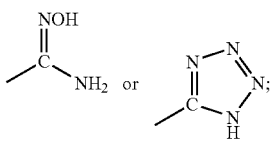

R₅ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, CH₂CH₂-phenyl, 4-fluorobenzyl, 4-phenylbenzyl, CH₂-imidazole, CH₂COOH, CH₂CH₂COOH, (CH₂)₄NH₂, CH₂CH₂SCH₃, 4-hydroxybenzyl, CH₂-naphthyl, 4-methylbenzyl, CH₂-indole, CH₂-thiophene, CH₂-cyclohexane, 4-chlorobenzyl, phenyl, 2-hydroxybenzyl, 4-tertbutoxybenzyl, CH₂-benzylimidazole, 4-aminobenzyl, CH₂-pryid-3-yl, CH₂-pryid-2-yl, CH₂OH, (CH₂)₃NHC(NH)NH₂ or CH₂CH(CH₃)₂; and, R₆ is H, methyl, ethyl, propyl, isopropyl, CH₂CO₂H, CH₂CO₂Et, benzyl, or CH₂-(2-methoxynaphthyl); or, R₅ and R₆ together form:

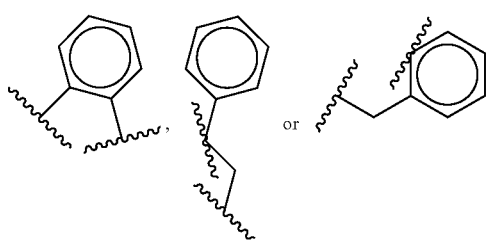

Another embodiment of the present invention includes compounds that may be used for inhibiting protein prenylation having the general structure of a formula selected from the group consisting of Formulae VII-X:

VII

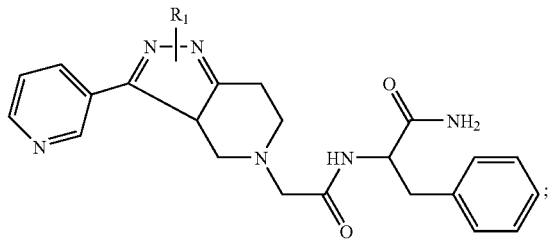

VIII

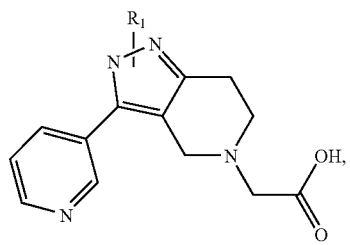

IX

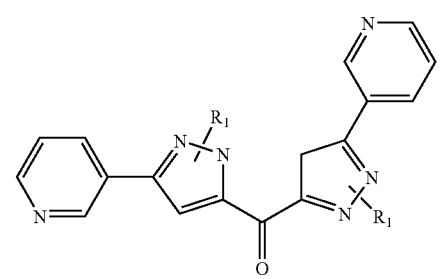

X wherein R₁ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, CH₂CF₃, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethyl pyrazole, ethanol, or 3,4-methylenedioxyphenyl.

Specific compounds of the present invention useful for protein prenylation are shown below in Table 1.

TABLE 1
1001
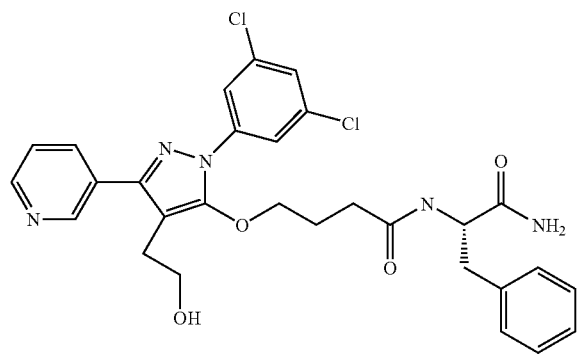
1002
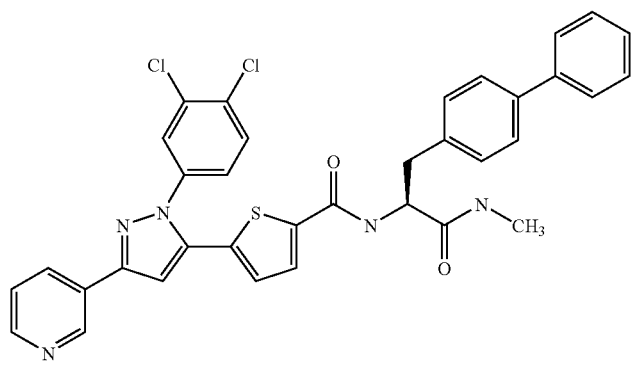
1003
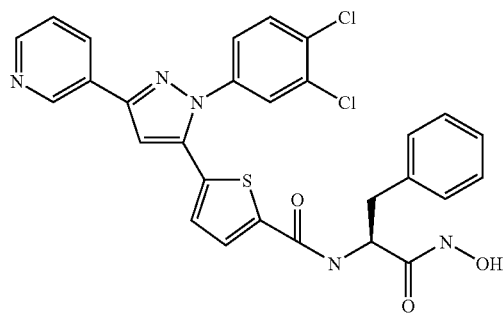
1004
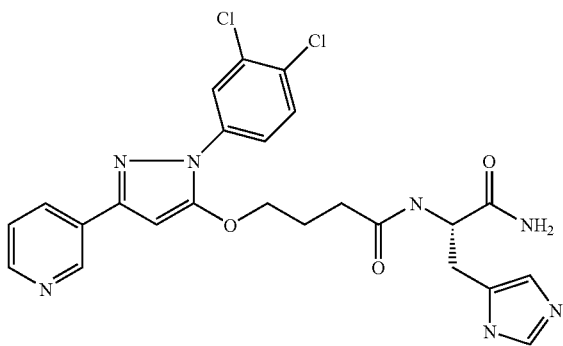

TABLE 1-continued
1005
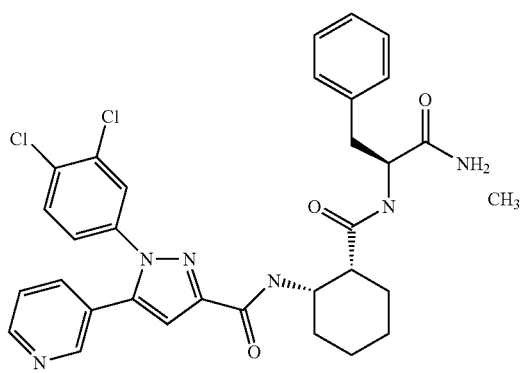
1006
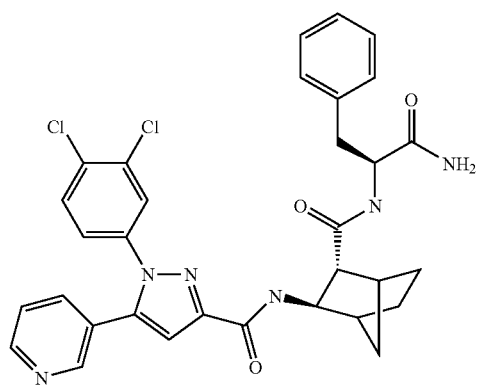
1007
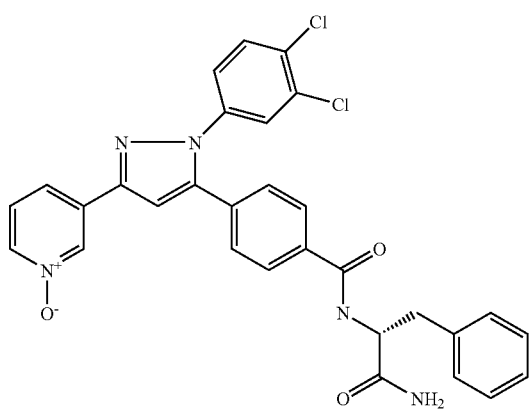
1008
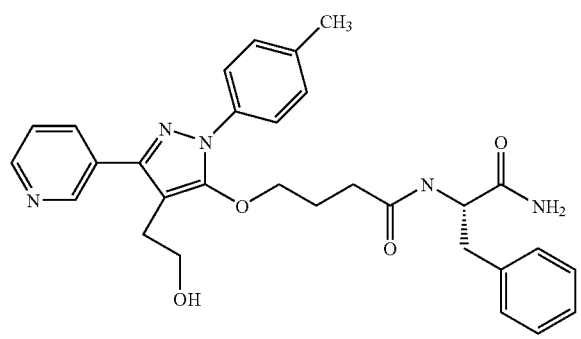

TABLE 1-continued
1009 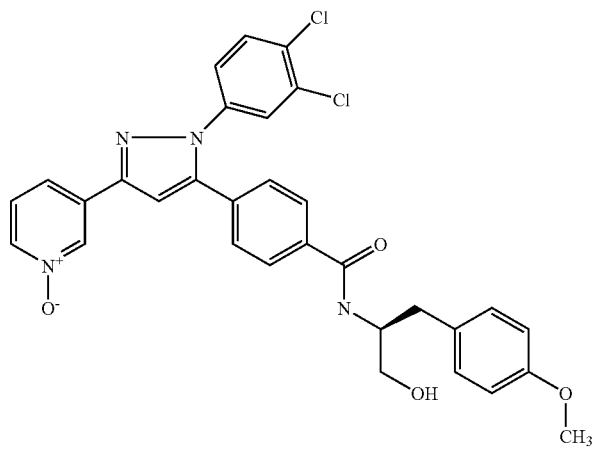
1010 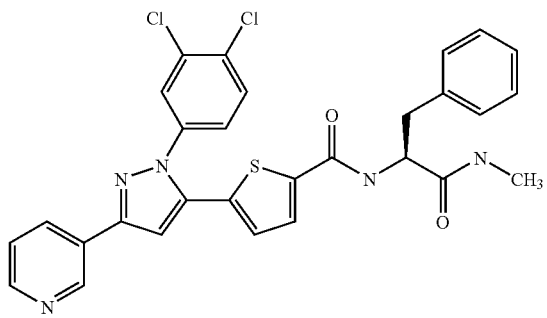
1011 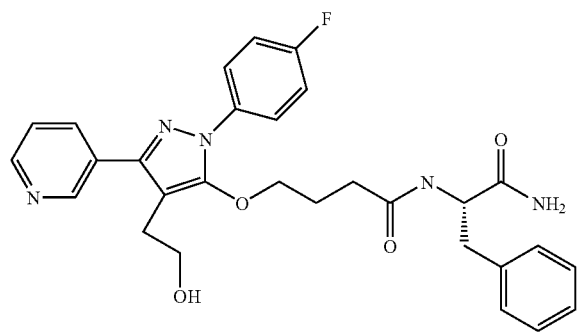
1012 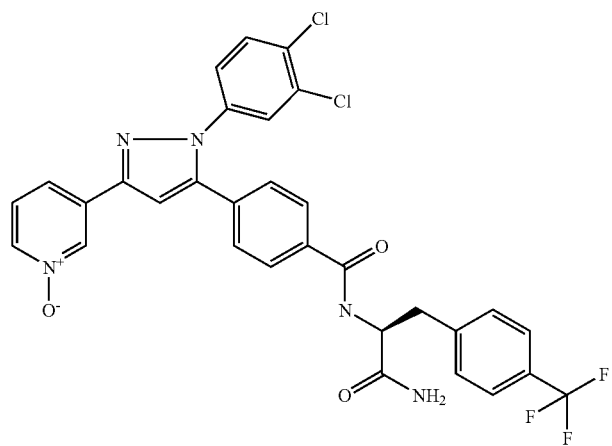

TABLE 1-continued
| 1013 | 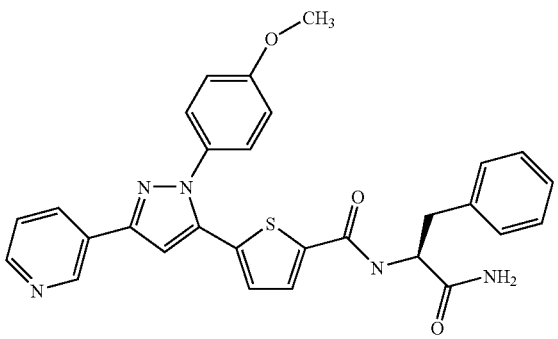 |
| 1014 | 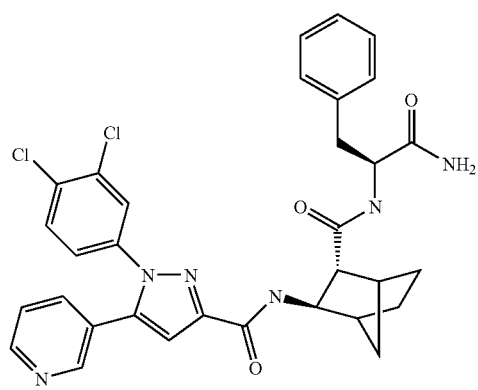 |
| 1015 | 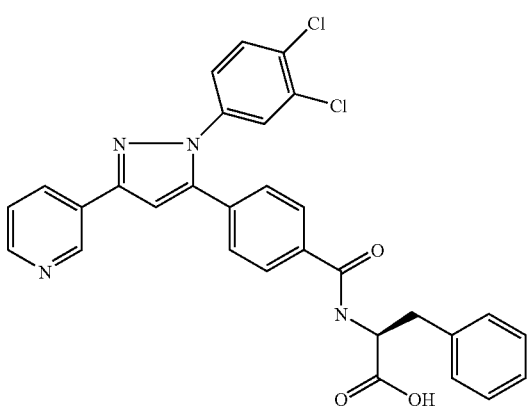 |
| 1016 | 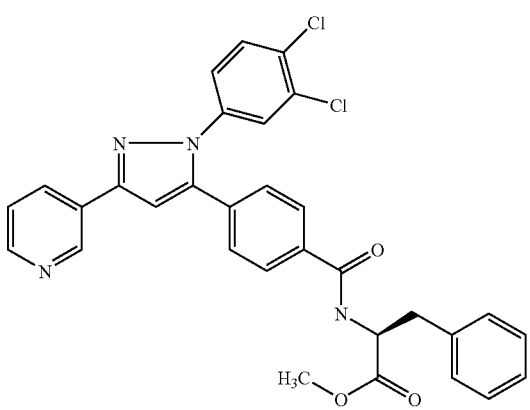 |

TABLE 1-continued
1017
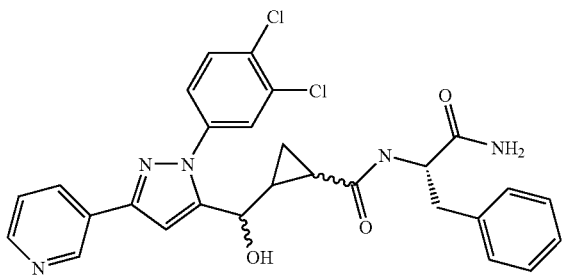
1018
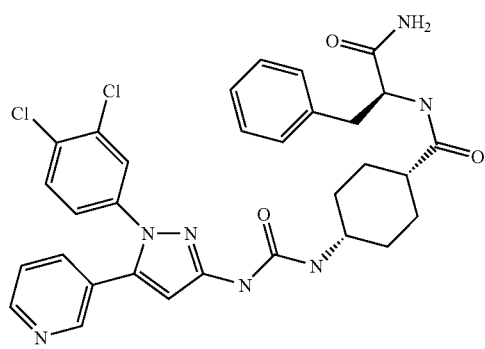
1019
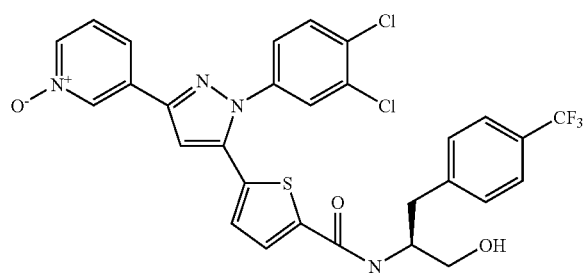
1020
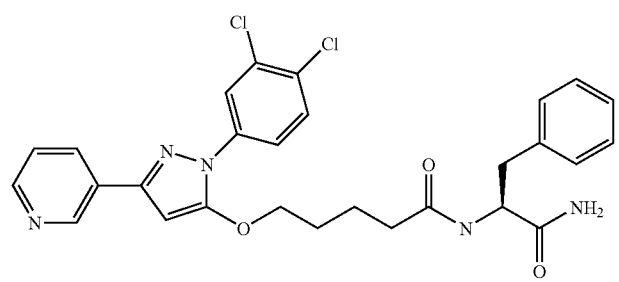
1021
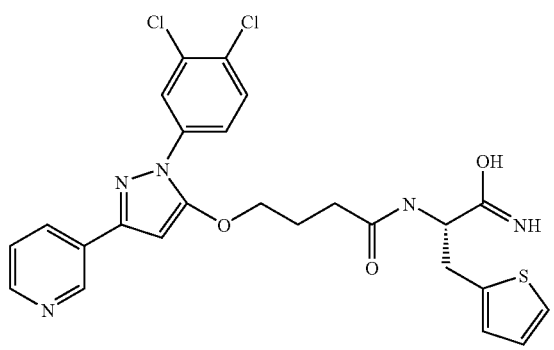

TABLE 1-continued
1022 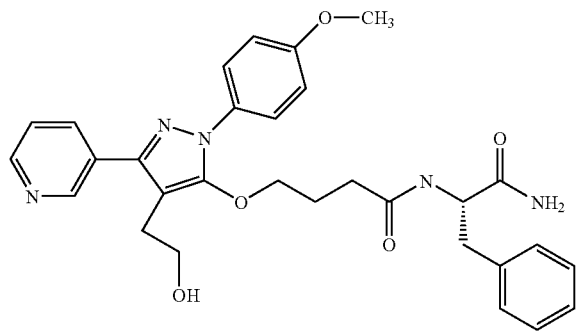
1023 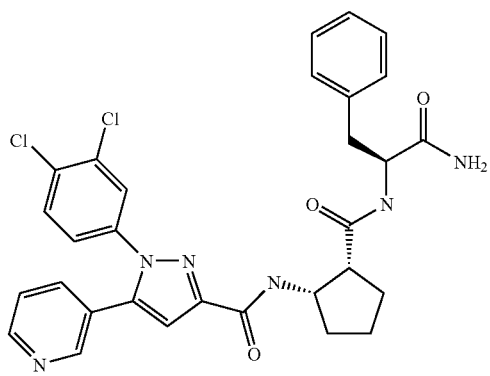
1024 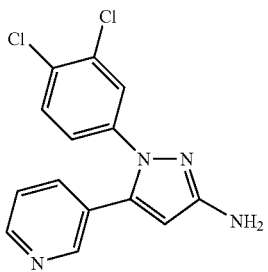
1025 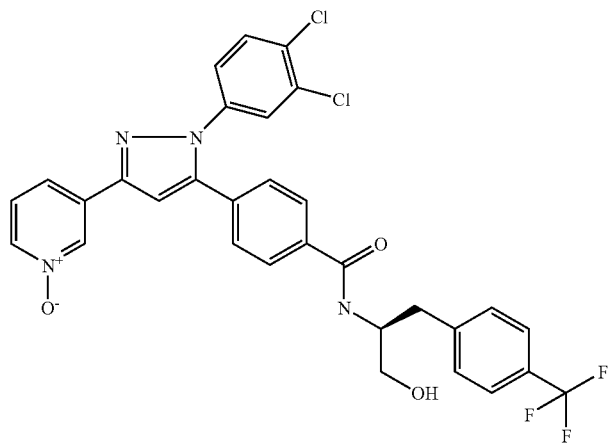

TABLE 1-continued
1026 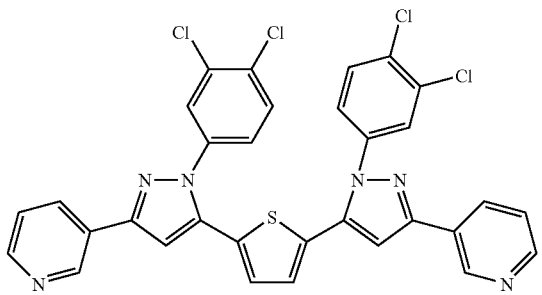
1027 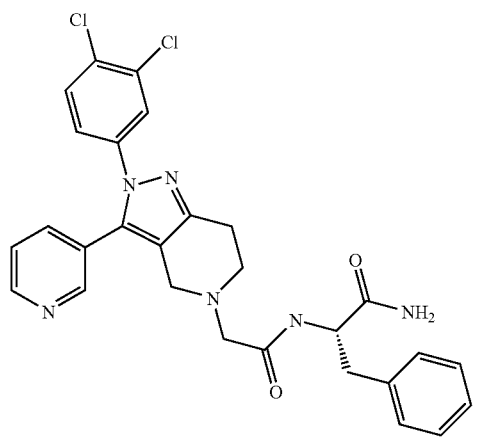
1028 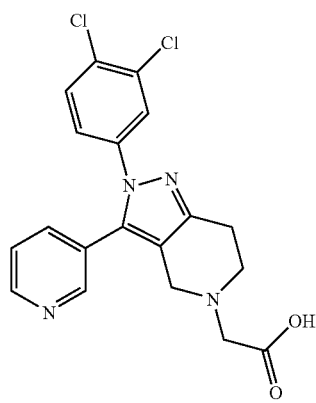
1029 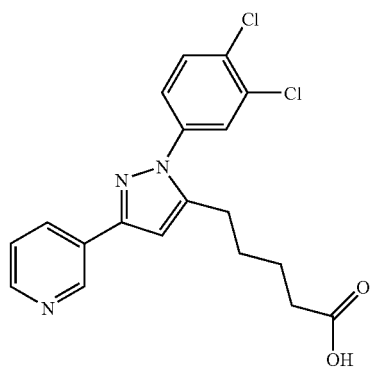

TABLE 1-continued
1030 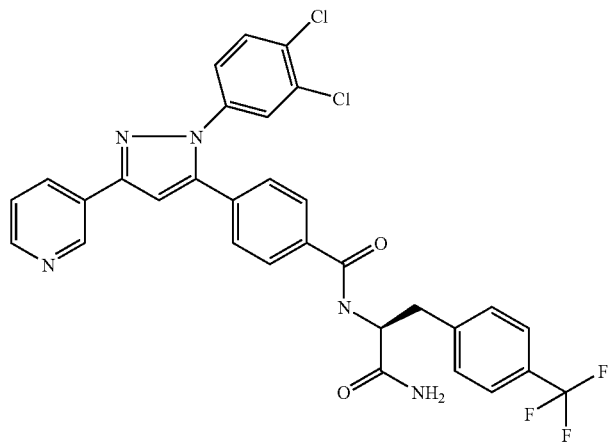
1031 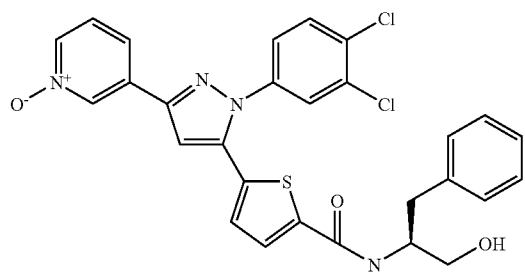
1032 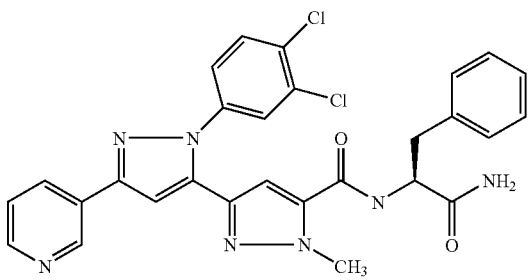
1033 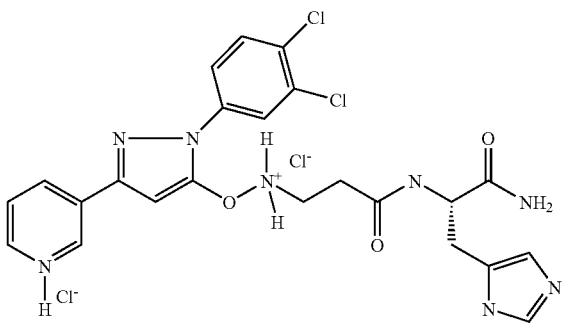

TABLE 1-continued
1034 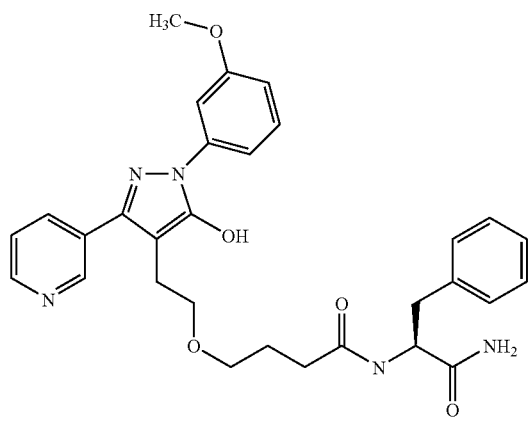
1035 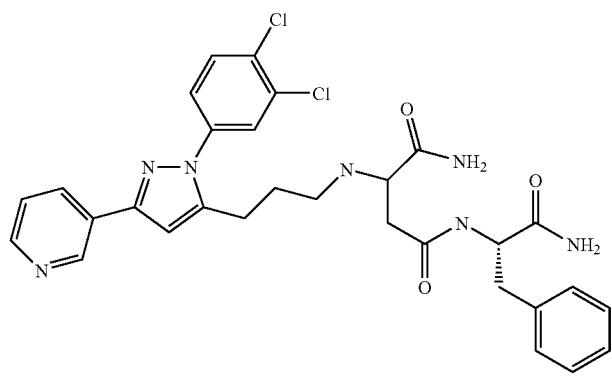
1036 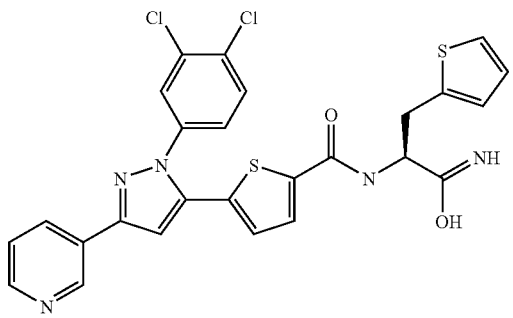
1037 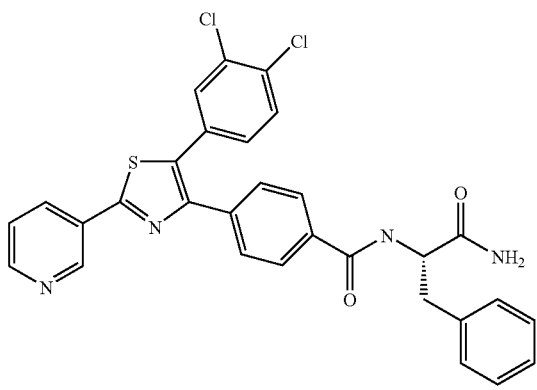

TABLE 1-continued
1038
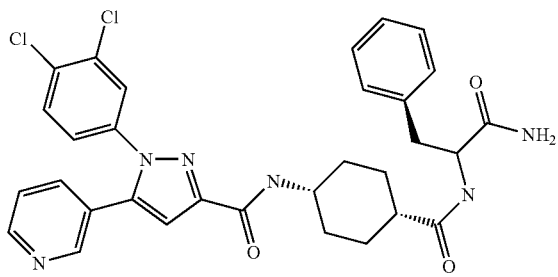
1039
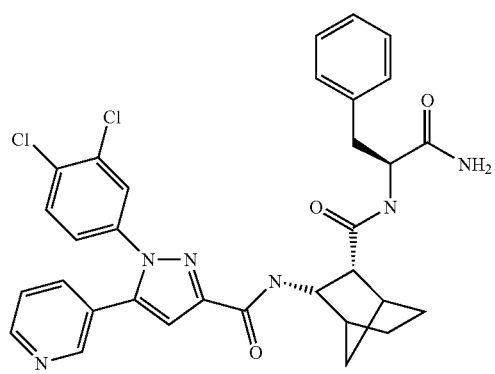
1040
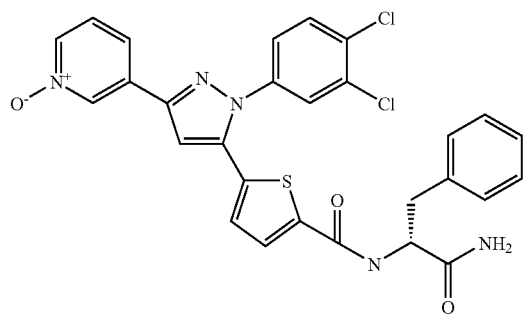
1041
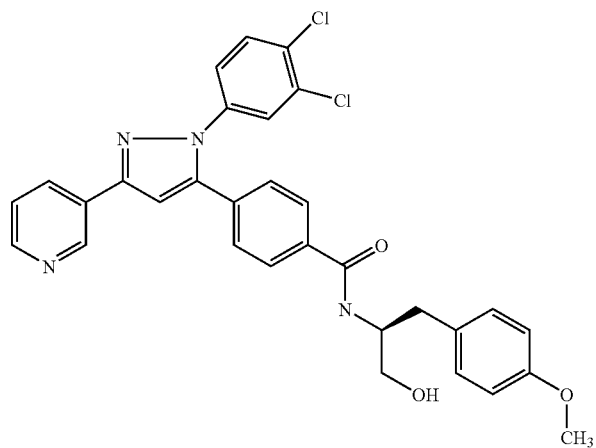

TABLE 1-continued
1042
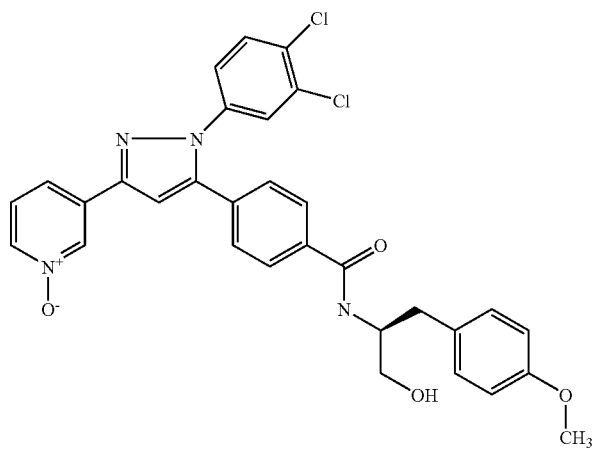
1043
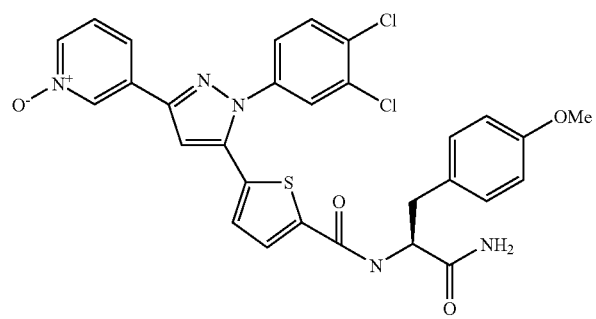
1044
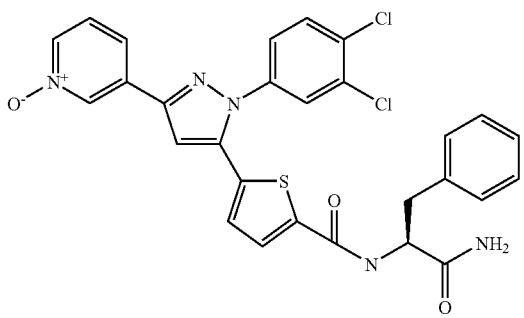
1045
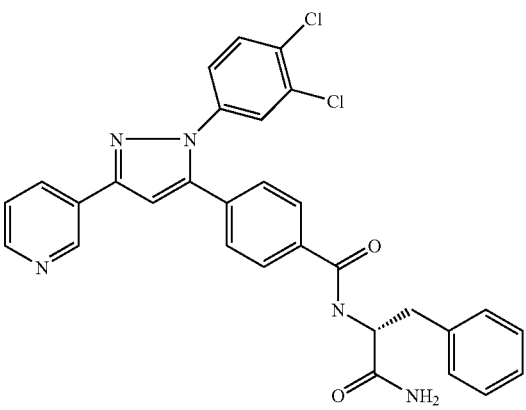

TABLE 1-continued
1046 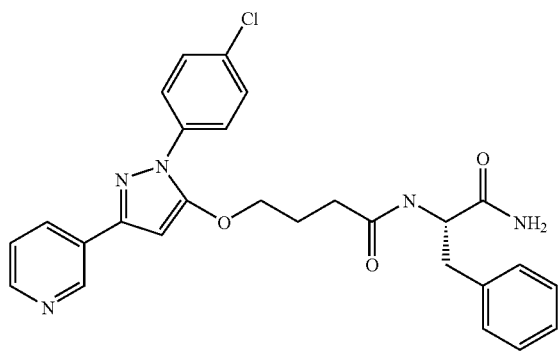
1047 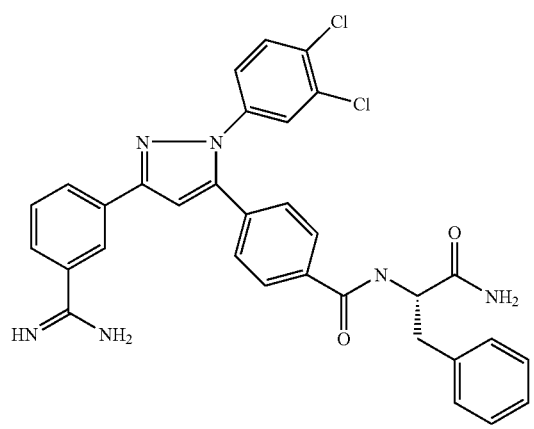
1048 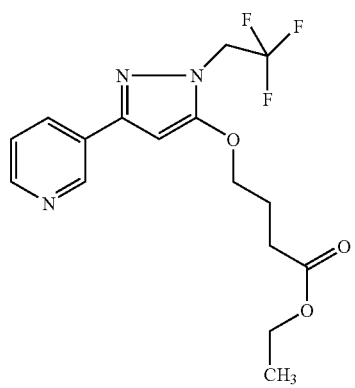
1049 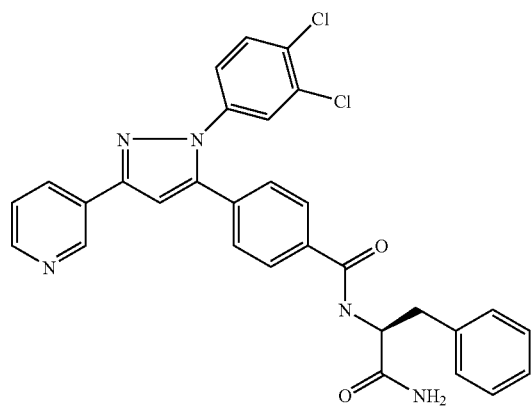

TABLE 1-continued
1050 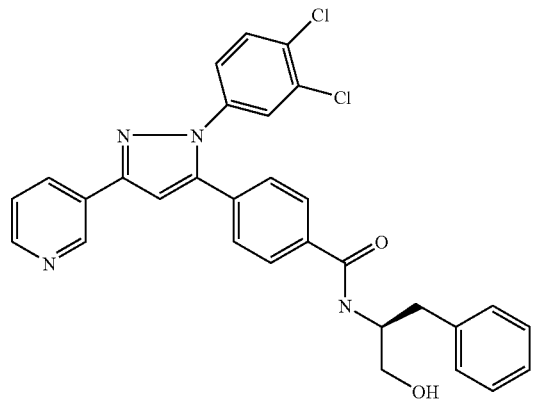
1051 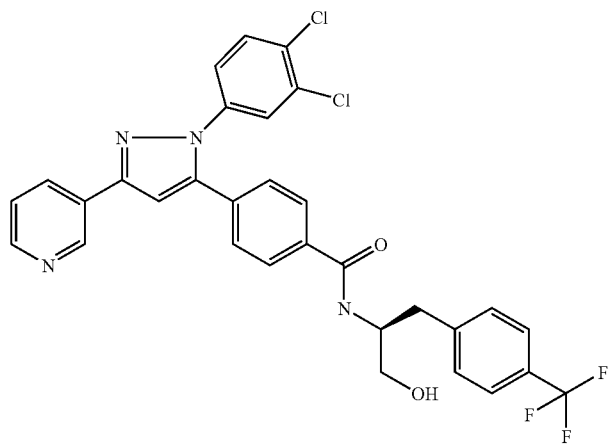
1052 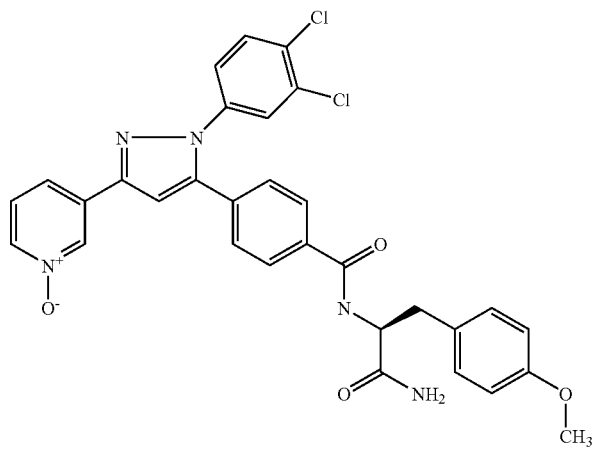
1053 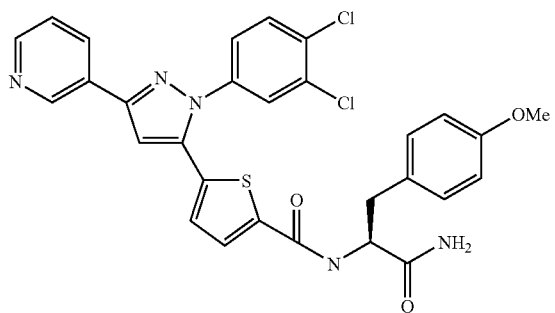

TABLE 1-continued
1054
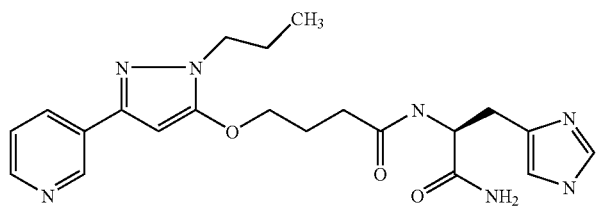
1055
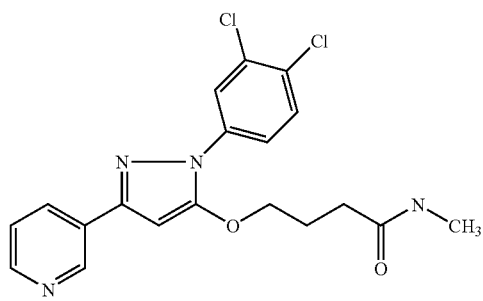
1056
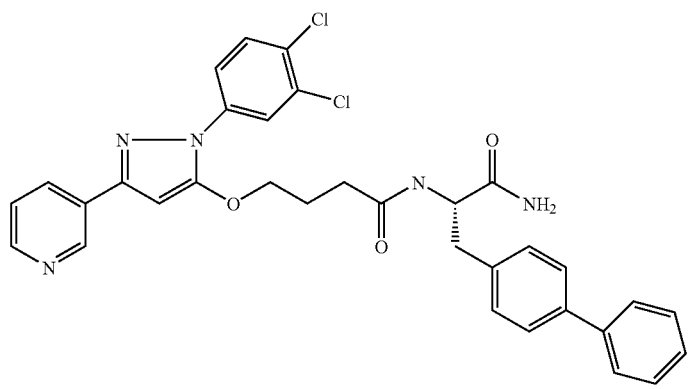
1057
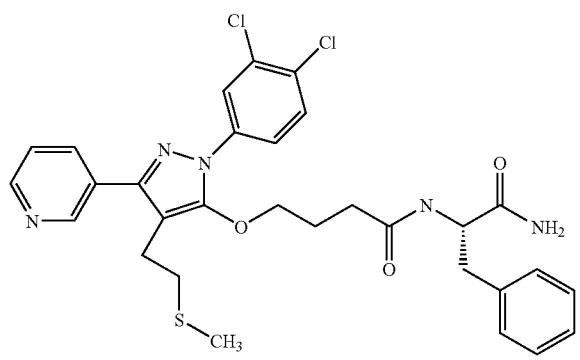
1058
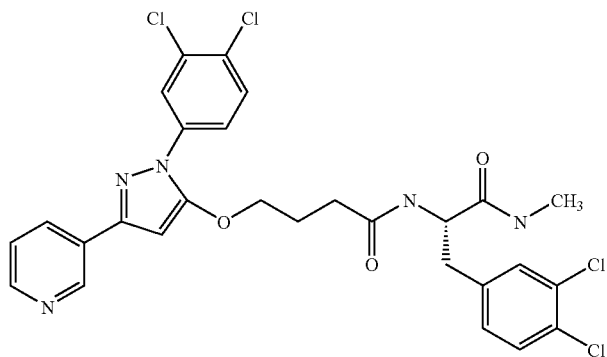

TABLE 1-continued
1059 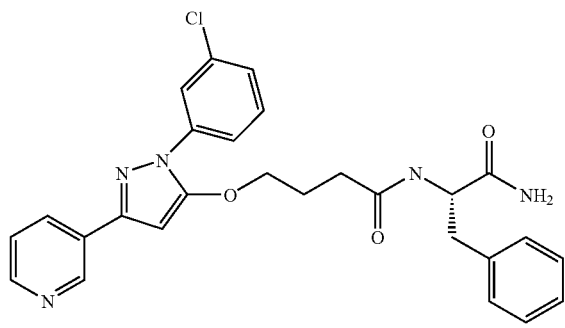
1060 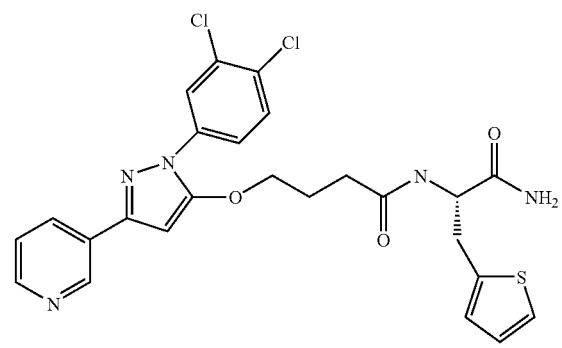
1061 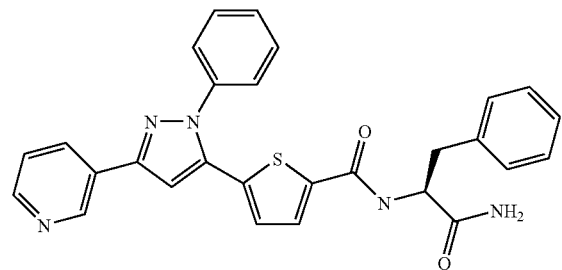
1062 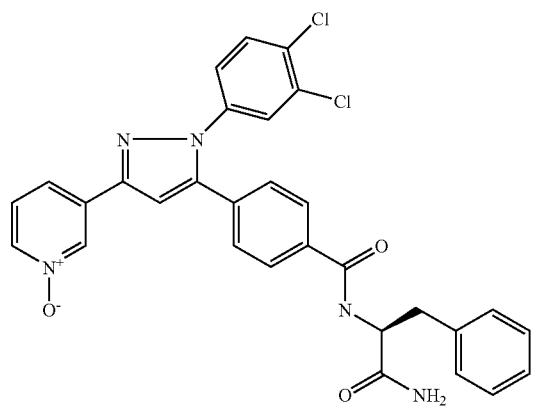

TABLE 1-continued
| | |
|---|---|
| 1063 | 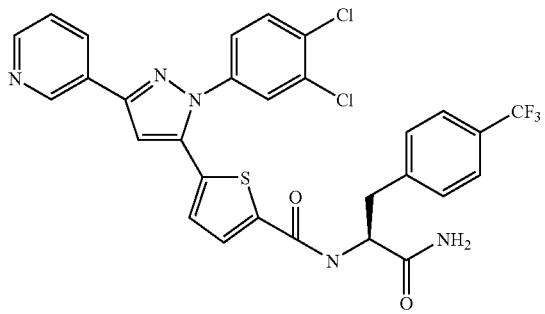 |
| 1064 | 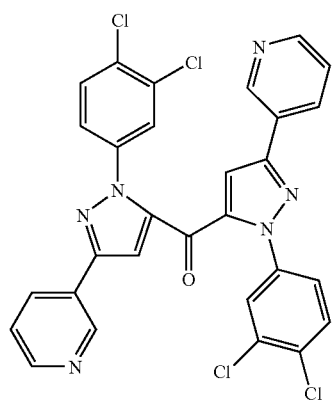 |
| 1065 | 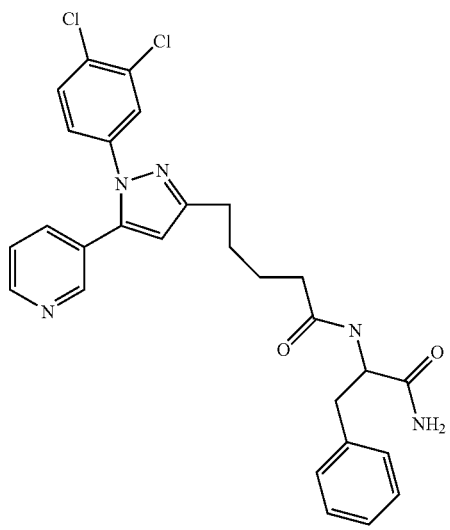 |
| 1066 | 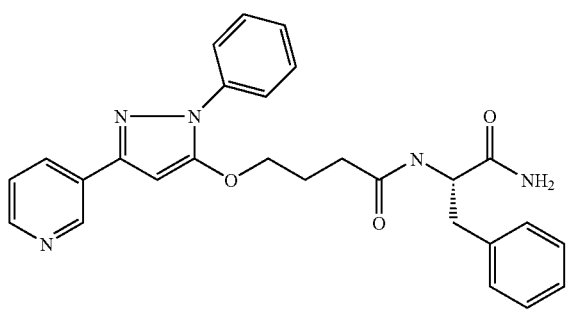 |

TABLE 1-continued
1067 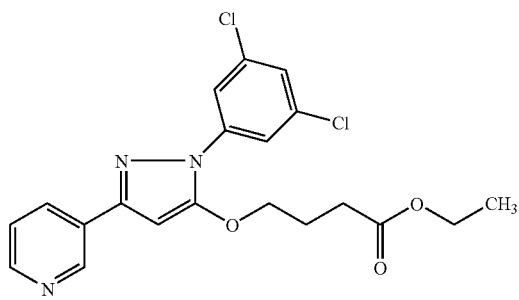
1068 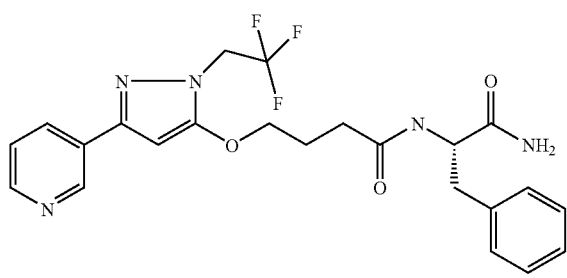
1069 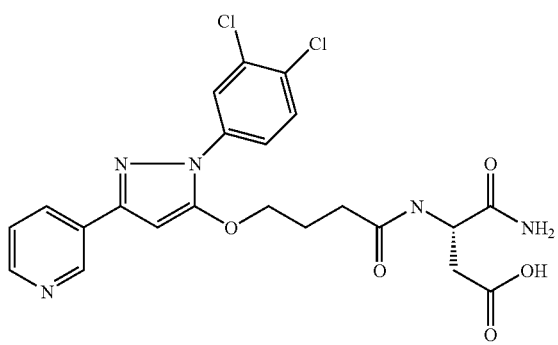
1070 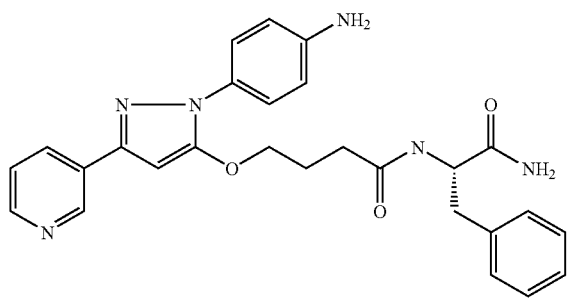
1071 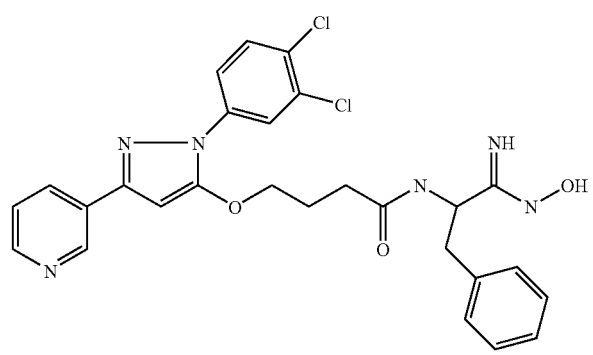

TABLE 1-continued
| | |
|---|---|
| 1072 | 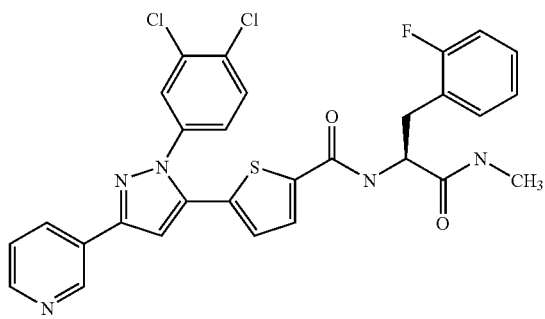 |
| 1073 | 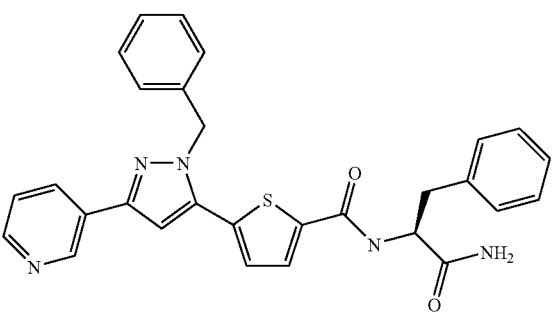 |
| 1074 | 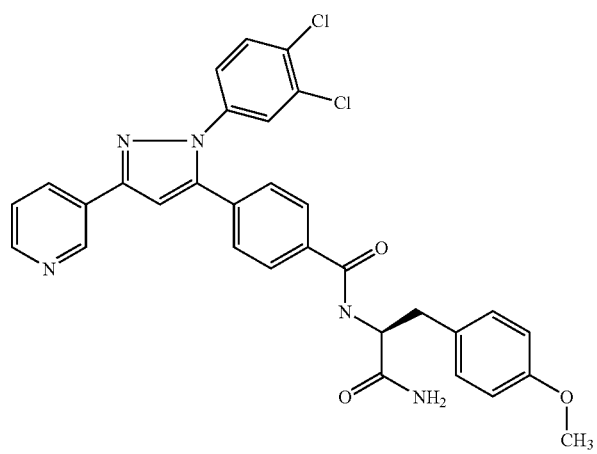 |
| 1075 | 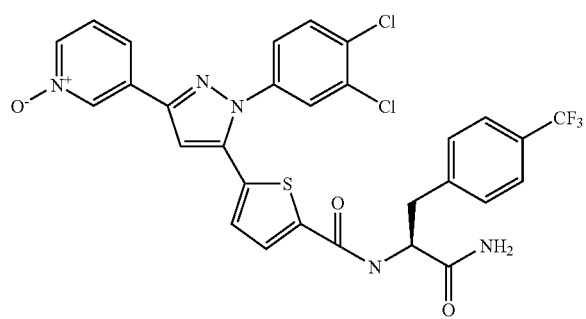 |

TABLE 1-continued
1076 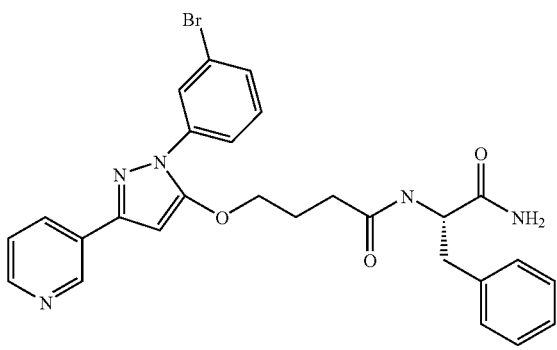
1077 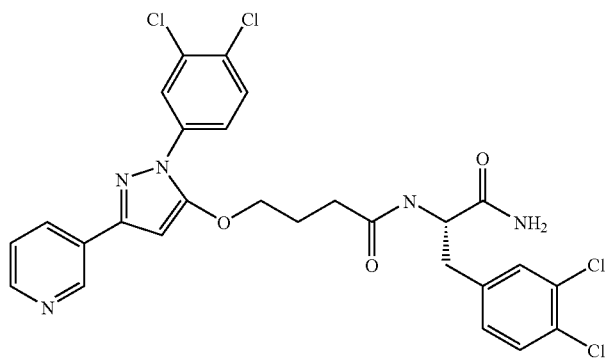
1078 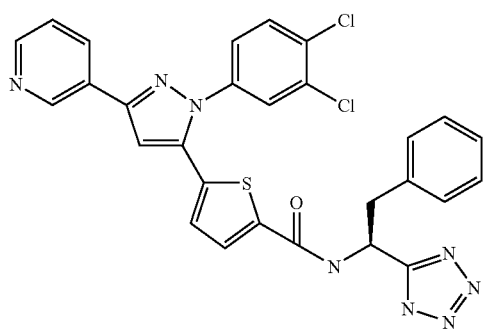
1079 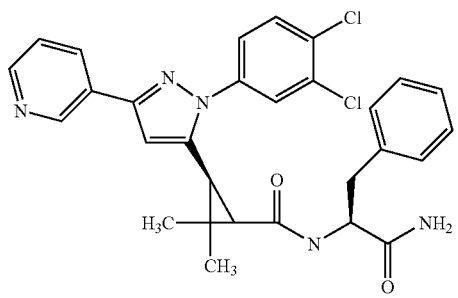
1080 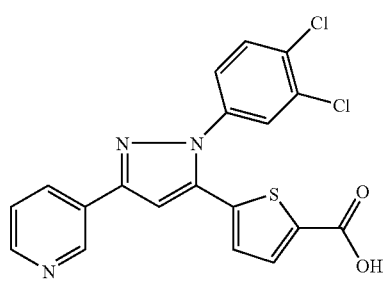

TABLE 1-continued
1081 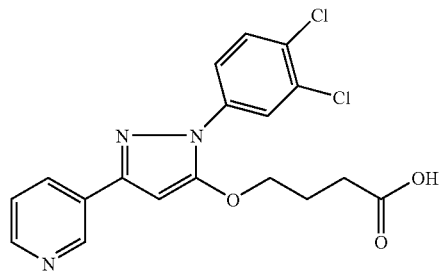
1082 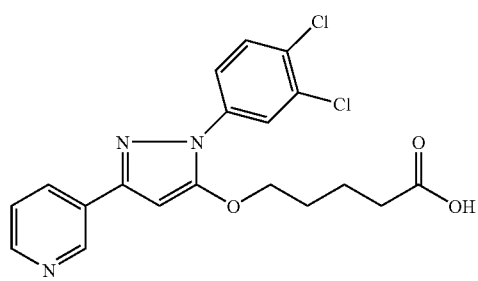
1083 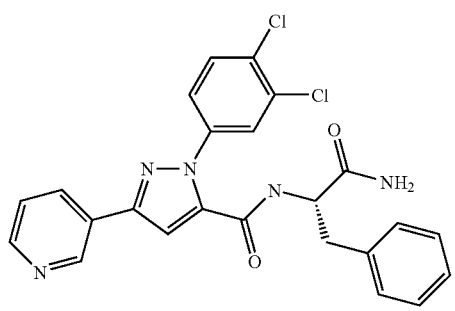
1084 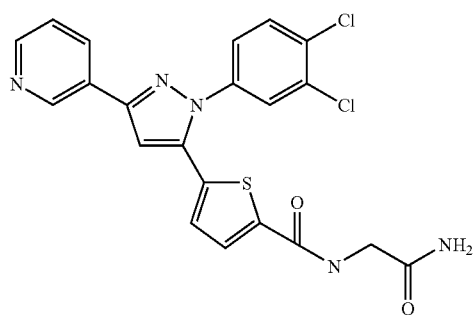
1085 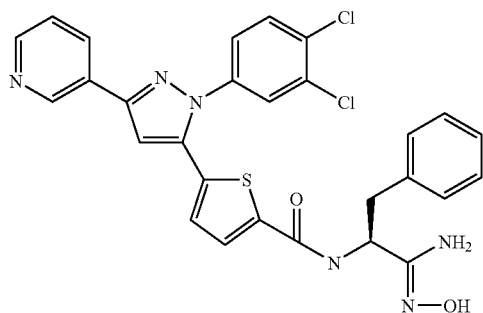

TABLE 1-continued
1086
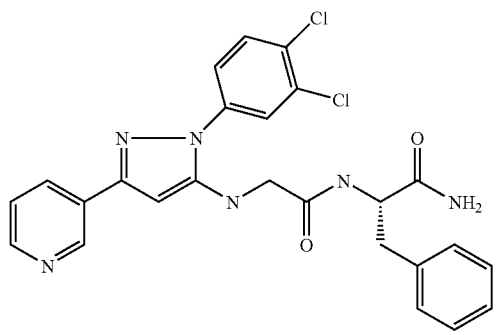
1087
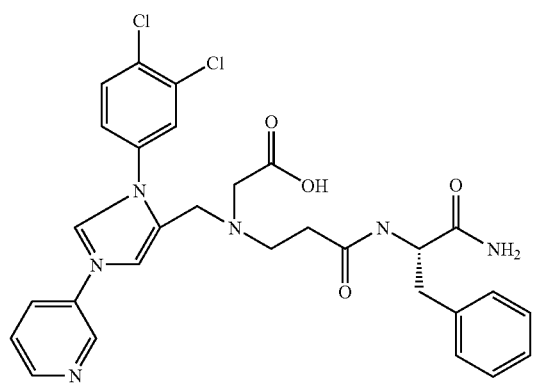
1088
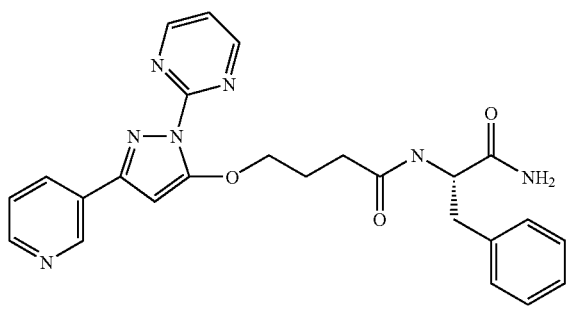
1089
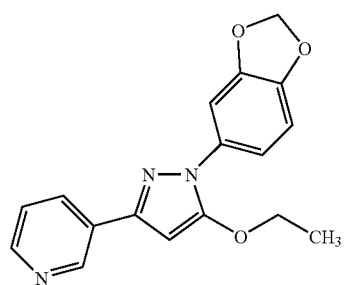

TABLE 1-continued
| 1090 | 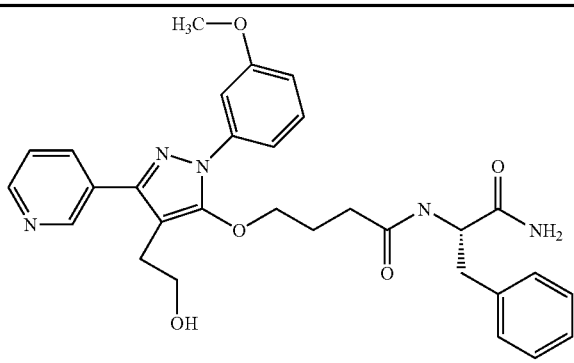 |
| --- | --- |
| 1091 | 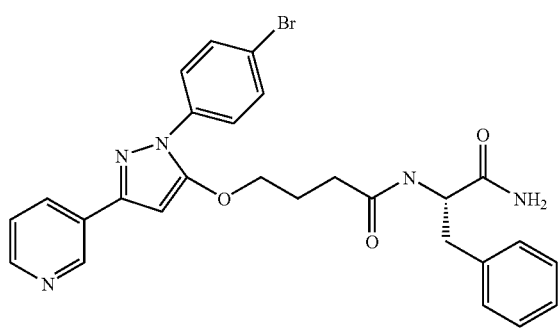 |
| 1092 | 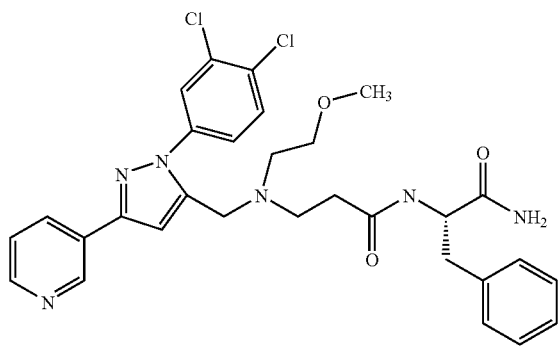 |
| 1093 | 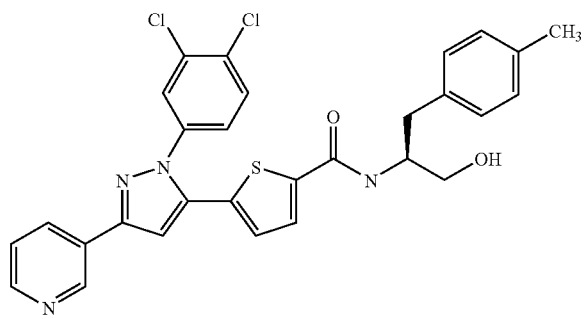 |

TABLE 1-continued
1094 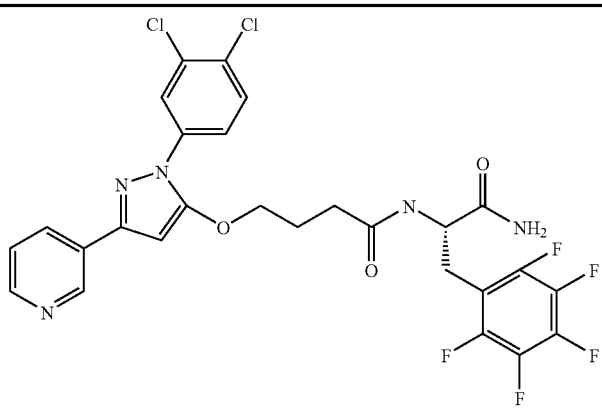
1095 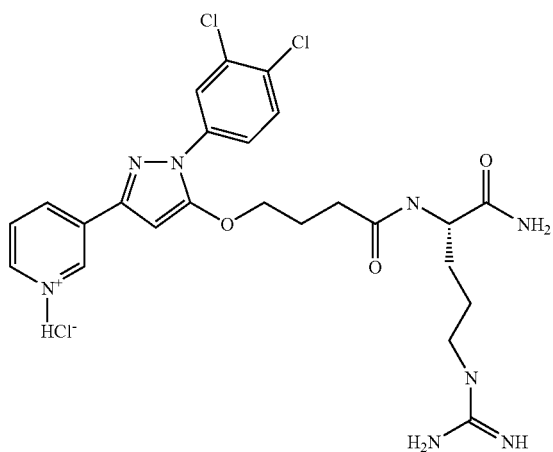
1096 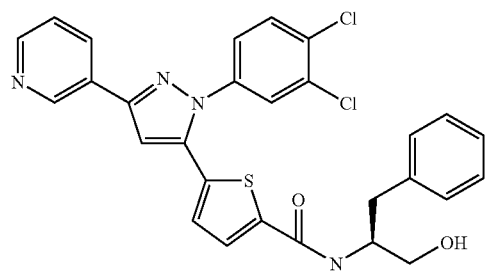
1097 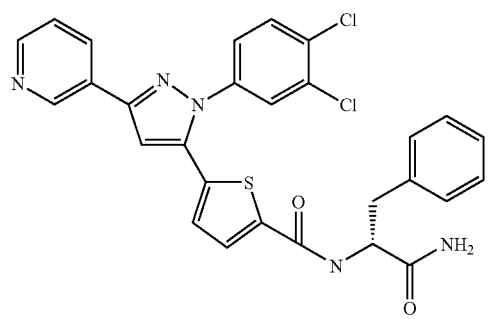

TABLE 1-continued
1098
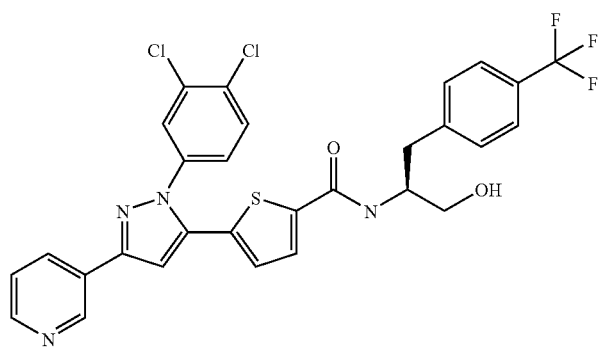
1099
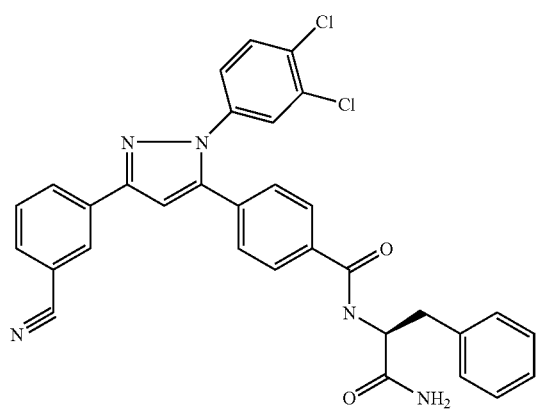
1100
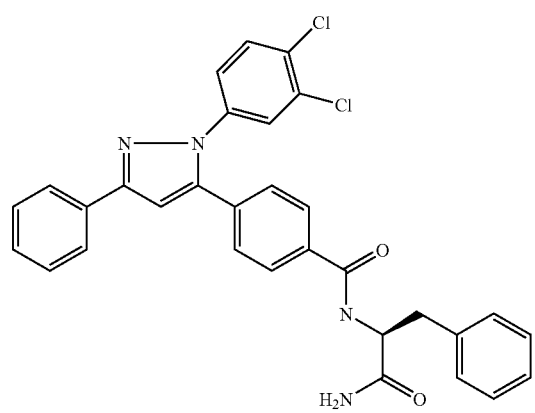
1101
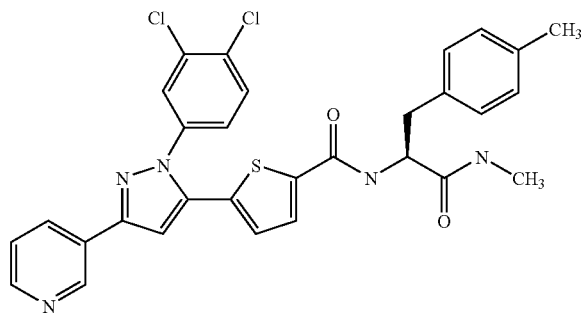

TABLE 1-continued
1102
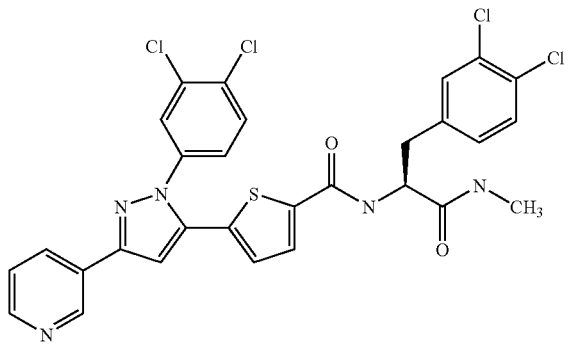
1103
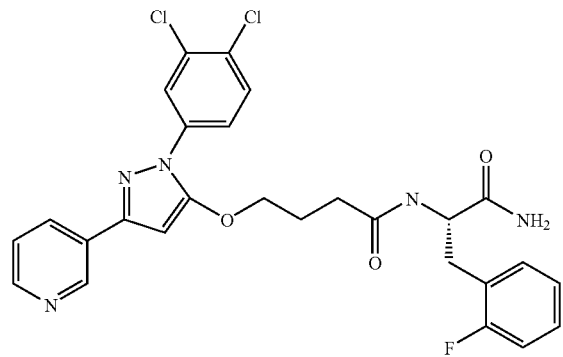
1104
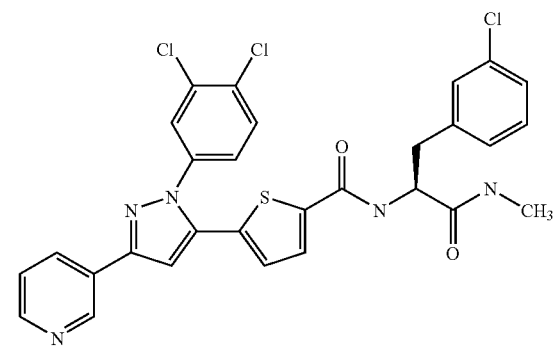
1105
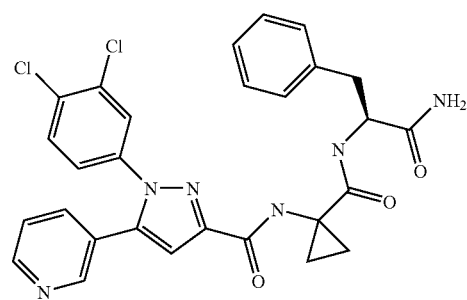

TABLE 1-continued
| | |
|---|---|
| 1106 | 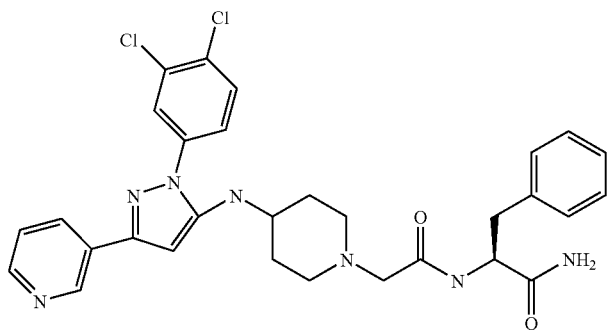 |
| 1107 | 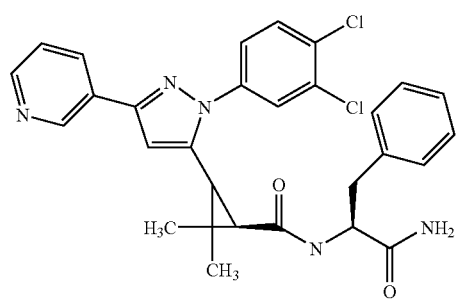 |
| 1108 | 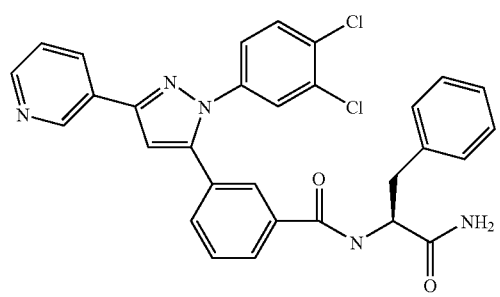 |
| 1109 | 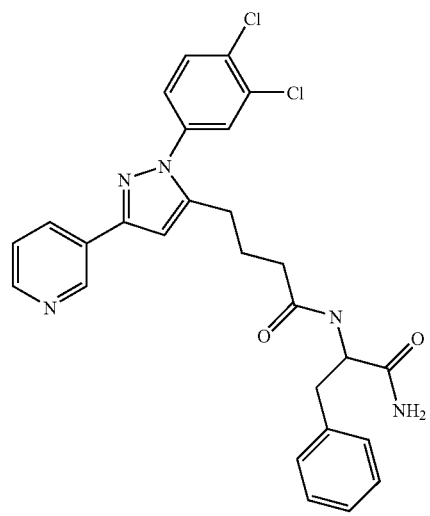 |

TABLE 1-continued
1110 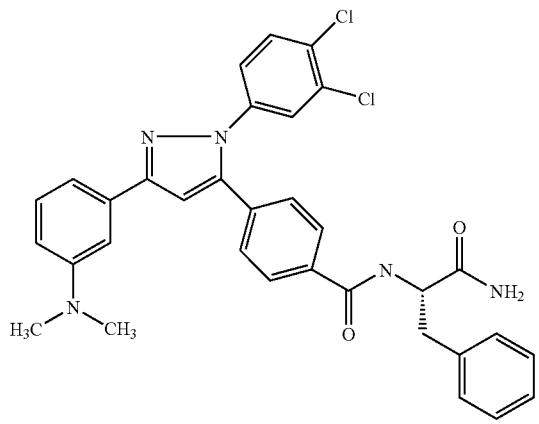
1111 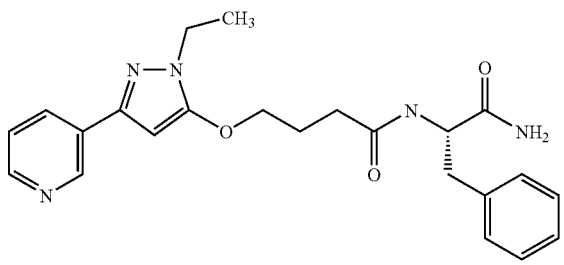
1112 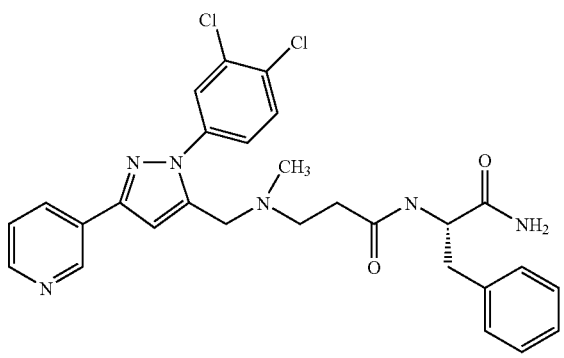
1113 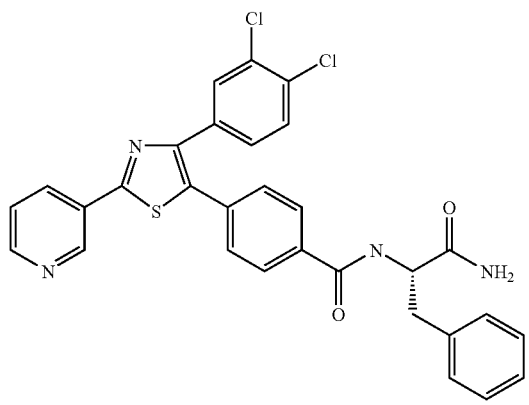

TABLE 1-continued
| | |
|---|---|
| 1114 | 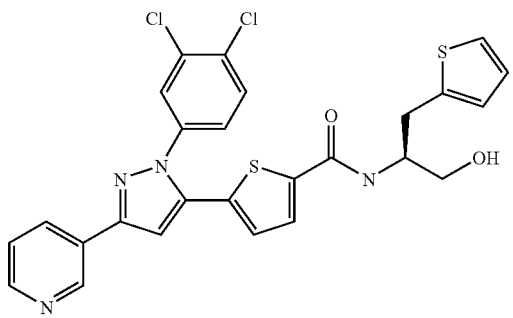 |
| 1115 | 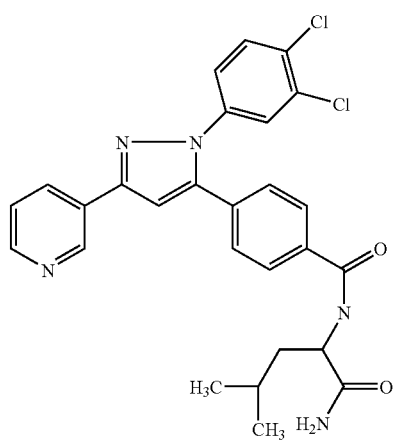 |
| 1116 | 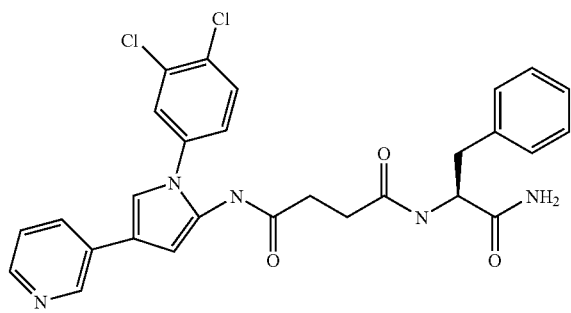 |
| 1117 | 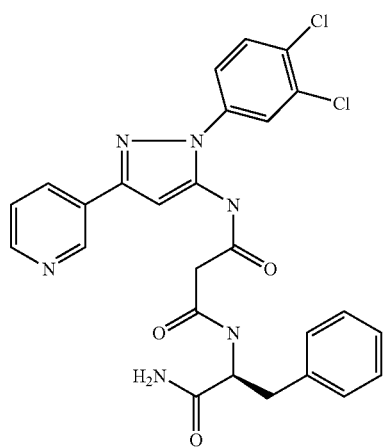 |

TABLE 1-continued
| | |
|---|---|
| 1118 | 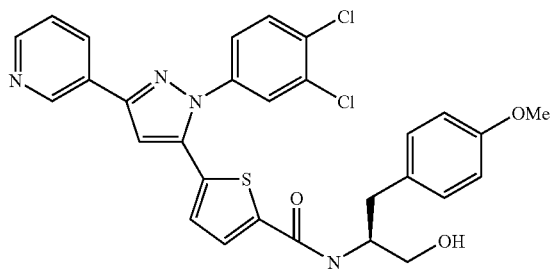 |
| 1119 | 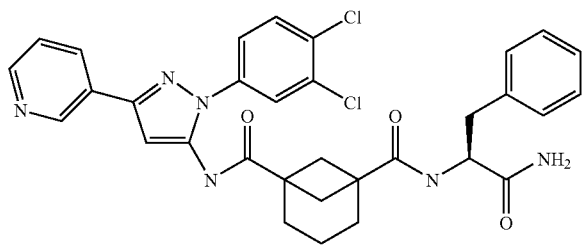 |
| 1120 | 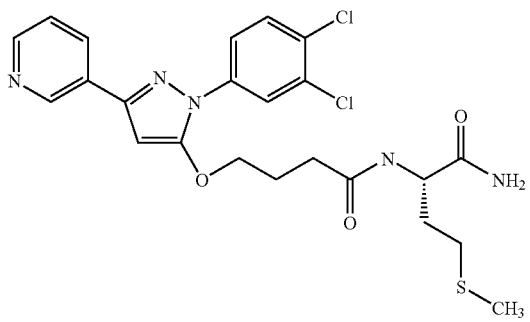 |
| 1121 | 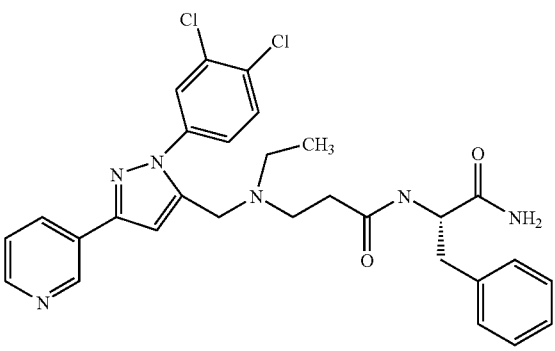 |
| 1122 | 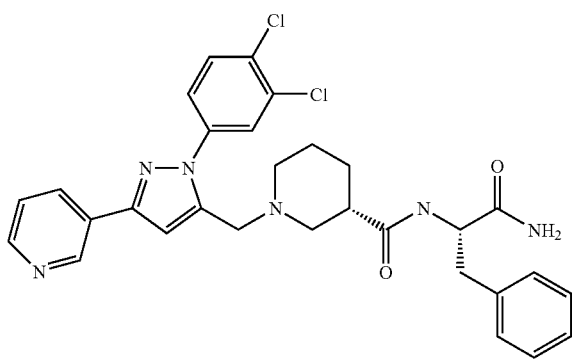 |

TABLE 1-continued
1123 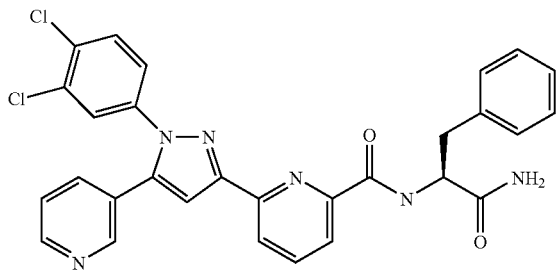
1124 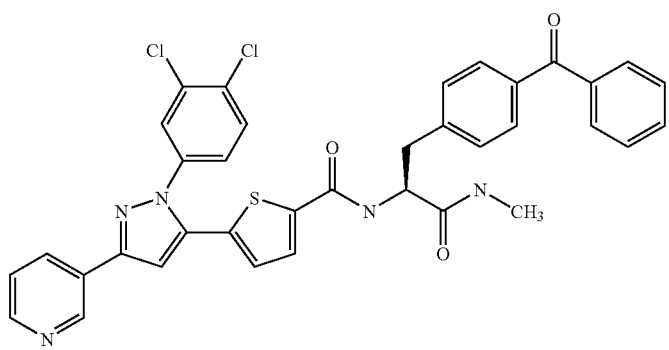
1125 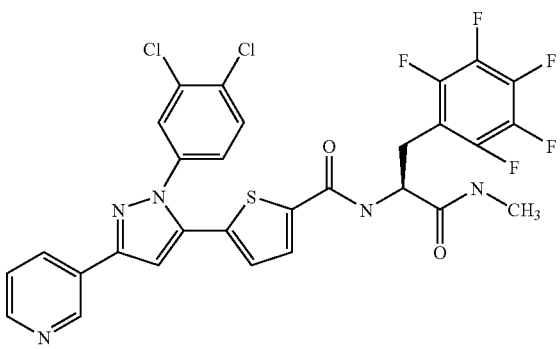
1126 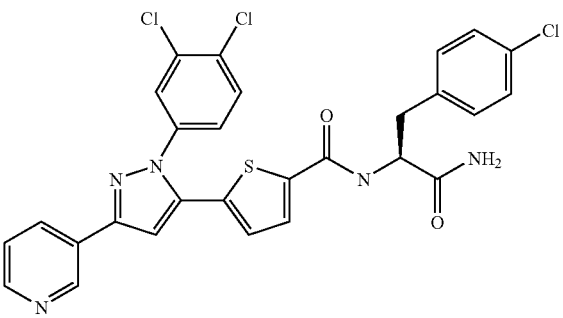
1127 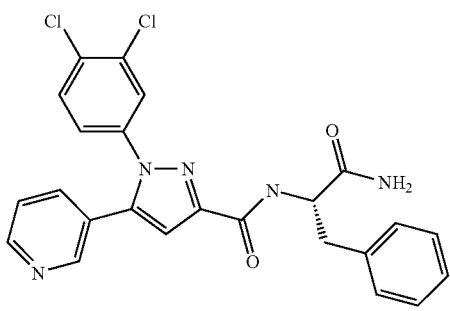

TABLE 1-continued
1128 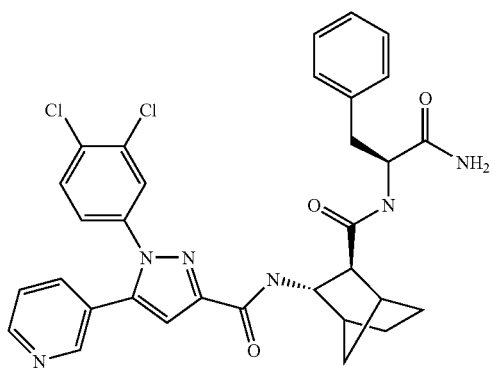
1129 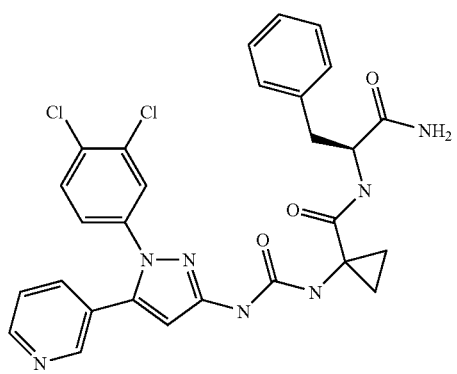
1130 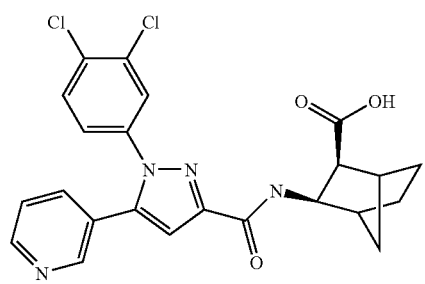
1131 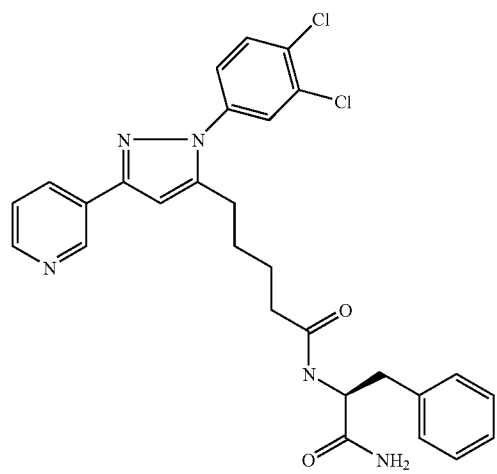

TABLE 1-continued
1132 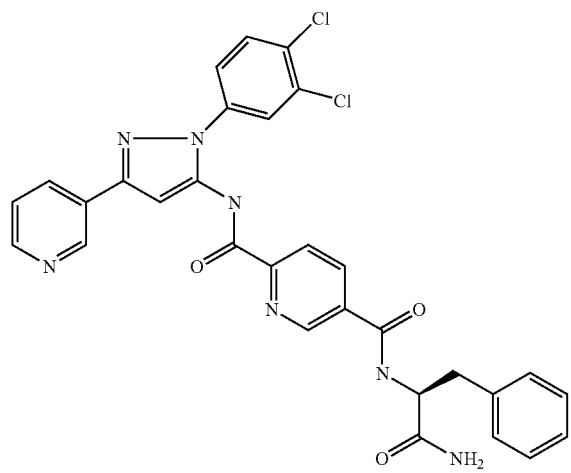
1133 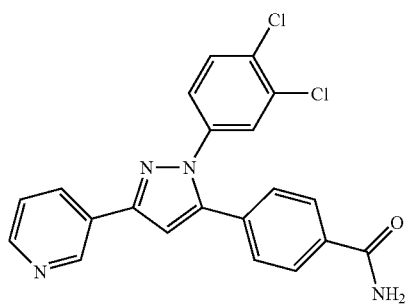
1134 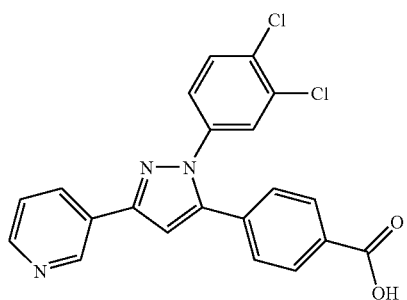
1135 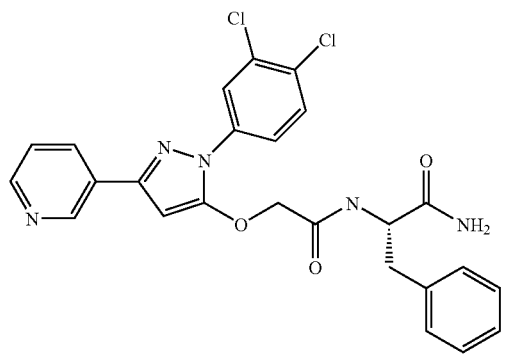

TABLE 1-continued
| 1136 | 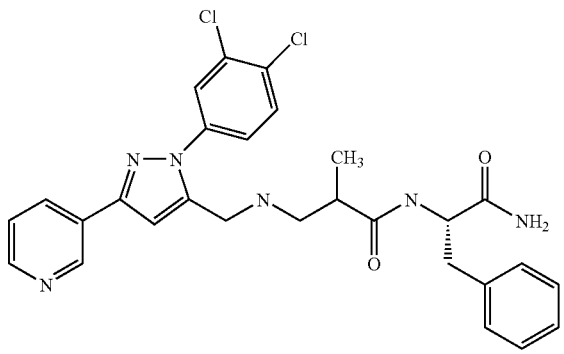 |
| 1137 | 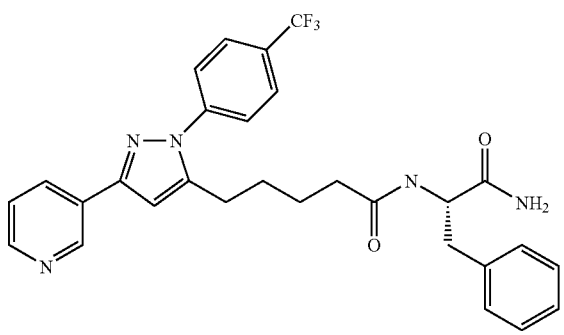 |
| 1138 | 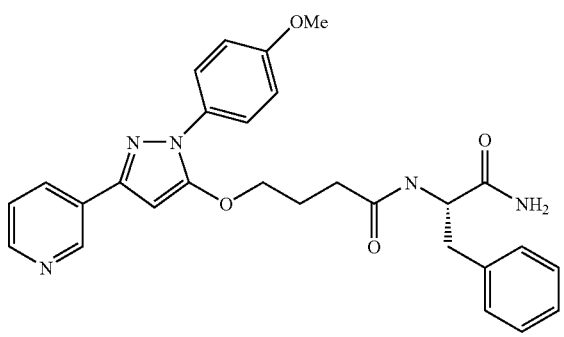 |
| 1139 | 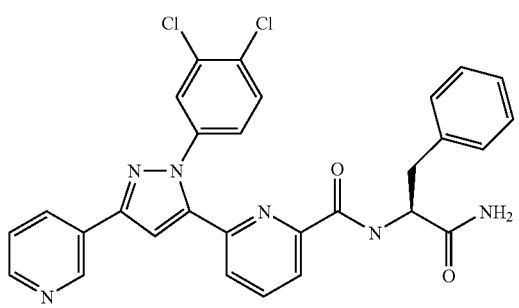 |
| 1140 | 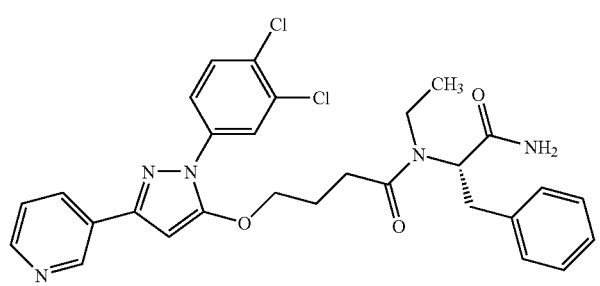 |

TABLE 1-continued
| | |
|---|---|
| 1141 | 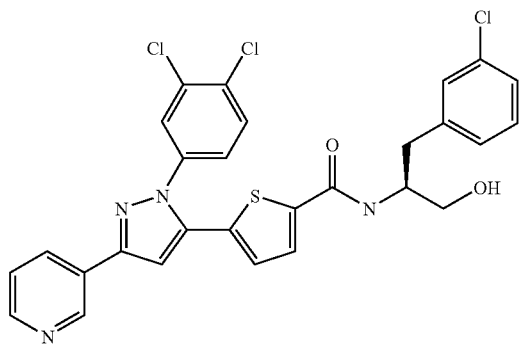 |
| 1142 | 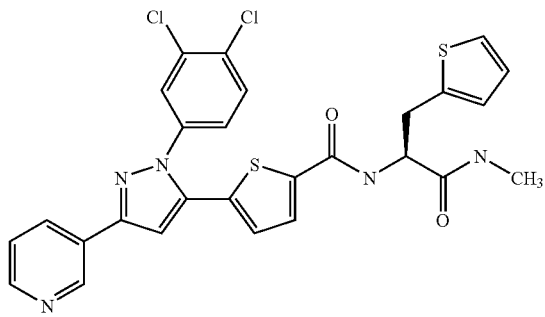 |
| 1143 | 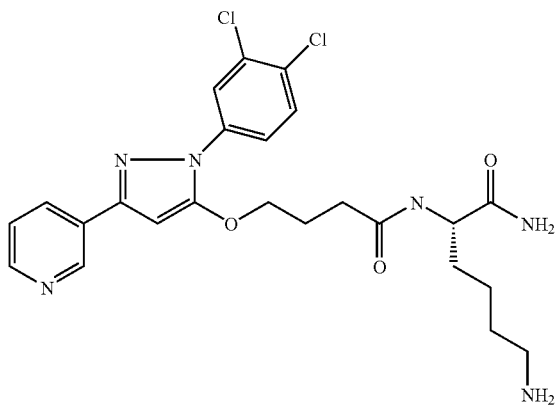 |
| 1144 | 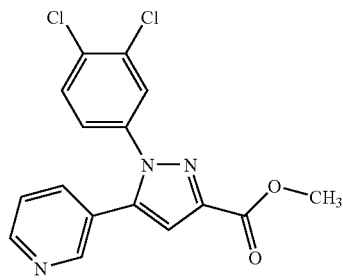 |
| 1145 | 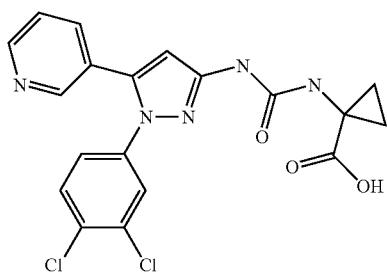 |

TABLE 1-continued
| | |
|---|---|
| 1146 | 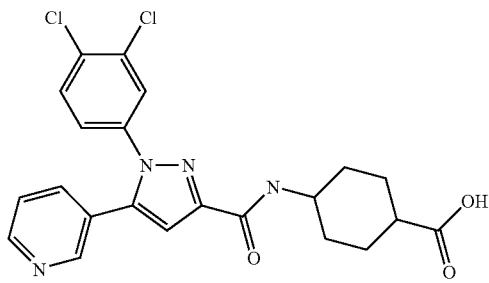 |
| 1147 | 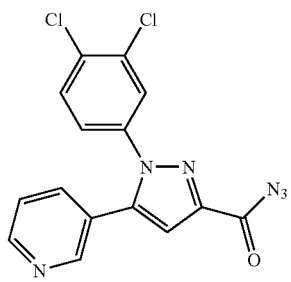 |
| 1148 | 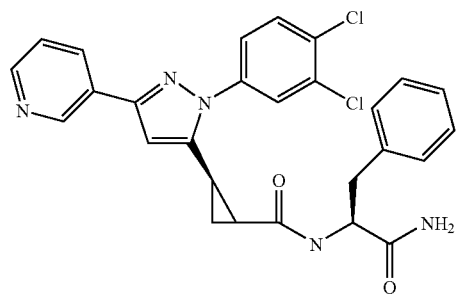 |
| 1149 | 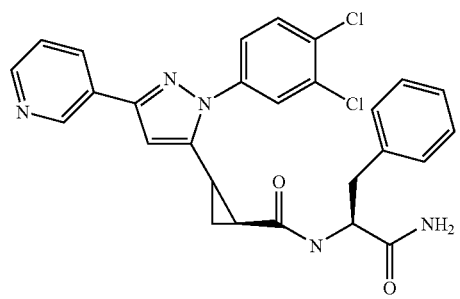 |
| 1150 | 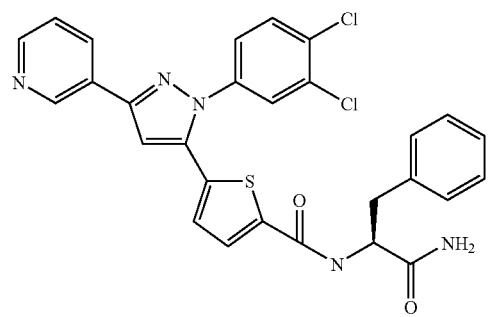 |

TABLE 1-continued
1151 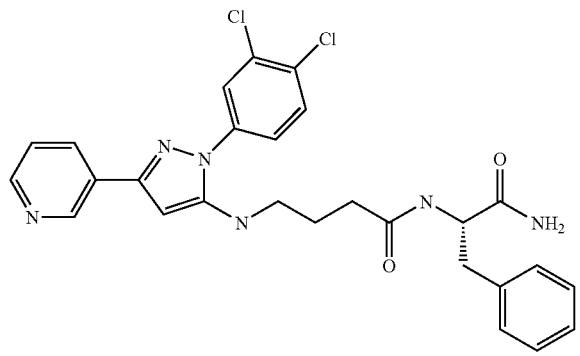
1152 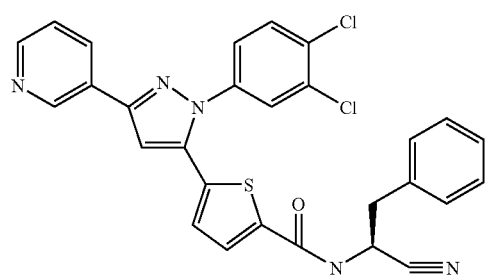
1153 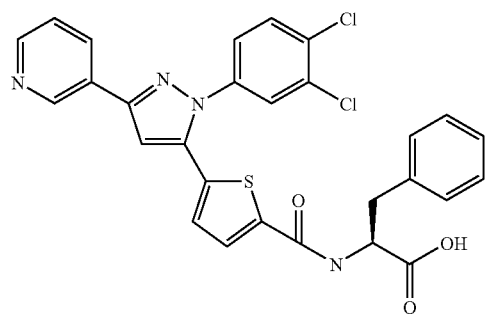
1154 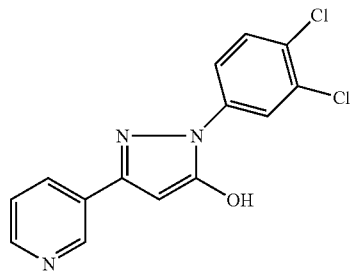
1155 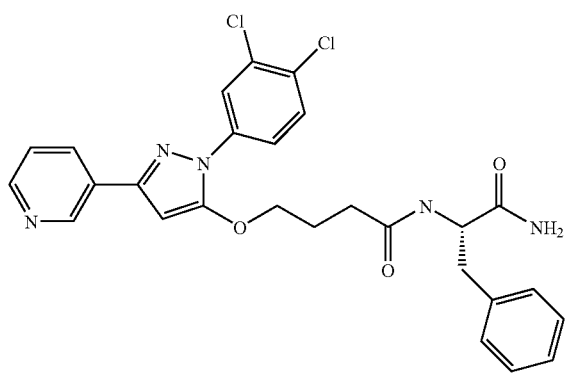

TABLE 1-continued
| 1156 | 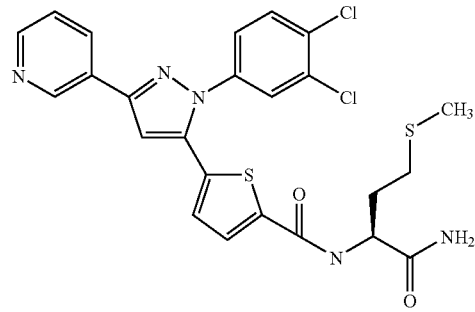 |
| --- | --- |
| 1157 | 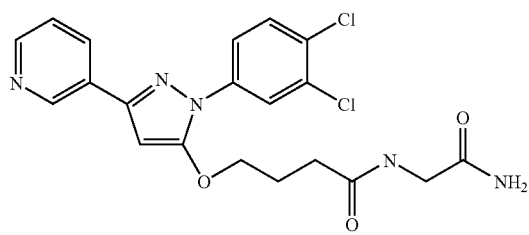 |
| 1158 | 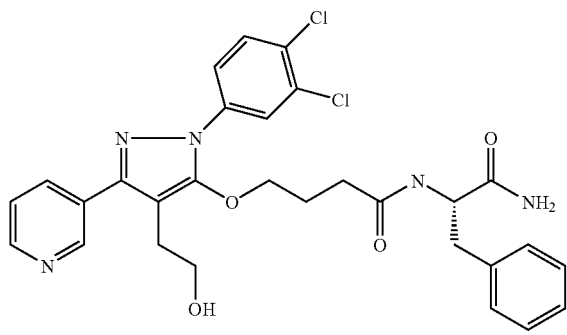 |
| 1159 | 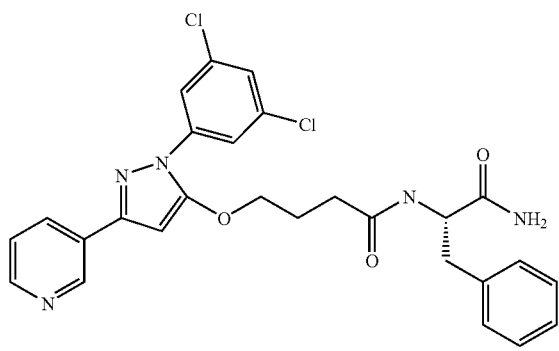 |
| 1160 | 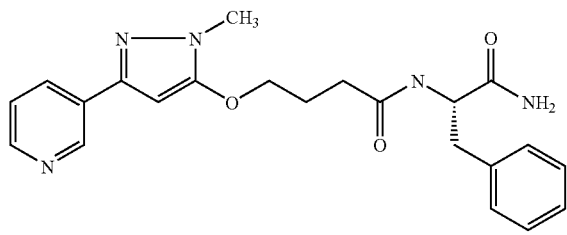 |

TABLE 1-continued
1161 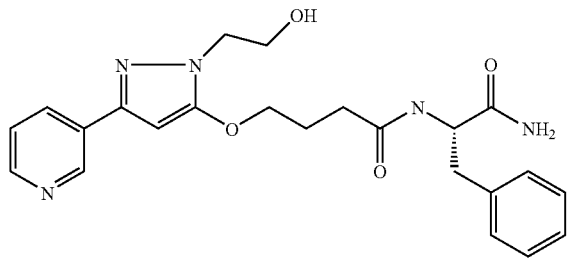
1162 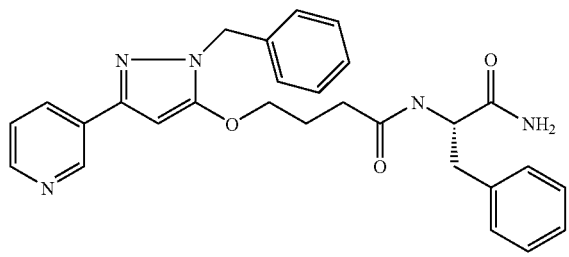
1163 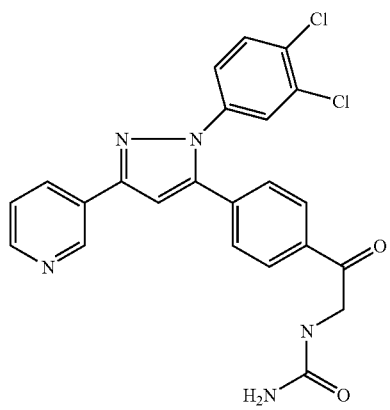
1164 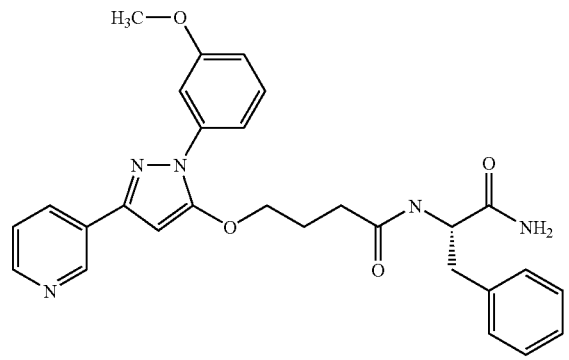
1165 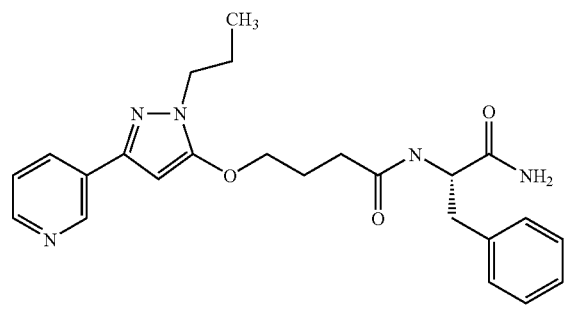

TABLE 1-continued
1166
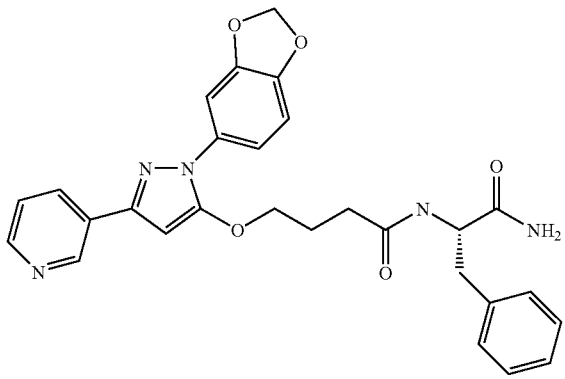
1167
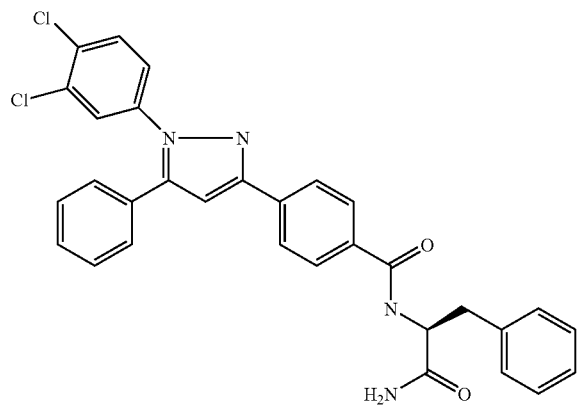
1168
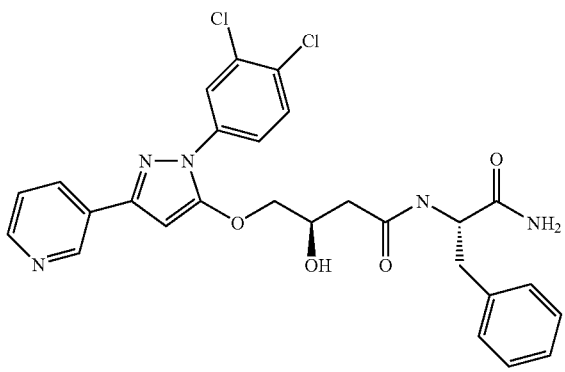
1169
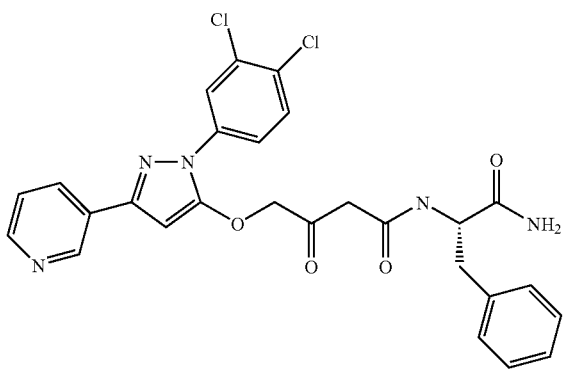

TABLE 1-continued
1170 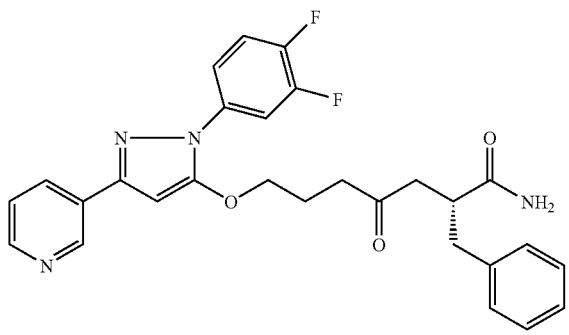
1171 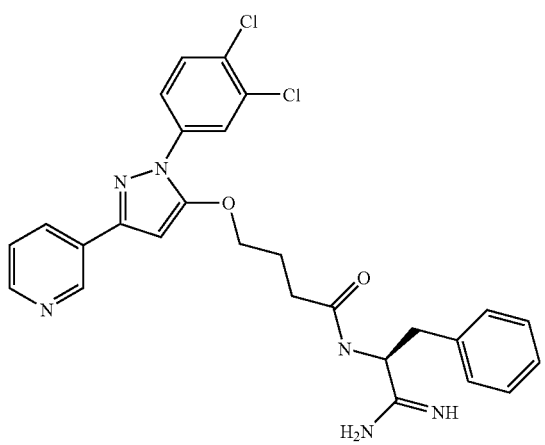
1172 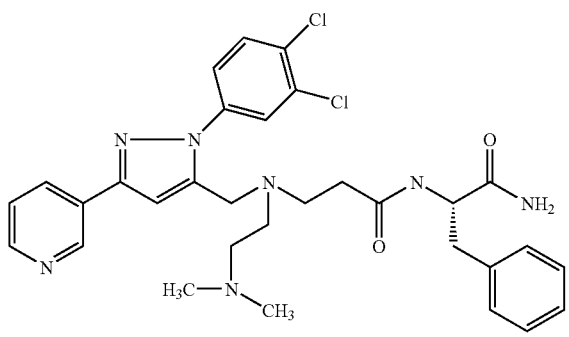
1173 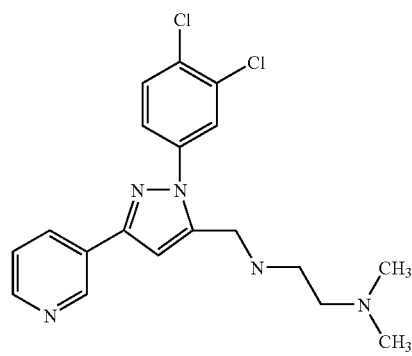

TABLE 1-continued
1174
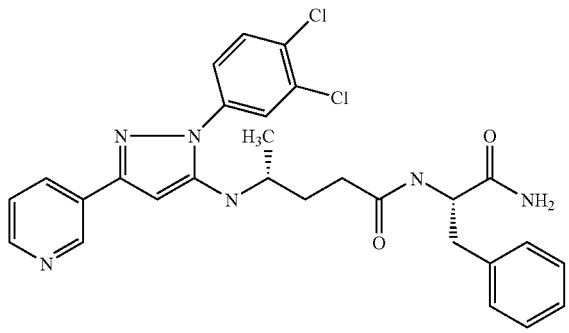
1175
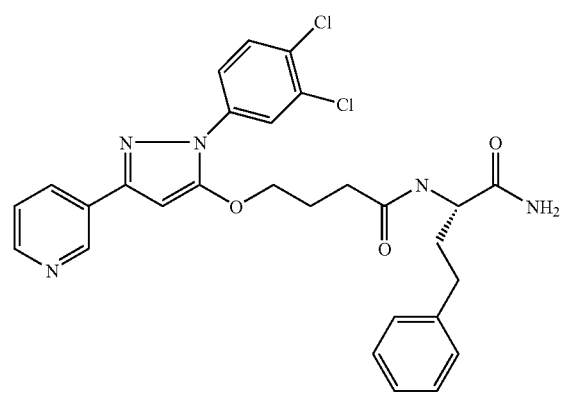
1176
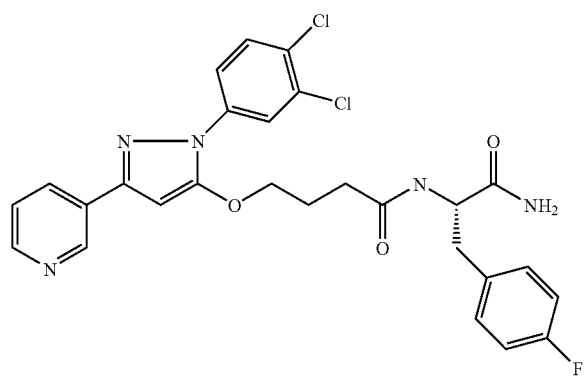
1177
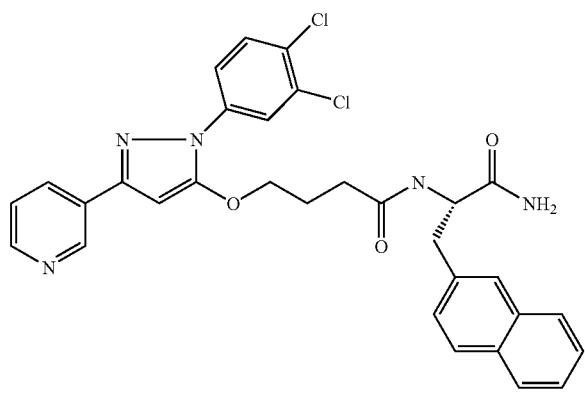

TABLE 1-continued
| 1178 | 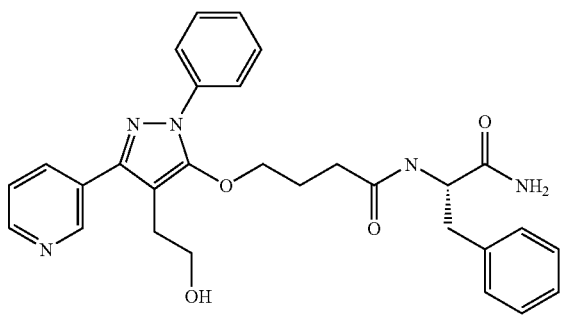 |
| --- | --- |
| 1179 | 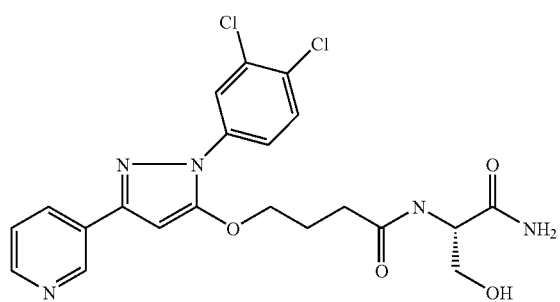 |
| 1180 | 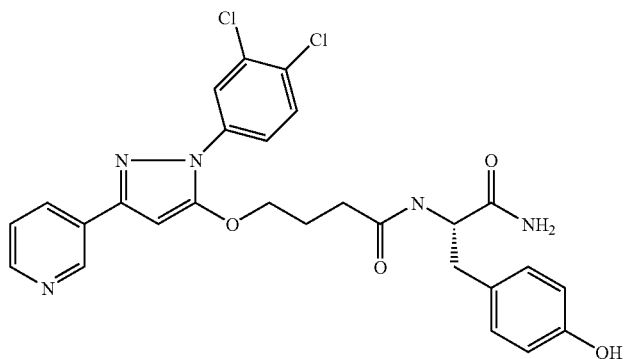 |
| 1181 | 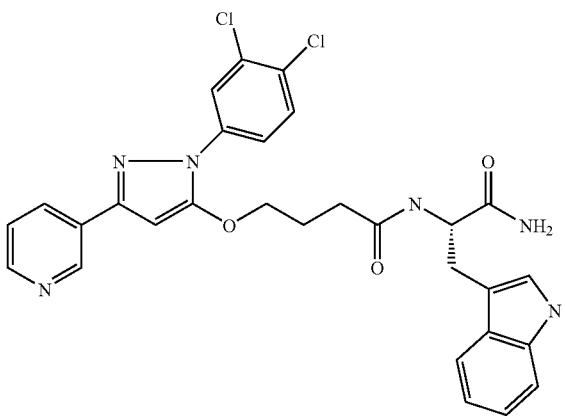 |

TABLE 1-continued
1182 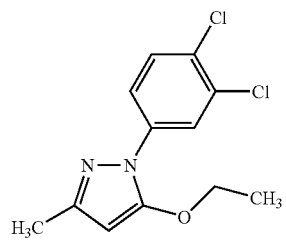
1183 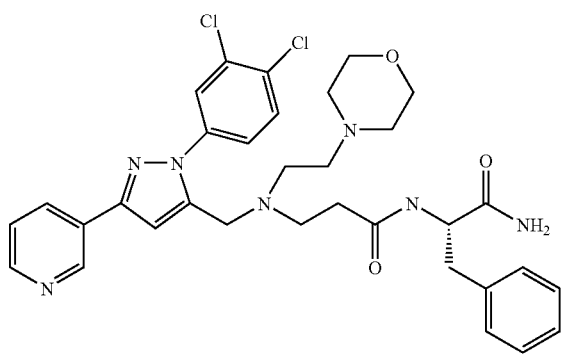
1184 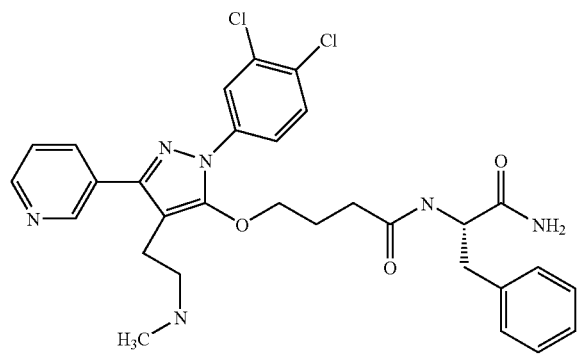
1185 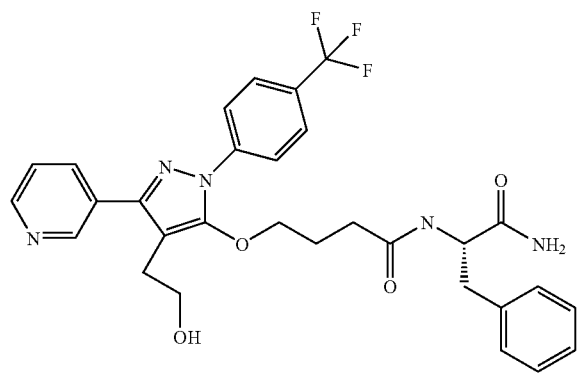

TABLE 1-continued
1186
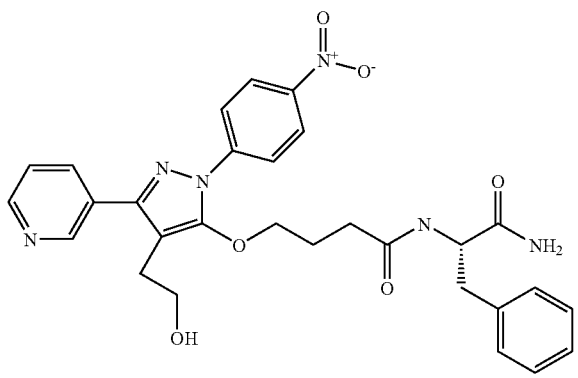
1187
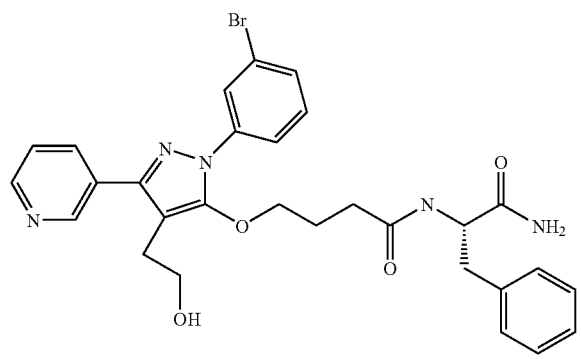
1188
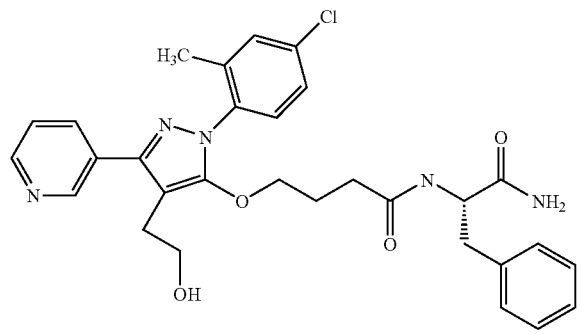
1189
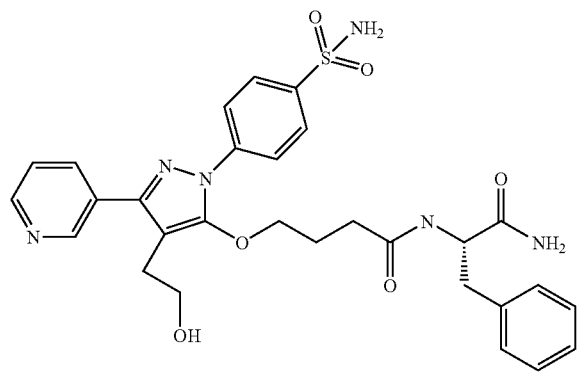

TABLE 1-continued
1190
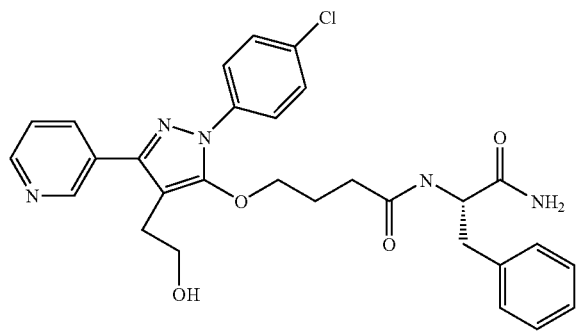
1191
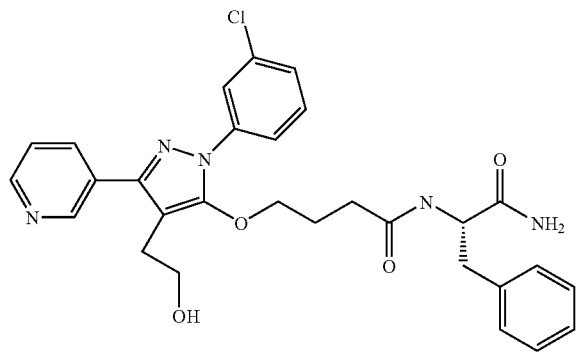
1192
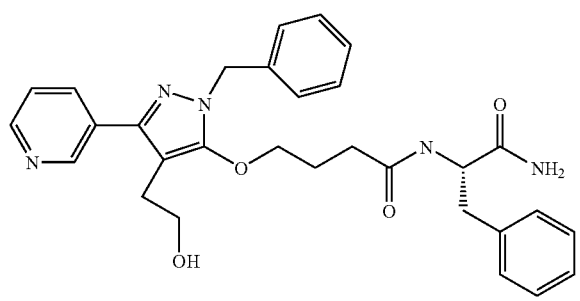
1193
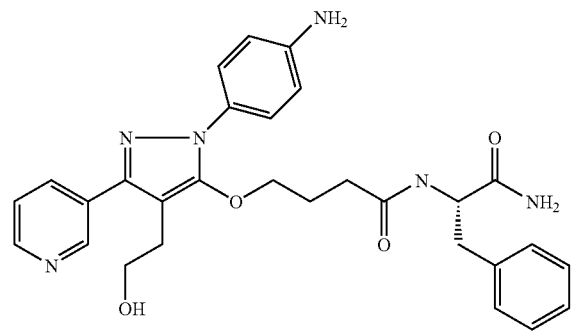

TABLE 1-continued
| 1194 | 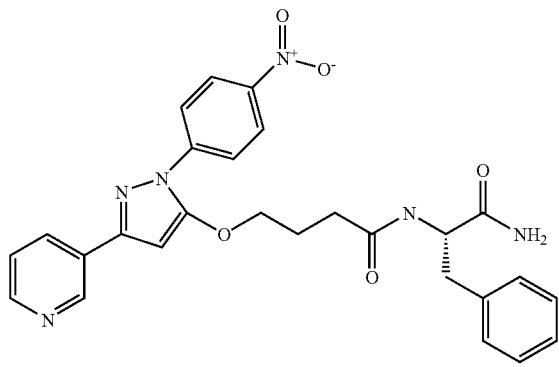 |
|---|---|
| 1195 | 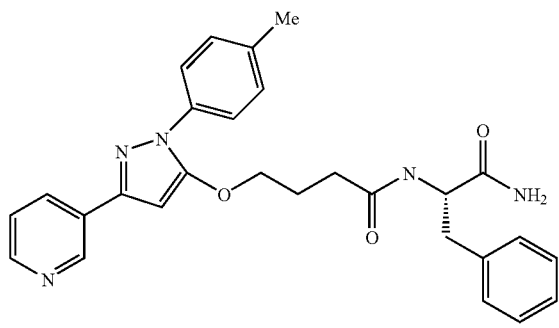 |
| 1196 | 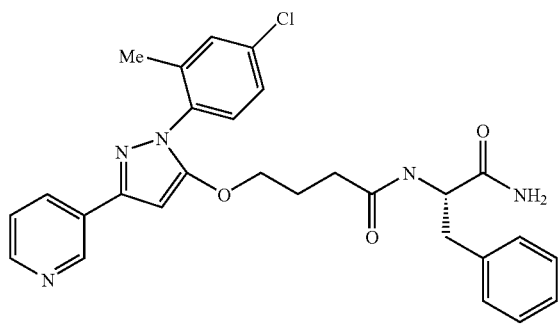 |
| 1197 | 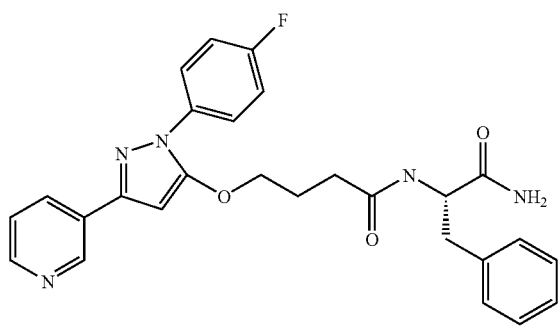 |

TABLE 1-continued
| 1198 | 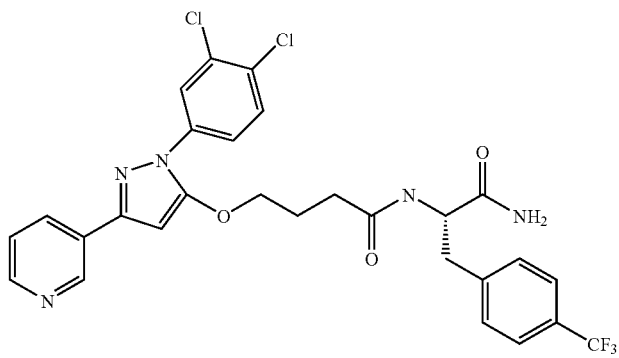 |
| --- | --- |
| 1199 | 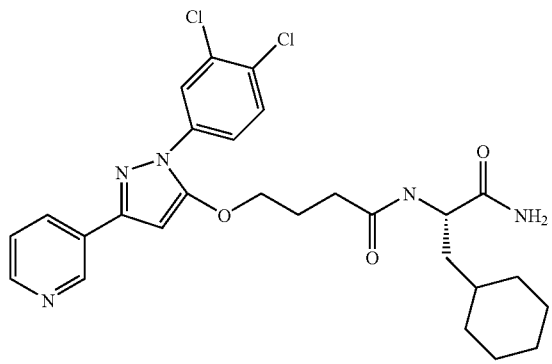 |
| 1200 | 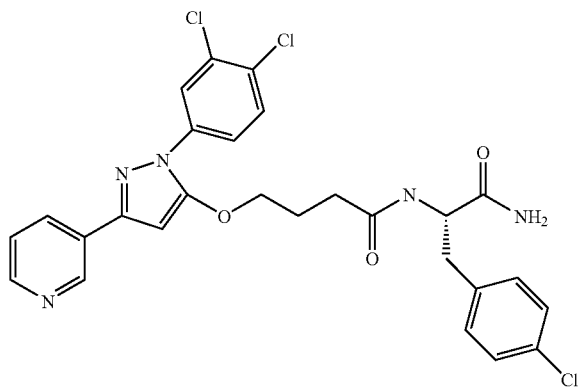 |
| 1201 | 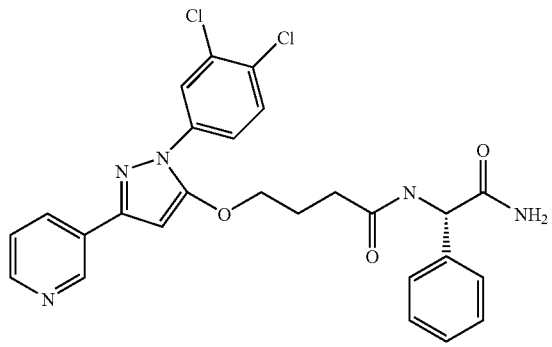 |

TABLE 1-continued
1202
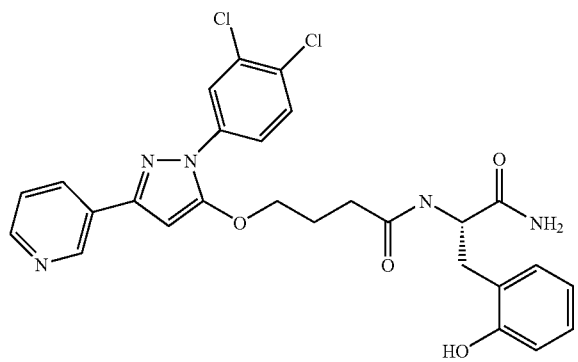
1203
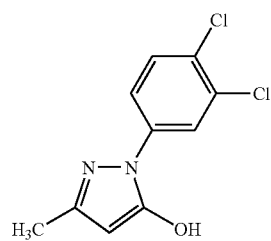
1204
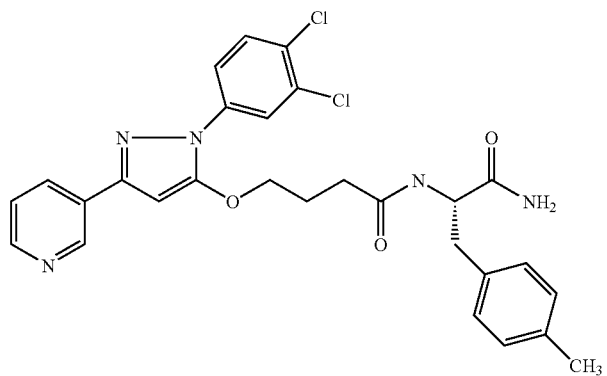
1205
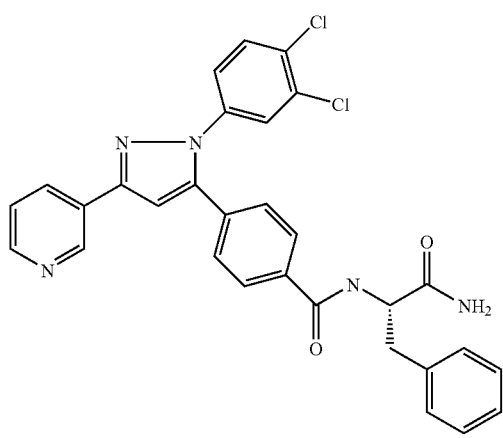

TABLE 1-continued
1206
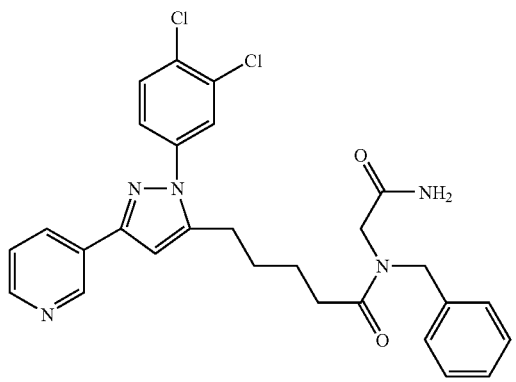
1207
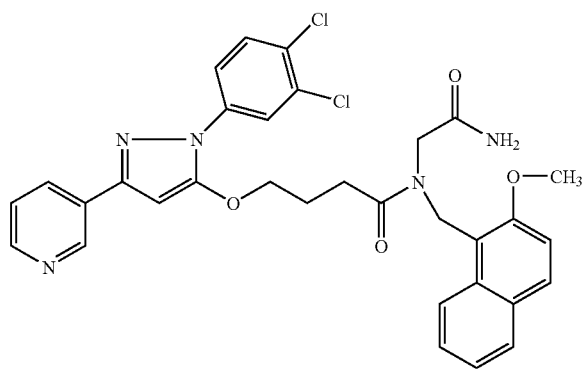
1208
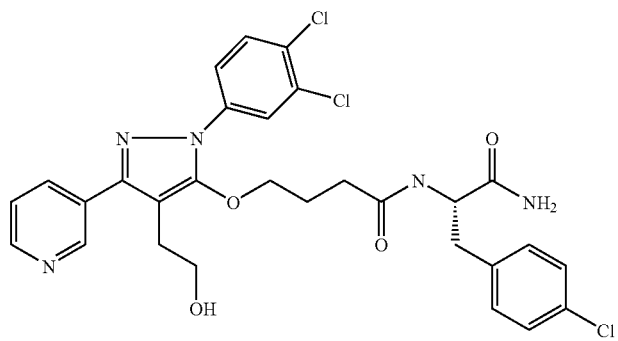
1209
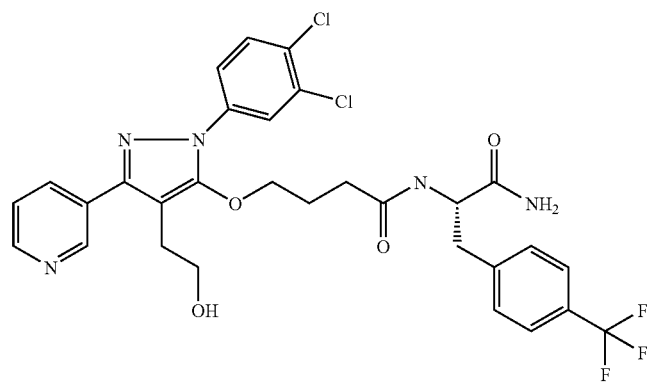

TABLE 1-continued
1210
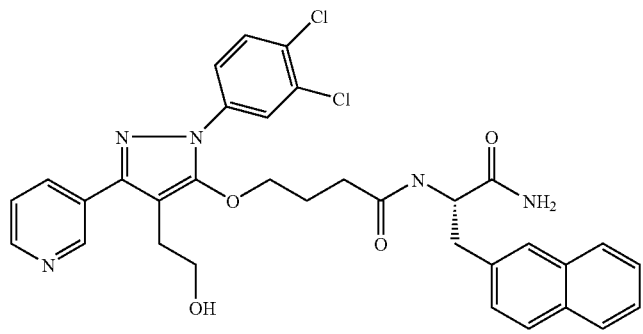
1211
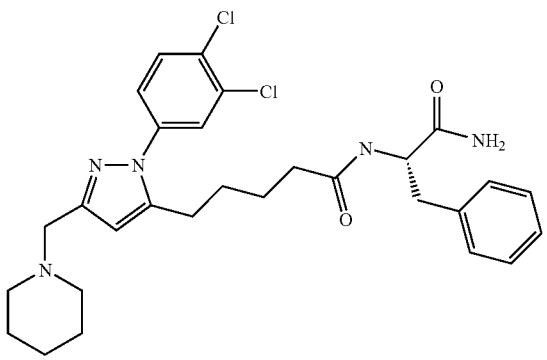
1212
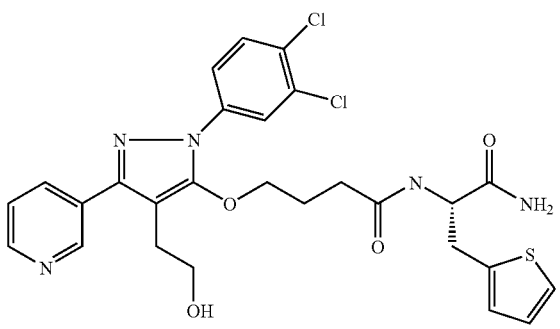
1213
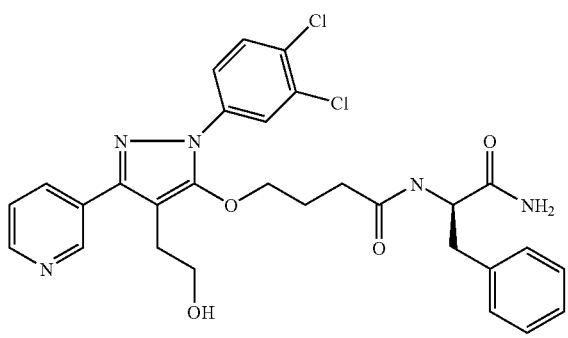

TABLE 1-continued
1214 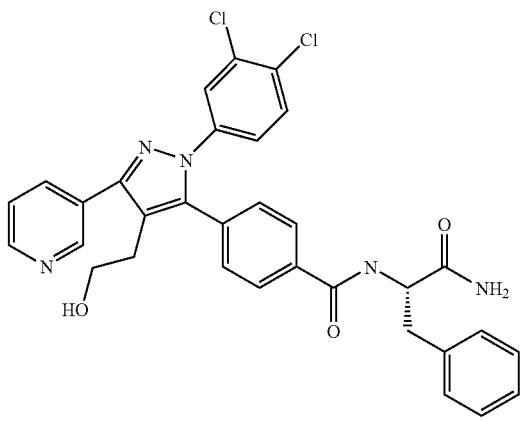
1215 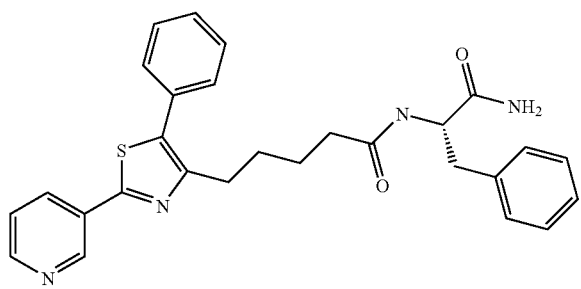
1216 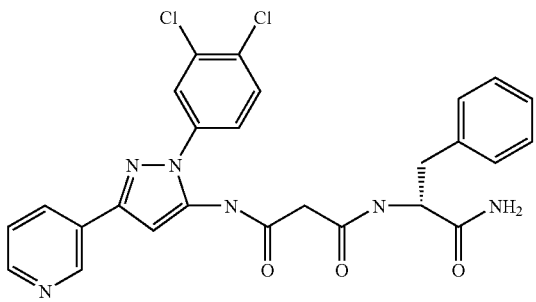
1217 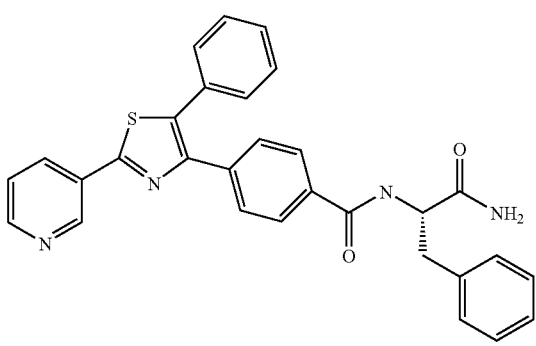

TABLE 1-continued
| 1218 | 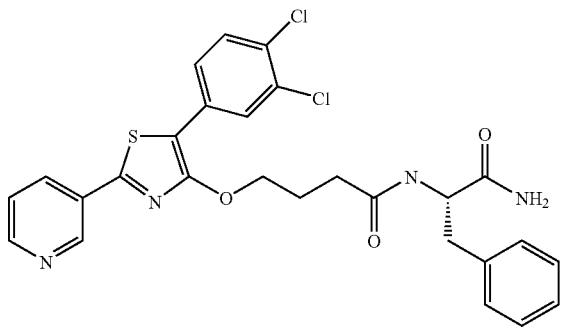 |
| 1219 | 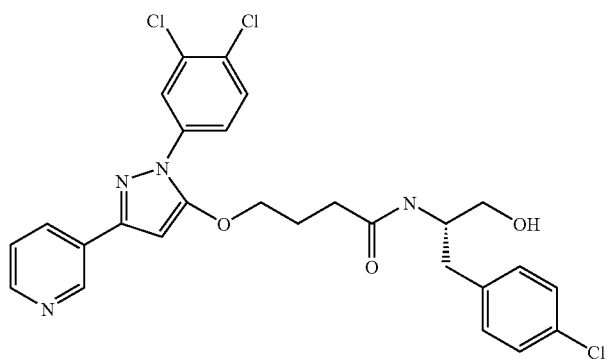 |
| 1220 | 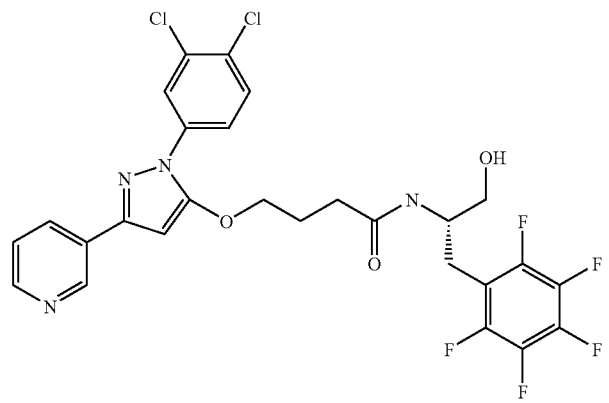 |
| 1221 | 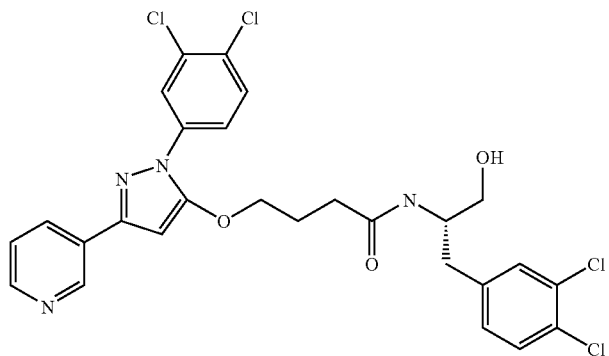 |

TABLE 1-continued
1222
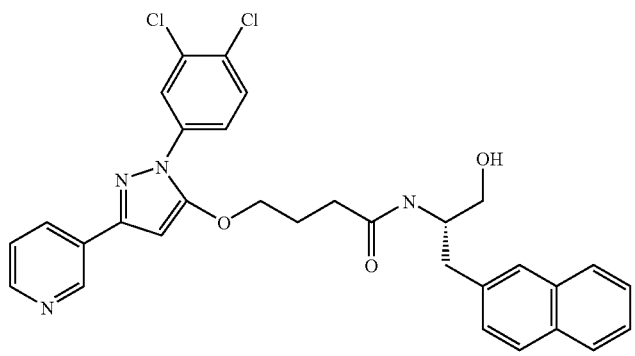
1223
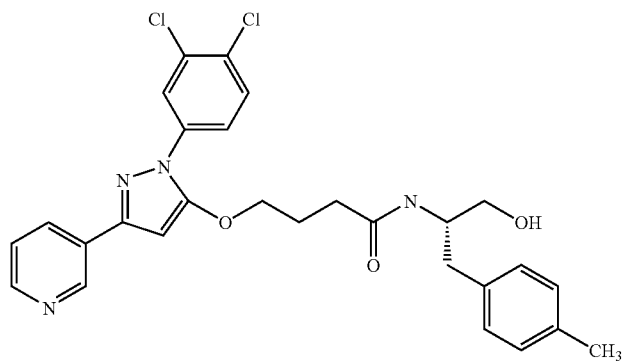
1224
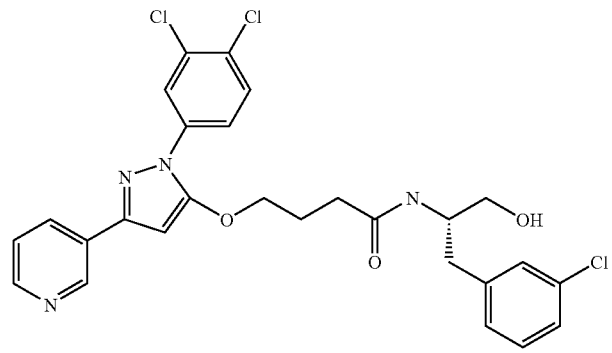
1225
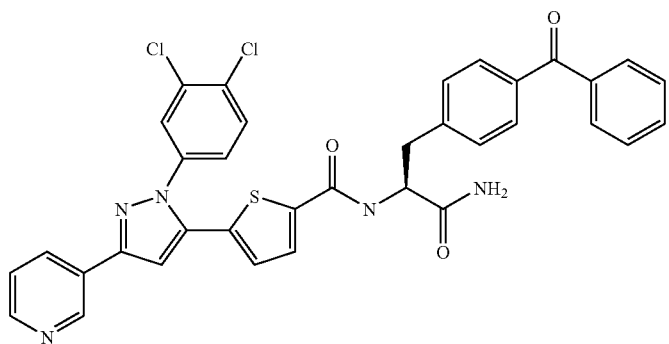

TABLE 1-continued
1226 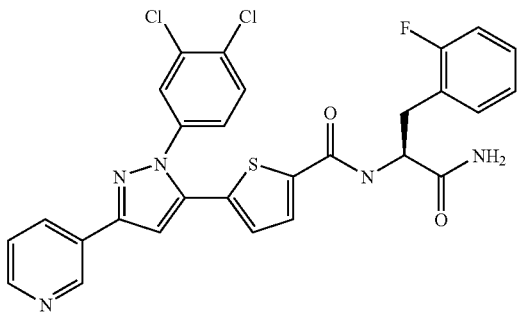
1227 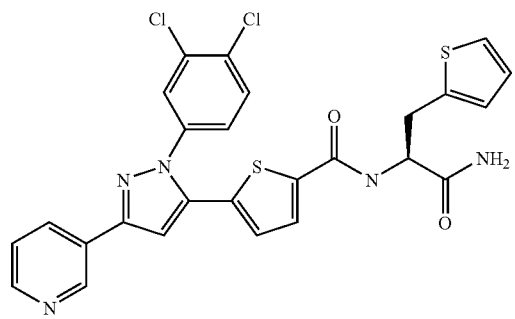
1228 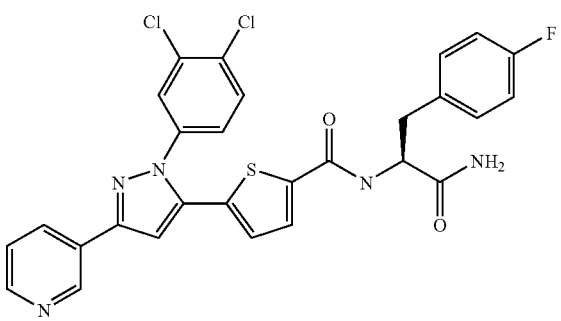
1229 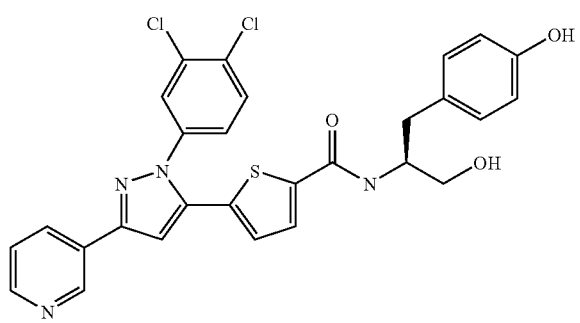
1230 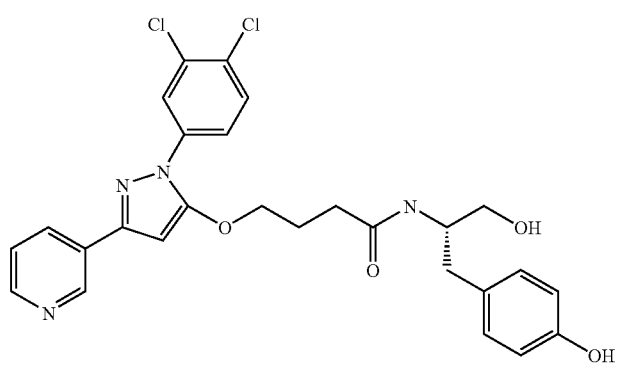

TABLE 1-continued
1231 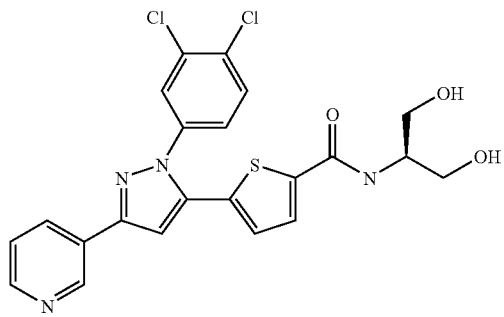
1232 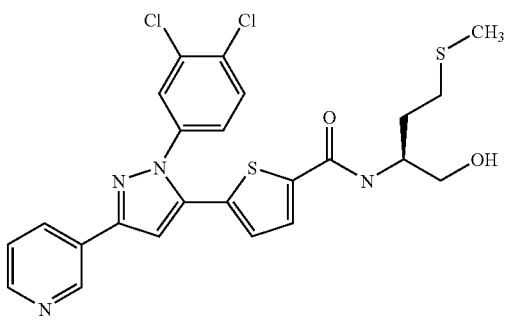
1233 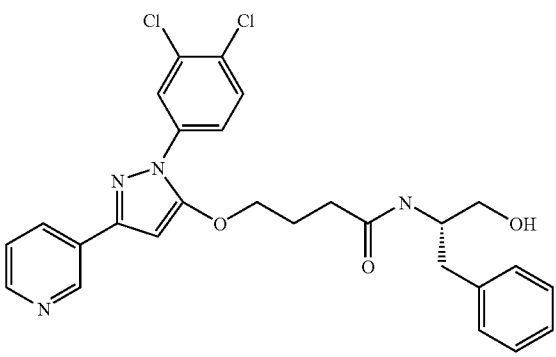
1234 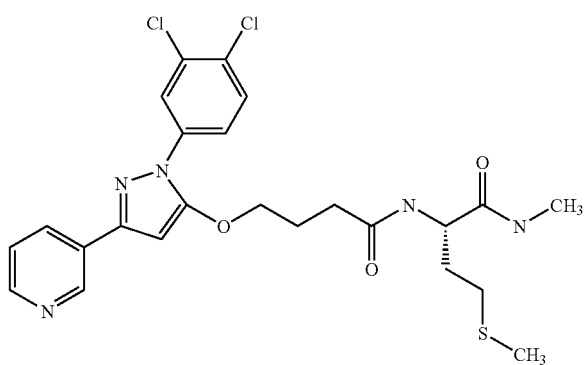

TABLE 1-continued
1235 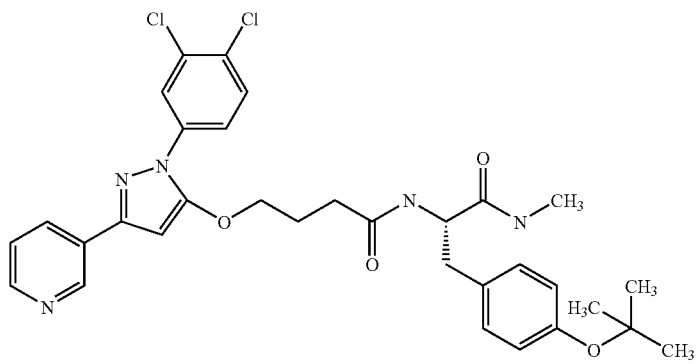
1236 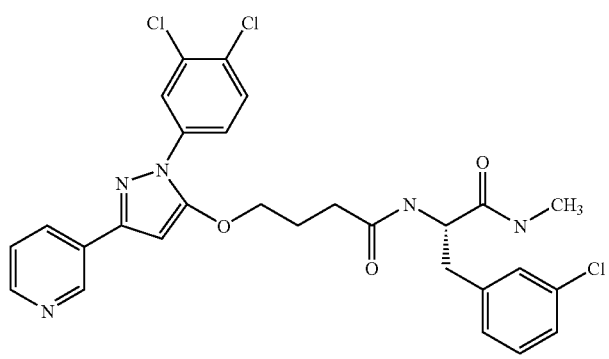
1237 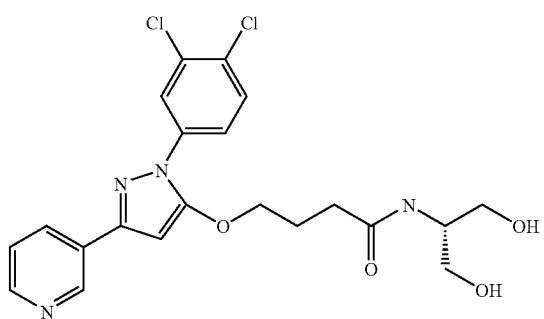
1238 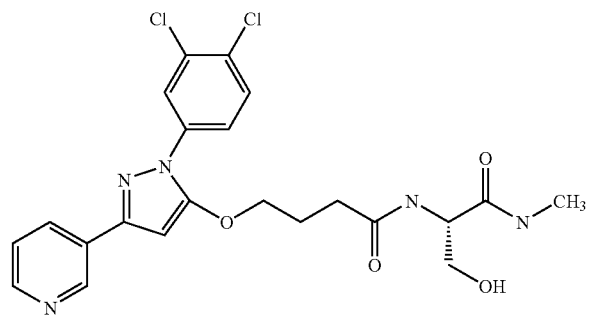

TABLE 1-continued
1239 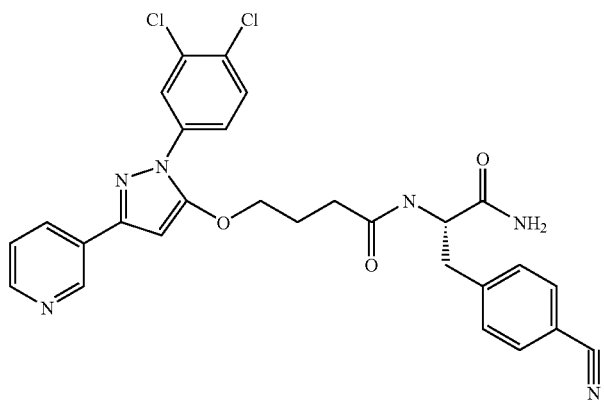
1240 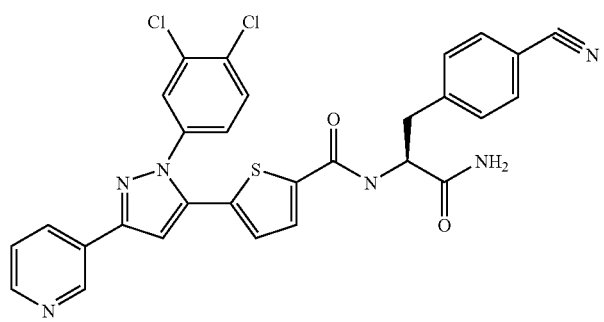
1241 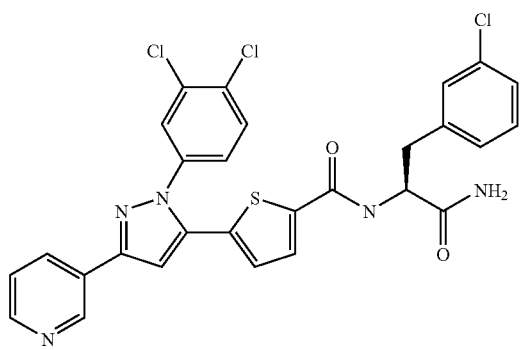
1242 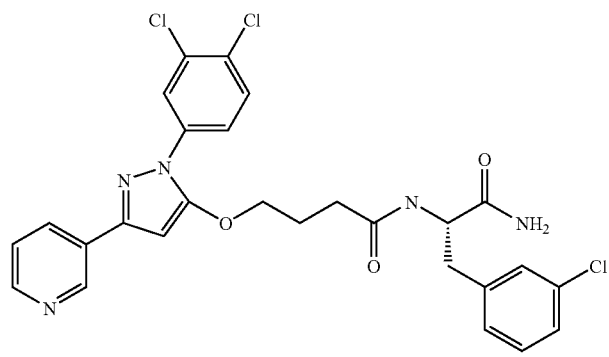

TABLE 1-continued
| 1243 | 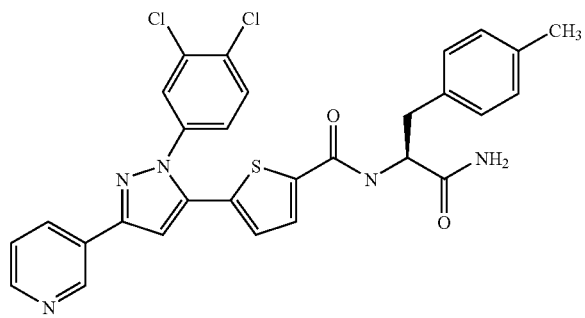 |
| 1244 | 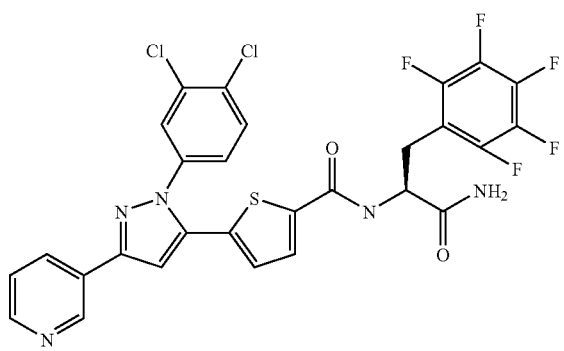 |
| 1245 | 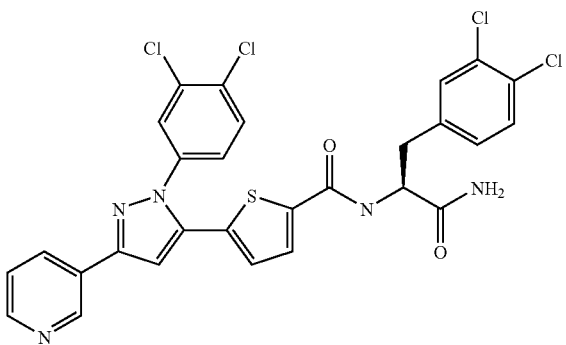 |
| 1246 | 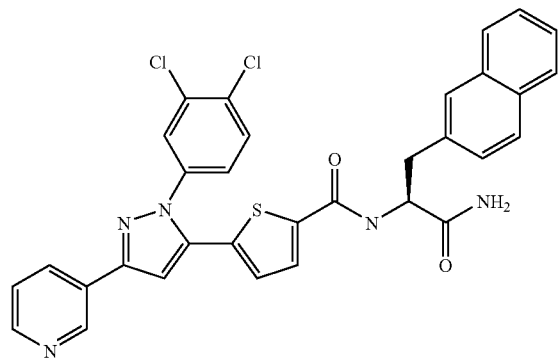 |

TABLE 1-continued
| 1247 | 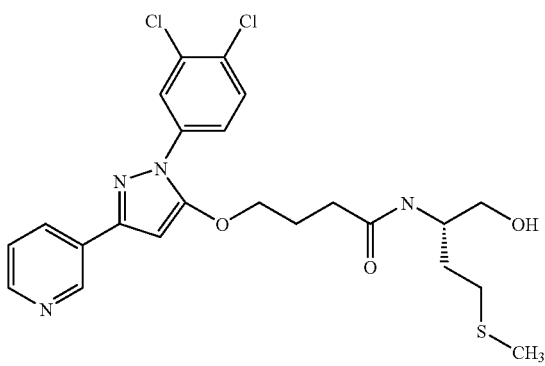 |
| 1248 | 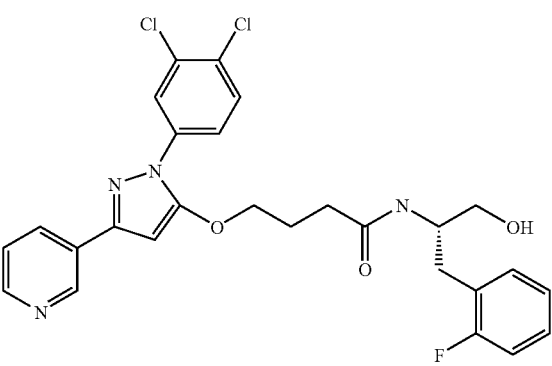 |
| 1249 | 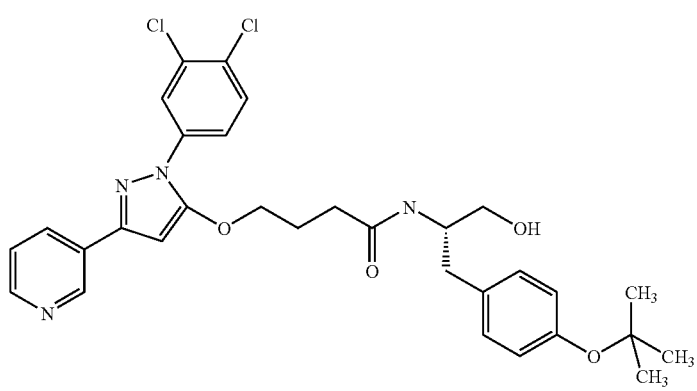 |
| 1250 | 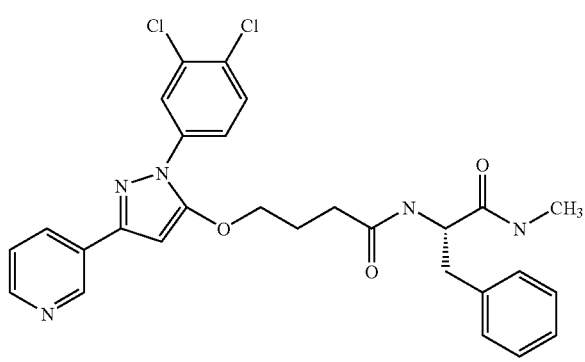 |

TABLE 1-continued
1251 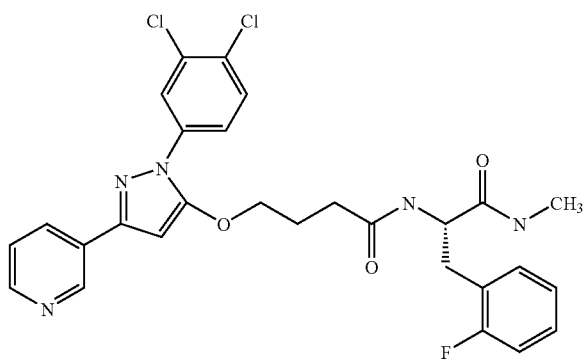
1252 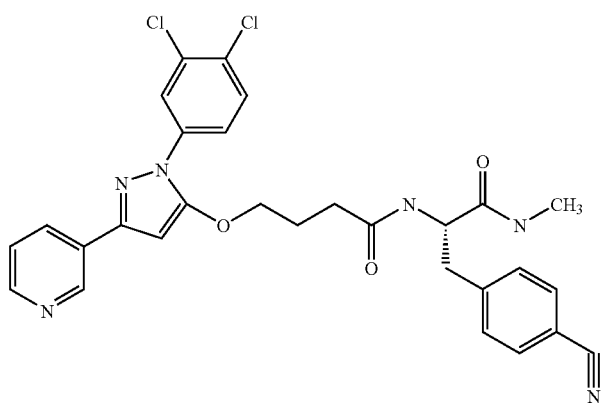
1253 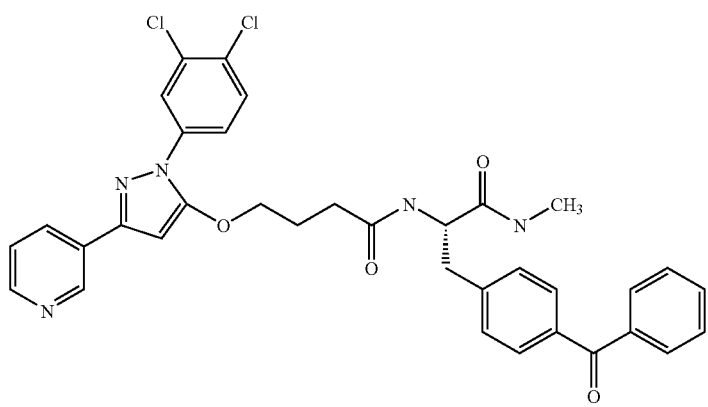
1254 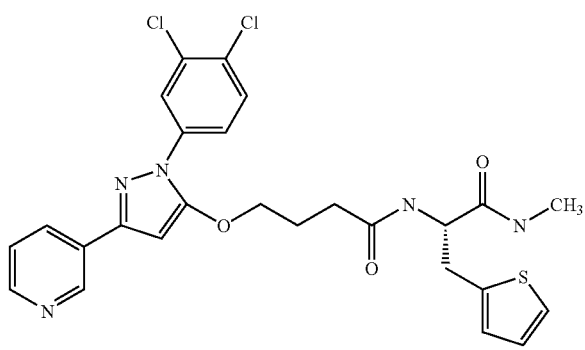

TABLE 1-continued
1255
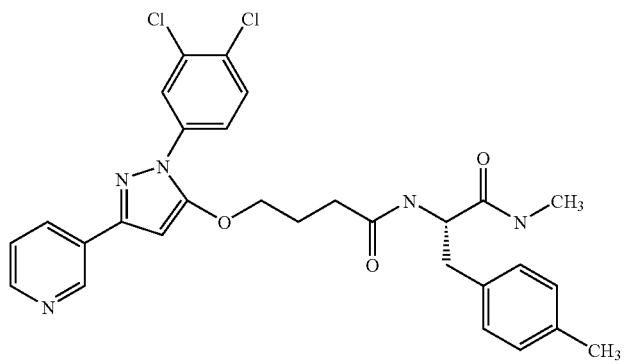
1256
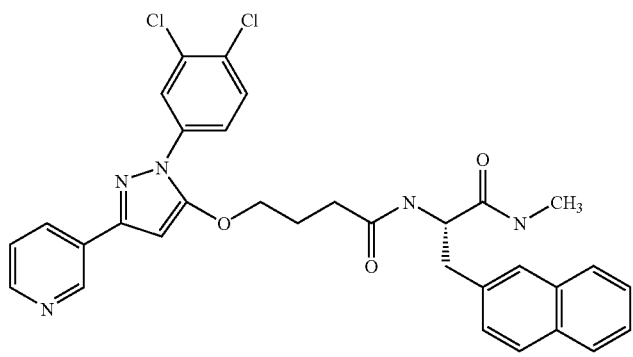
1257
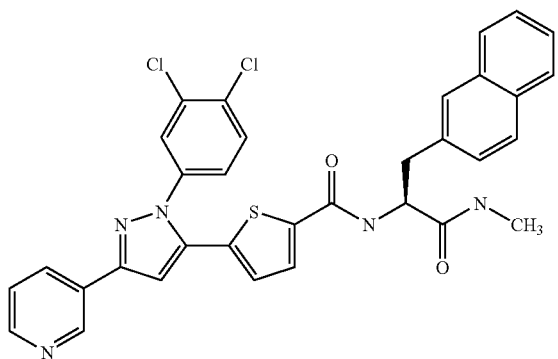
1258
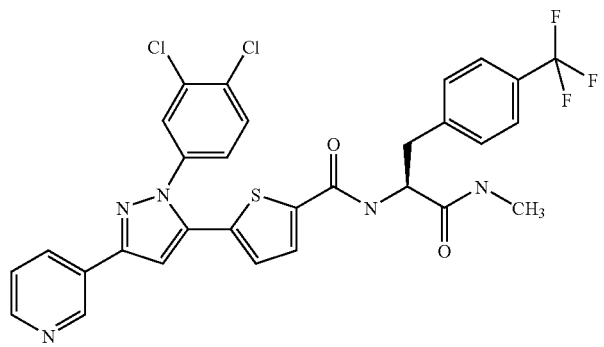

TABLE 1-continued
1259 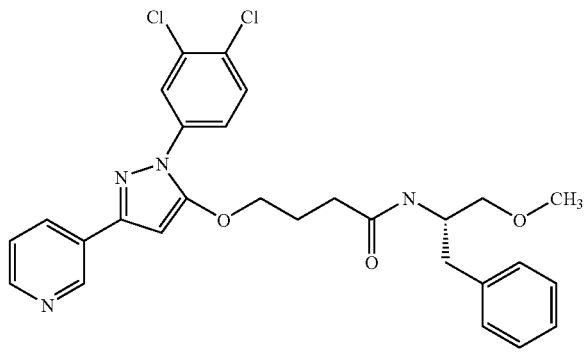
1260 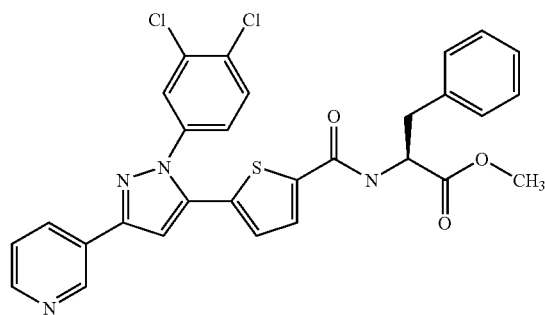
1261 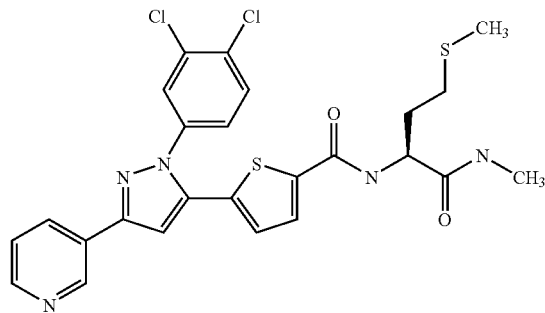
1262 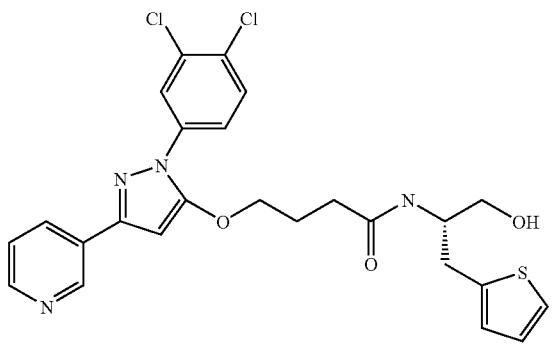

TABLE 1-continued
1263
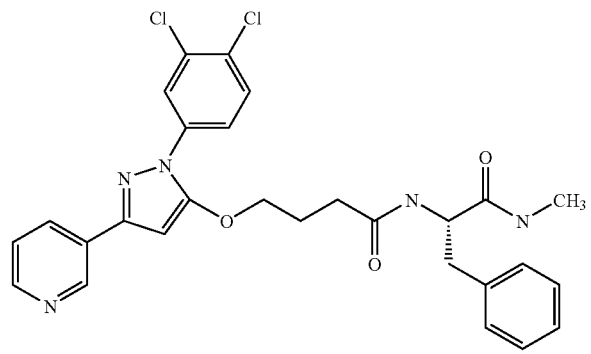
1264
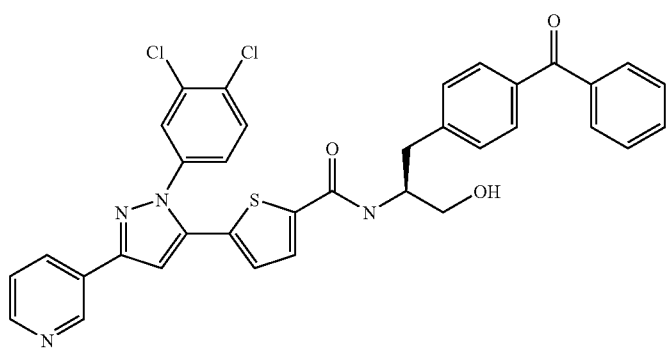
1265
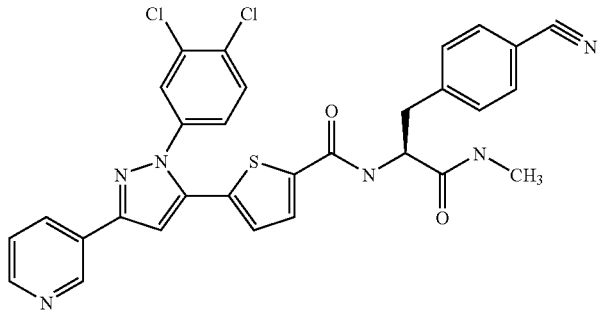
1266
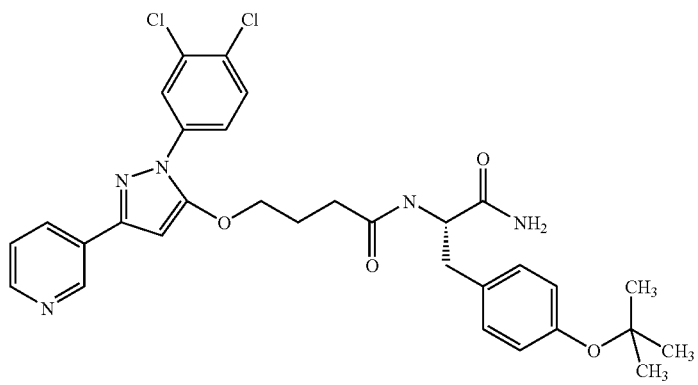

TABLE 1-continued
1267
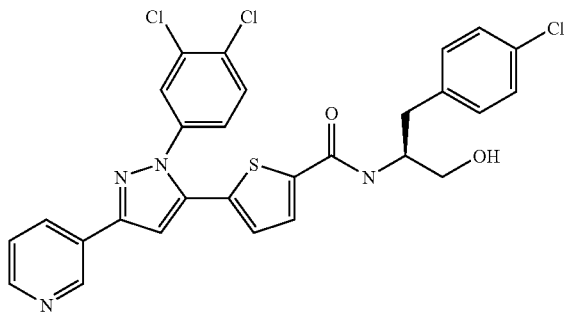
1268
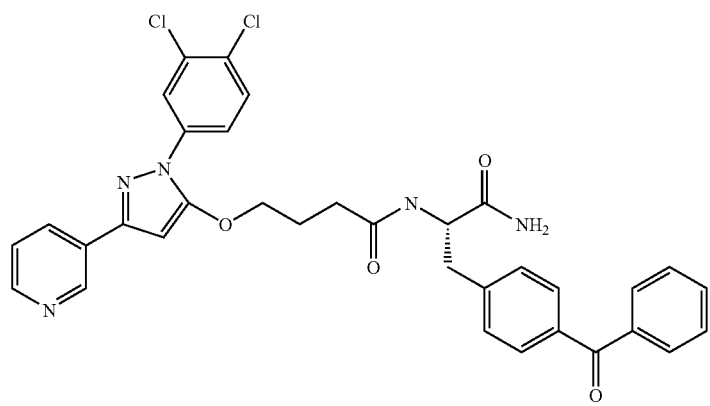
1269
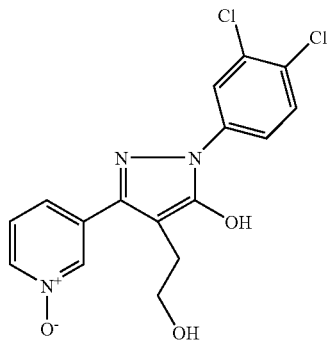
1270
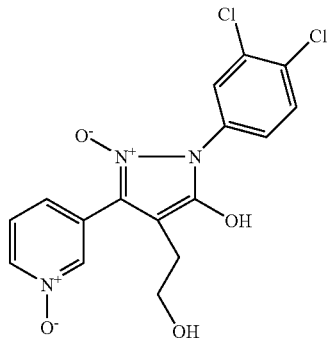

TABLE 1-continued
1271 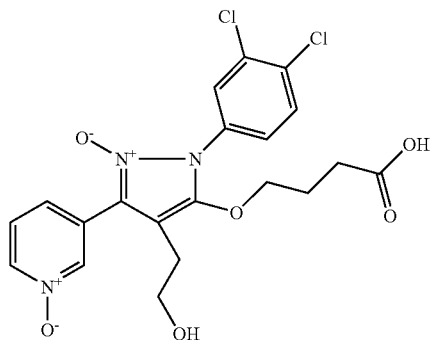
1272 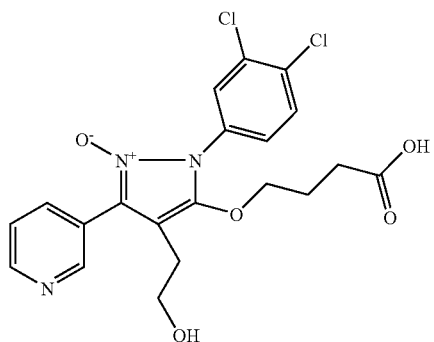
1273 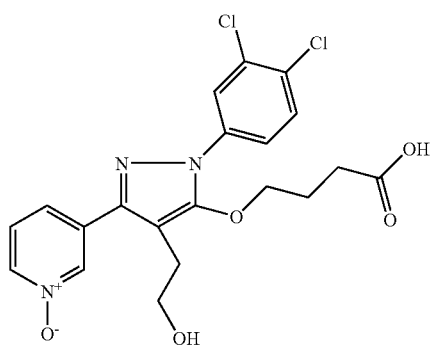
1274 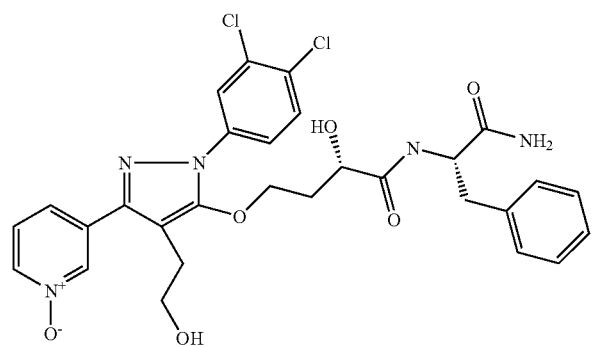

TABLE 1-continued

1275

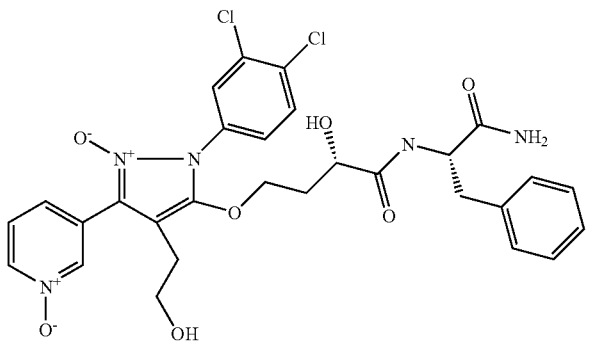

1276

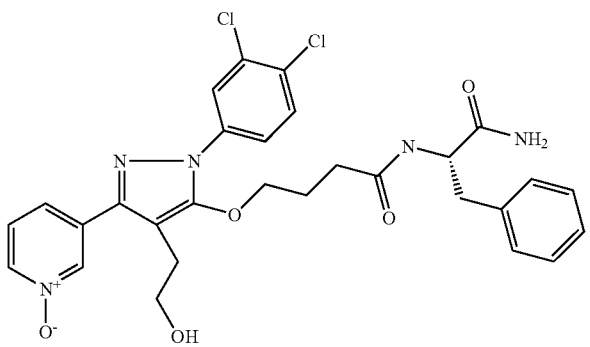

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in *Protective Groups in Organic Synthesis*, 2nd edition, T. H. Greene and P. G. M. Wuts, John Wiley & Sons, New York, N.Y., 1991, which is incorporated herein in its entirety by this reference. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents that are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

It will be appreciated by those skilled in the art that compounds of the invention having a chiral center may exist in and be isolated in optically active and racemic forms. It is to be understood that the present invention encompasses any racemic, optically-active, regioisomeric or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine prenylation inhibitor activity using the standard tests described herein, or using other similar tests which are well known in the art. It is also to be understood that the scope of this invention encompasses not only the various isomers which may exist but also the various mixtures of isomers which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.*, 1974, 96, 3642, which is incorporated herein in its entirety by this reference.

The compounds of the present invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids and bases are described above. In addition, hydrated, solvated and/or anhydrous forms of compounds disclosed herein are also encompassed in the present invention.

The compounds of present invention may be prepared by both conventional and solid phase synthetic techniques known to those skilled in the art. Useful conventional techniques include those disclosed by U.S. Pat. Nos. 5,569,769 and 5,242,940, and PCT publication No. WO 96/37476, each of which are incorporated herein in their entirety by this reference.

Combinatorial synthetic techniques, however, are particularly useful for the synthesis of the compounds of the present invention. See, e.g., Brown, *Contemporary Organic Synthesis*, 1997, 216; Felder and Poppinger, *Adv. Drug Res.*, 1997, 30, 111; Balkenhohl et al., *Angew. Chem. Int. Ed. Engl.*, 1996, 35, 2288; Hermkens et al., *Tetrahedron*, 1996, 52, 4527; Hermkens et al., *Tetrahedron*, 1997, 53, 5643; Thompson et al., *Chem. Rev.*, 1996, 96, 555; and Nefzi et al., *Chem. Rev.*, 1997, 2, 449-472.

One solid phase synthetic approach useful for preparing compounds of this invention is described by Marzinzik and Felder, *Tetrahedron Lett.*, 1996, 37, 1003-1006, and Marzinzik and Felder, *J. Org. Chem.*, 1998, 63, 723-727. A general adaptation of this approach is shown in the synthetic scheme of FIG. 1. Referring to FIG. 1, <A>, <B>, <C> and <D> represent reaction conditions suitable for the formation of the desired products or intermediates represented by Formulas (a)-(d); W, X, Y and Z constitute moieties within the compounds of the present invention as defined above, and R is a halogenated phenyl.

As shown in FIG. 1, an appropriate compound is attached to a resin or other solid support under reaction conditions <A> to form a complex of Formula (a). Appropriate reaction conditions and solid supports are well known to those skilled in the art. The immobilized compound of Formula (a) is then combined with a suitable reactant comprising the moieties R and Z to yield a compound of Formula (b). Suitable reactants for the formation of the compound of Formula (b) include, for example, keto acids and the like, and depend upon the nature of the leaving group L and reaction conditions <B>. Suitable reactants and reaction conditions are well known to those skilled in the art. See, e.g., March, *Advanced Organic Chemistry* 3$^{rd}$ ed., John Wiley & Sons, Inc., New York, N.Y., 1985, pp. 435-437, which is incorporated herein by reference.

According to FIG. 1, the immobilized compound of Formula (b) is then subjected to reaction conditions <C> to form the pyrazole compound of Formula (c), wherein R is typically as defined above, or a precursor thereto. Reaction conditions <C> are also well known to one of ordinary skill in the art. See, e.g., March, *Advanced Organic Chemistry* 3$^{rd}$ ed., John Wiley & Sons, Inc., New York, N.Y., 1985, p. 804, which is incorporated herein by this reference.

Finally, the compound of Formula (c) is cleaved from the resin under reaction conditions <D> that are well known to those skilled in the art to yield the final product of Formula (d) which, if desired, may undergo purification, crystallization or recrystallization, or further reactions to form compounds of this invention.

Figure 2:
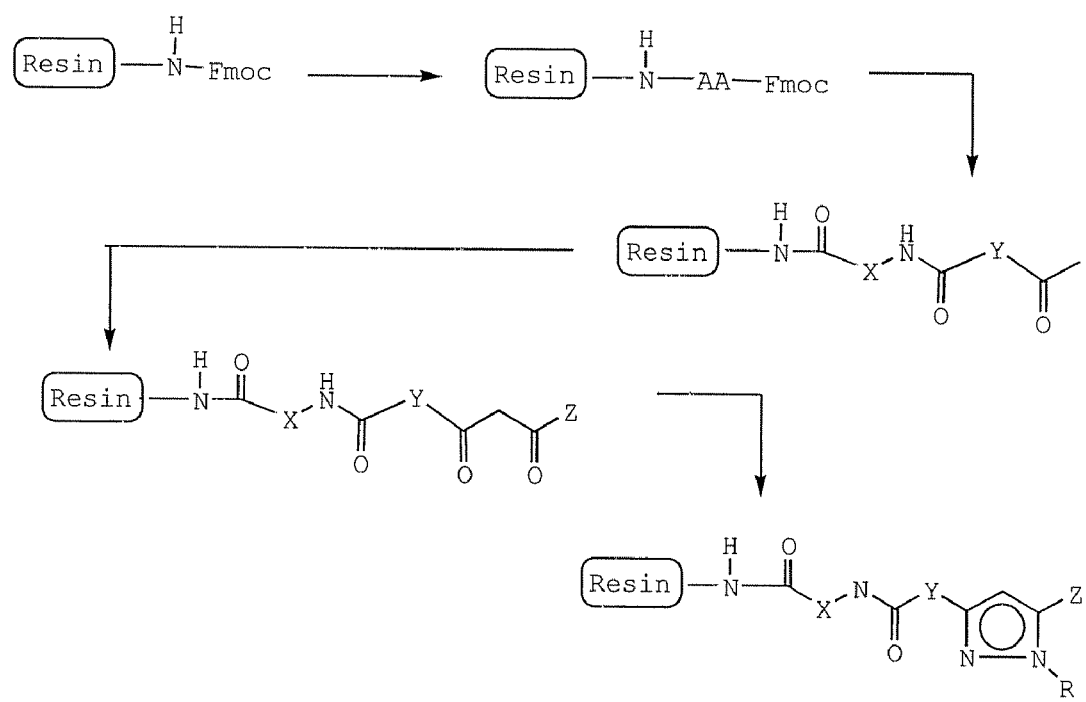
FIG. 2 illustrates a specific embodiment of the general synthetic approach for the production of prenylation inhibitors shown in FIG. 1.

A particular embodiment of this approach is presented in the synthesis scheme shown in FIG. 2 where AA is a natural or synthetic amino acid, and X, Y, Z and R are those defined above.

In the first step of the scheme of FIG. 2, the protected amine groups bound to the resin are deprotected and reacted with a protected natural or synthetic amino acid under suitable conditions. Although both the resin-bound amine and the amino acid moiety in FIG. 2 are protected with Fmoc, other protecting groups well known to those skilled in the art may also be used. See, for example, *Protective Groups in Organic Synthesis*, 2nd edition, T. H. Greene and P. G. M. Wuts, John Wiley & Sons, New York, N.Y., 1991, which is incorporated in its entirety by this reference.

Removal of the amino acid protecting group and reacting the resulting free amine with a keto acid affords the methyl ketone compound shown in FIG. 2. The third step of FIG. 2 can be carried out using any of the methods known to those of ordinary skill in the art of organic chemistry, including a Claisen condensation reaction. The conditions most suitable for this reaction may be determined using compounds such as ethyl benzoate, such optimization may be necessary in some cases to ensure that the reaction occurs without appreciable formation of side products. This reaction is preferably done using dimethylacetamide (DMA) as a solvent.

The fourth step involves formation of the pyrazole ring moiety, for example, by reacting the 1,3-diketone with an appropriately substituted hydrazine. The final products may be cleaved from the solid-support by conventional means.

Figure 3:
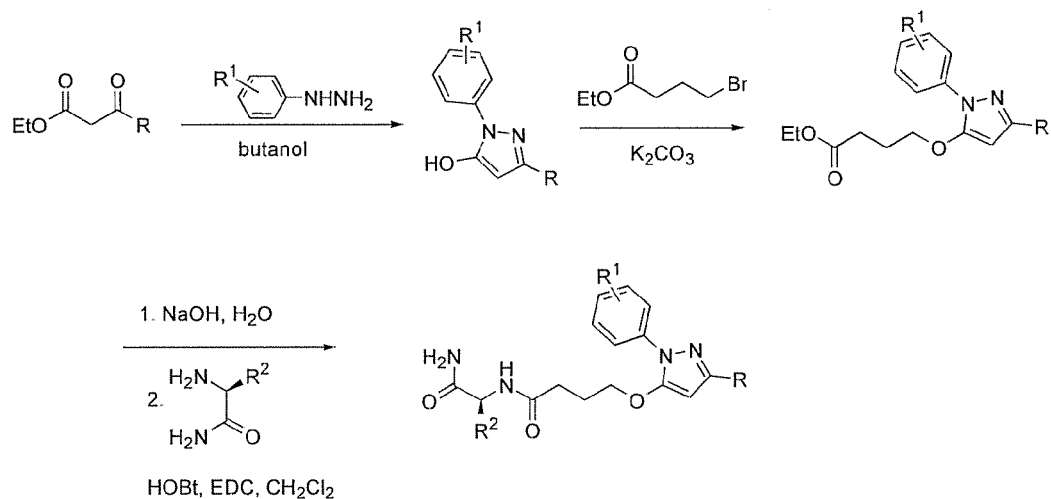
FIG. 3 illustrates a synthetic scheme for the production of an ether group that links a central aromatic ring having two heteroatoms to an amide group that may be further substituted to form prenylation inhibitor compounds of the present invention.
Figure 4:
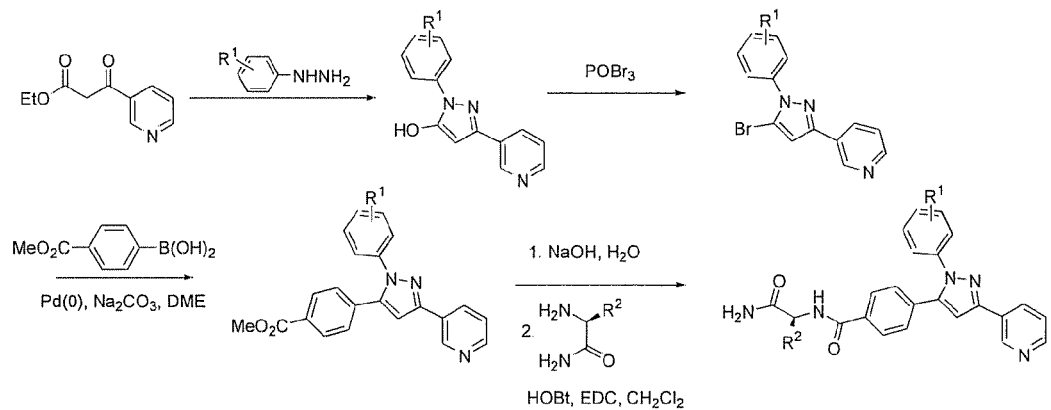
FIG. 4 illustrates a synthetic scheme for the production of a phenyl group that links a central aromatic ring having two heteroatoms to an amide group that may be further substituted to form prenylation inhibitor compounds of the present invention.
Figure 5:
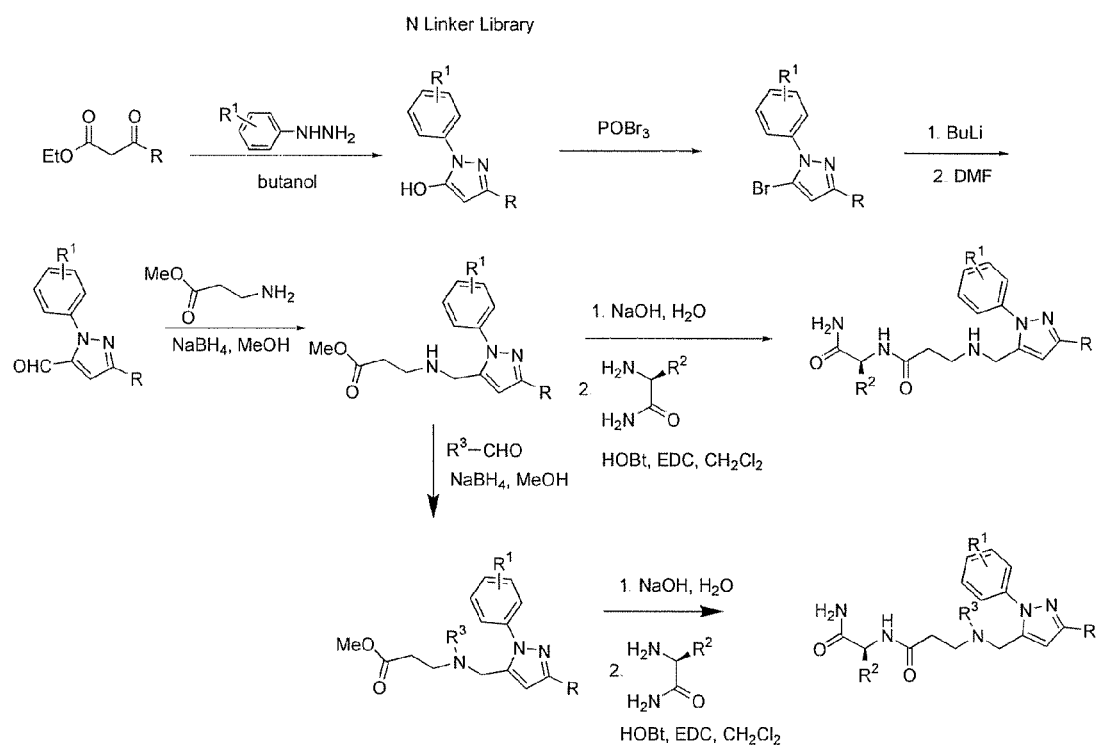
FIG. 5 illustrates a synthetic scheme for the production of an amine group that links a central aromatic ring having two heteroatoms to an amide group that may be further substituted to form prenylation inhibitor compounds of the present invention.

FIGS. 3, 4 and 5 show synthetic schemes for the production of ether, aromatic and amine groups, respectively, that link the aromatic ring having two or three heteroatoms to an amide group that may be further substituted to form prenylation inhibitor compounds of the present invention.

Figure 6:
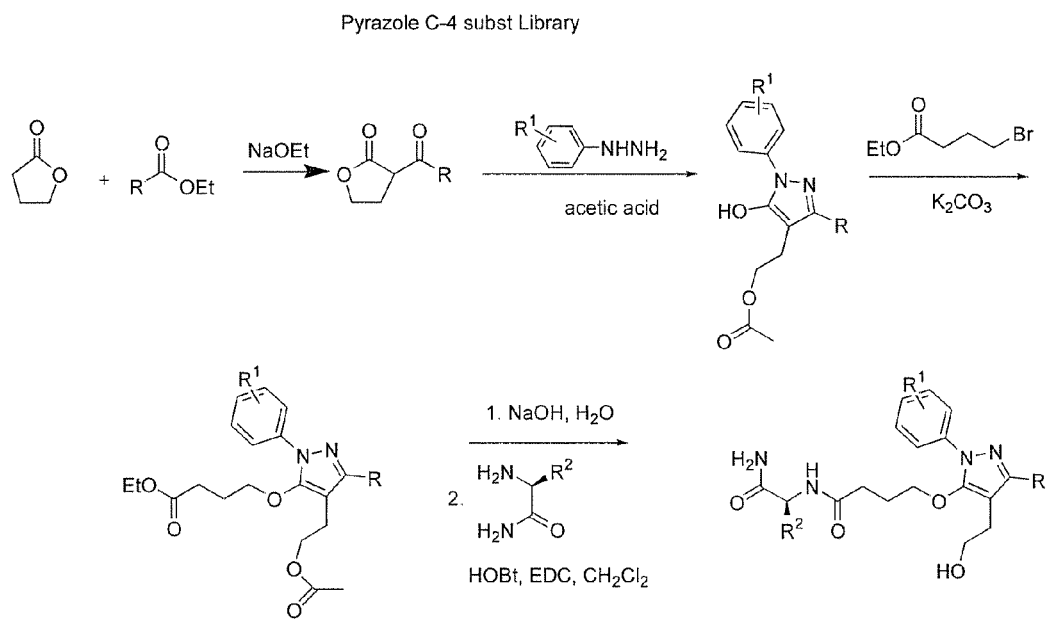
FIG. 6 illustrates a synthetic scheme for making substitutions at the 4-position of a 5-membered aromatic ring having two heteroatoms within prenylation inhibitor structures of the present invention.

FIG. 6 shows a synthetic scheme for making substitutions at the 4-position of a 5-membered aromatic ring having two or three heteroatoms within prenylation inhibitor structures of the present invention.

Whether or not formed using the approaches shown in FIGS. 1-6, the compounds of the present invention that are basic in nature are capable of forming a wide variety of different salts with various inorganic and organic acids. Although such salts must be pharmaceutically acceptable in order to be administered to organisms, it may be desirable to initially isolate compounds of the present invention from reaction mixtures as pharmaceutically unacceptable salts, which are then converted back to the free base compounds by treatment with an alkaline reagent, and subsequently converted to pharmaceutically acceptable acid addition salts. The acid addition salts of the basic compounds of this invention are readily prepared by treating the compounds with substantially equivalent amounts of chosen mineral or organic acids in aqueous solvent mediums, or in suitable organic solvents such as methanol and ethanol. Upon careful evaporation of these solvents, the desired solid salts are readily obtained.

Desired salts can also be precipitated from solutions of the free base compounds in organic solvents by adding to the solutions appropriate mineral or organic acids.

Those compounds of the present invention that are acidic in nature are similarly capable of forming base salts with various cations. As above, when a pharmaceutically acceptable salt is required, it may be desirable to initially isolate a compound of the present invention from a reaction mixture as a pharmaceutically unacceptable salt, which can then be converted to a pharmaceutically acceptable salt in a process analogous to that described above. Examples of base salts include alkali metal or alkaline-earth metal salts and particularly sodium, amine and potassium salts. These salts are all prepared by conventional techniques. The chemical bases used to prepare the pharmaceutically acceptable base salts of this invention are those which form non-toxic base salts with the acidic compounds of the present invention. Such nontoxic base salts include those derived from pharmacologically acceptable cations such as sodium, potassium, calcium, magnesium, and various amine cations. These salts can easily be prepared by treating the corresponding acidic compounds with an aqueous solution containing the desired pharmacologically acceptable bases and then evaporating the resulting solution to dryness, preferably under reduced pressure. They may also be prepared by mixing lower alkanolic solutions to dryness in the same manner as before. In either case, stoichiometric quantities of reagents are preferably employed in order to ensure completeness of reaction and maximum yields of the desired final product.

This invention encompasses both crystalline and non-crystalline (e.g., amorphous) forms of the salts of the compounds of this invention. These salts can be used to increase the solubility or stability of the compounds disclosed herein. They may also aid in the isolation and purification of the compounds.

Suitable methods of synthesizing the compound of the present invention may yield mixtures of regioisomers and/or diastereomers. These mixtures, which are encompassed by the compounds and methods of the present invention, can be separated by any means known to those skilled in the art. Suitable techniques include high performance liquid chromatography (HPLC) and the formation and crystallization of chiral salts. See, e.g., Jacques et al., *Enantiomers, Racemates and Resolutions*, Wiley-Interscience, New York, N.Y., 1981; Wilen et al., *Tetrahedron*, 1977, 33, 2725; Eliel, *Stereochemistry of Carbon Compounds*, McGraw-Hill, New York, N.Y., 1962; and Wilen, *Tables of Resolving Agents and Optical Resolutions*, Eliel, ed., Univ. of Notre Dame Press, Notre Dame, Ind., 1972, p. 268. The resulting enantiomerically enriched compounds are encompassed by the present invention.

The ability of the compounds of the present invention to inhibit protein prenylation of, for example, Ras or Ras-like proteins, may be determined by methods known to those skilled in the art such as the methods shown in the Examples below, and by methods disclosed in the references incorporated herein. In certain embodiments of the present invention, compounds of the present invention are inhibitory in the GGPTase I assay described in detail in Example 4. For example, compounds of the present invention, at a concentration of 10 µM in the GGPTase I assay described in Example 4, preferably show a percent inhibition of at least about 20%, more preferably at least about 35% and more preferably at least about 50%. GGPTase I may be prepared and purified according to the method described by Zhang et al., *J. Biol. Chem.*, 1994, 9, 23465-23470, and U.S. Pat. No. 5,789,558, which is incorporated herein in its entirety by this reference.

GGPTase II may be prepared by a method as disclosed in, for example, Johannes et al., *Eur. J. Biochem.*, 1996, 239, 362-368; and Witter and Poulter, *Biochemistry*, 1996, 35, 10454-10463, all of which are incorporated herein in their entirety by this reference. FPTase may be prepared and purified by methods such as those disclosed by U.S. Pat. Nos. 5,141,851 and 5,578,477, both of which are incorporated herein in their entirety by this reference.

The compounds of the present invention can be used for inhibiting protein prenylation by contacting an isoprenoid transferase with the compound. The compound can be contacted with a cell, in vitro or ex vivo, and be taken up by the cell. The compounds of the present invention can also be administered to an organism to achieve a desired effect. An organism may be a plant or an animal, preferably a mammal, and more preferably a human.

For inhibiting protein prenylation in an animal, the compound of the present invention can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

In one particular embodiment of the present invention, protein prenylation inhibition is used to treat or prevent conditions in an organism due to Ras or Ras-like protein prenylation. In animals, such diseases include, but are not limited to, cancer, restenosis, psoriasis, endometriosis, proliferative disorders, atherosclerosis, ischemia, myocardial ischemic disorders such as myocardial infarction, high serum cholesterol levels, viral infection, fungal infections, yeast infections or corneal neovascularization. In plants, such diseases include yeast and viral infections.

The method of the present invention can also include the administration of a dosage form comprising at least one compound of the present invention alone or in combination with other drugs or compounds. Other drugs or compounds that may be administered in combination with the compounds of the present invention may aid in the treatment of the disease or disorder being treated, or may reduce or mitigate unwanted side-effects that may result from the administration of the compounds.

The magnitude of a prophylactic or therapeutic dose of a compound of the present invention used in the prevention, treatment, or management of a disorder or condition can be readily determined by one of skill in the art using in vitro and in vivo assays such as those described below. As those of skill in the art will readily recognize, however, the magnitude of a prophylactic or therapeutic dose of a prenylation inhibitor will vary with the severity of the disorder or condition to be treated, the route of administration, and the specific compound used. The dose, and perhaps the dose frequency, will also vary according to the age, body weight, and response of the individual patient.

Typically, the physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration. In another aspect, the therapeutic dosage can be sufficient to achieve blood levels of the therapeutic agent of between about 5 micromolar and about 10 micromolar.

In one exemplary application, a suitable amount of a compound of the present invention is administered to a mammal undergoing treatment for cancer. Administration occurs in an amount of between about 0.1 mg/kg body weight to about 20 mg/kg body weight per day, preferably between about 0.5 mg/kg body weight to about 10 mg/kg body weight per day.

In another exemplary application, a suitable amount of a compound of this invention is administered to a mammal undergoing treatment for atherosclerosis. The magnitude of a prophylactic or therapeutic dose of the compound will vary with the nature and severity of the condition to be treated, and with the particular compound and its route of administration. In general, however, administration of a compound of the present invention for treatment of atherosclerosis occurs in an amount of between about 0.1 mg/kg body weight to about 100 mg/kg of body weight per day, preferably between about 0.5 mg/kg body weight to about 10 mg/kg of body weight per day.

It is recommended that children and patients aged over 65 years initially receive low doses, and that they then be titrated based on individual response(s) or blood level(s). It may be necessary to use dosages outside the ranges identified above in some cases as will be apparent to those skilled in the art. Further, it is noted that the clinician or treating physician will know how and when to adjust, interrupt, or terminate therapy in conjunction with individual patient response.

When used to inhibit protein prenylation in plants, the compounds of the present invention may be administered as aerosols using conventional spraying techniques, or may be mixed or dissolved in the food, soil and/or water provided to the plants. Other methods of administration known in the art are also encompassed by the invention.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least about 0.1% of active compound. The percentage of the compositions and preparation can, of course, be varied and can conveniently be between about 1% to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid such that it is possible to be delivered by syringe. It can be stable under the conditions of manufacture and storage and must be preserved against the contaminating action of microorganisms such as bacteria and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions may be accomplished by the inclusion of agents delaying absorption in the injectable preparation, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

Because of their ease of administration, tablets and capsules represent the most advantageous oral dosage unit form, in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices capable of releasing the active ingredient (prenylation inhibitor) at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices that may be adapted for the administration of the active ingredients of the present invention are described in U.S. Pat. Nos.: 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are incorporated herein in their entirety by this reference.

Pharmaceutical compositions for use in the methods of the present invention may be prepared by any methods known in the pharmaceutical sciences. Such methods are well known to the art and as described, for example, in Remington: The Science and Practice of Pharmacy, Lippincott, Williams & Wilkins, pubs, 20th edition (2000). All of these methods include the step of bringing the active ingredient into association with the carrier that constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

Additional objects, advantages, and novel features of this invention will become apparent to those skilled in the art upon examination of the following examples thereof, which are not intended to be limiting.

EXAMPLES

Example 1

This example illustrates methods for synthesizing compounds of the present invention.

Coupling to Polystyrene Rink Resin

About 42 grams (g) of Fmoc-protected Rink polystyrene resin and about 100 milliliter (ml) of dimethylformamide (DMF) were combined in a 500 ml peptide vessel and shaken for about 5 minutes. The DMF was removed, about 200 ml of 20% piperidine in DMF was added to the vessel, and the mixture was shaken for 30 minutes. This step was repeated prior to the solvent being removed. Following removal of the solvent, the resin was deprotected by being washed 3 times with 30 ml of DMF and twice with 200 ml of 1-methyl-2-pyrrolidinone (NMP). The resin was then dried for about 1 hour in vacuo. About 2 equivalents of an amino acid, about 2 equivalents of benzotriazol-1-yl-oxy-tris-pyrrolidino-phosphonium hexafluorophosphate (PyBOP), about 2 equivalents of N-hydroxybenzotriazole (HOBt), and about 200 ml of NMP were mixed in a 250 ml beaker. Before addition to the peptide vessel, containing the deprotected Rink resin, about 4 equivalents of diisopropylethylamine (DIEA) was added to the mixture and stirred for about 1 minute. The mixture was then shaken for about 2 hours in the peptide vessel. After this time, the solvent was removed and the resin was washed 3 times with about 200 ml of NMP and 3 times with about 200 ml of dichloromethane (DCM). A ninhydrin test was performed, using standard methods, to determine if amide formation was complete. Once the coupling was complete, the resin was dried overnight in vacuo.

About 5 g of the resin was suspended in about 30 ml of DMF, placed in a 50 ml syringe with a polyethylene filter (available from POREX Technologies, Fairburn, Ga.) and shaken for about 5 minutes. The DMF was removed, about 30 ml of 20% piperidine in DMF was added to the syringe, and the mixture was shaken for another 30 minutes. This step was repeated before the solvent was removed and the deprotected resin was washed 3 times with about 30 ml of DMF and 2 times with about 30 ml of DCM. About 1.5 equivalents of ketoacid, about 1.8 equivalents of PyBOP, about 1.8 equivalents of HOBt and about 30 ml of NMP (30 ml) were combined. About 4 equivalents of DIEA was added to the mixture and stirred for about 1 minute. The mixture was added to the syringe and shaken for about 16 hours. After this time the solvent was removed and the resin was washed 3 times with about 30 ml of DMF and 3 times with about 30 ml of DCM. A ninhydrin test was used to determine if amide formation was complete. Once the coupling was complete, the resin was dried overnight in vacuo.

About 2 g of resin complex from above was placed in a 35 ml thick-walled glass ACE pressure tube with about 10 equivalents of methyl nicotinate and about 25 ml of dimethylacetamide (DMA) and then vortexed for about 1 minute. About 30 equivalents of 60% NaH in oil was added over an about 30 minute period under controlled conditions; continuous vortexing, $N_2$ blanket, periodic capping and venting. The mixture was very exothermic. The pressure tube was sealed and rotated from about 85° C. to about 90° C. for about 1 hour. The tube was allowed to cool to about 25° C. in the incubator, chilled to about 0° C., and opened behind a Plexiglas shield. The resin, with residual NaH, was slowly poured over about a 10 minute period into a 500 ml peptide vessel containing about 50 ml of 15% HOAc (aq). The remaining NaH was quenched. Following the quenching, the resin was washed with about 50 ml of 15% HOAc (aq), then 2 times with about 50 ml of DMF, 2 times with about 50 ml of EtOAc, 1 time with about 50 ml of isopropanol, 1 time with about 50 ml of MeOH, and then dried overnight in vacuo.

Library Production

About 0.05 g of each resin-bound complex set from above was dispensed into discrete wells of a 96-well polypropylene plate (Polyfiltronics Unifilter; 0.8 ml volume; 10 µm polypropylene filter) using a repeater pipette and a 1:1 DMF:chloroform colloid solution of the resin (yielding 48×0.25 ml aliquots). The resin was then washed 2 times with about 0.5 ml of dichloromethylene and dried using a 96-well plate vacuum box.

The bottom of the 96-well plate was sealed with a TiterTop and secured to the bottom of a 96-well plate press apparatus. An about 0.7 M solution of a selected hydrazine or substituted hydrazine in about 0.6 ml of 2:1:1 DMF:mesitylene:MeOH was added to individual wells in the plate using a BioHit 8-channel pipetter. The top of the 96-well plate was sealed with another TiterTop, and the 96-well press apparatus was sealed. The plate apparatus was rotated overnight at 25° C. Following removal of the plate from the apparatus, the solvent was drained and the resin was washed 4 times with about 0.4 ml DMF, 2 times with about 0.4 ml MeOH, 3 times with about 0.4 ml methylene chloride, and then dried for about 1 hour using the 96-well vacuum box.

Cleavage of Product from Polystyrene Rink Resin:

About 0.4 ml of 1:1 trifluoroacetic acid (TFA):methylene chloride was added to each well of a semi-sealed 96-well in the 96-well plate apparatus. The 96-well plate was then shaken at 300 rpm for about 30 minutes. Using the 96-well plate vacuum box, the solvent was transferred to a marked Beckman 96-well plate. The cleavage process was repeated twice with 1:1 TFA:DCM and the resin was washed with 1:1 acetone:DCM. The solvent in the Beckman 96-well plate was evaporated and the remaining product lyophilized 3 times with 1:1 acetonitrile:water.

$^1$H and $^{13}$C NMR spectra were obtained on a Bruker AM-250 at 250 MHz and 62.9 MHz, respectively, using DMSO-$d_6$ as the solvent. All peaks were referenced to the DMSO quintet at 2.49 ppm.

Molecular weight determinations were made using a PE-Sciex API 100 MS based detector (available from Sciex, Concord, Ontario) equipped with an Ion Spray Source. Flow Injection Analysis was carried out using a HTS-PAL auto sampler (available from CTC Analytics, Zwingen, Switzerland) and a HP 1100 binary pump (available from Hewlett-Packard, Palo Alto, Calif.).

The analyte was diluted to about 0.25 ml with 1:1 MeOH/CH$_3$CN containing 1% HOAc. About 25 µL of the analyte sample was directly infused into the Ion Source at about 70 µL/1 minutes. Electron spray ionization (ESI) mass spectra was acquired in the positive ion mode. The ion-spray needle was kept at about 4500 V and the orifice and ring potentials were at about 50 V and about 300V, respectively. The mass range of 150-650 Da was scanned using a step size of 0.1 Da and a dwell time of 0.6 ms resulting in a total scan time of about 3.2 seconds.

A Gilson HPLC system consisting of two 25 ml 306 Pump Heads, a 119 Variable Dual Wavelength Detector, a 215 Liquid Handler, a 811C Dynamic Mixer, and a 806 Manometric Module, was used for product analysis and purification.

Analytical HPLC on the individual components of the pyrazole library identified, on average, the presence of pyrazole regioisomers. The analytical conditions used are as follows:

Column: Thomson Instrument Co. 50×4.6 mm C18 5 µm
Flow Rate: 1 ml/minutes.
Mobile Phase A: H$_2$O With 0.1% Trifluoroacetic Acid (TFA)
Mobile Phase B: Methanol (CH$_3$OH)
Gradient: 90%-10% mobile phase A in 12-minutes.
10%-90% mobile phase B in 12-minutes.
Wavelength: 254 nm
Injection: 10 µL Analytical HPLC conditions were optimized for Preparative HPLC of the pyrazole compounds. The preparative conditions were as follows:

Column: Thomson Instrument Co. 50×21.5 mm C18 5 µm
Flow Rate: 11 ml/minutes.
Mobile Phase A: H$_2$O With 0.1% Trifluoroacetic Acid (TFA)
Mobile Phase B: Methanol (CH$_3$OH)
Gradient: 35%-10% mobile phase A in 7 minutes.
65%-90% mobile phase B in 7 minutes.
Wavelength: 254 nm
Injection: 250 µL N-Alkylation of Pyrazole Amides Amide nitrogen(s) of compounds of the present invention may be alkylated using the following procedure:

1. In a scintillation vial, the pyrazole starting material (1 eq) was dissolved in DMF.
2. Sodium hydride (15 eq) was placed in a vial fitted with a septum and drying tube, and the vial was shaken for 1 hour.
3. Alkylating reagent (e g., ethyl iodide) (15 eq) was then added, and the reaction mixture was shaken for 5 hours.
4. The reaction was then worked up by diluting the mixture with ethyl acetate and washing with water and brine. The organic layers were collected and dried over magnesium sulfate.
5. The organic layers were filtered and concentrated in vacuo using a Savant.
6. Crude material was purified by flash chromatography using a solvent system of 97:3 CH$_2$Cl$_2$:MeOH.

Example 2

Figure 7:
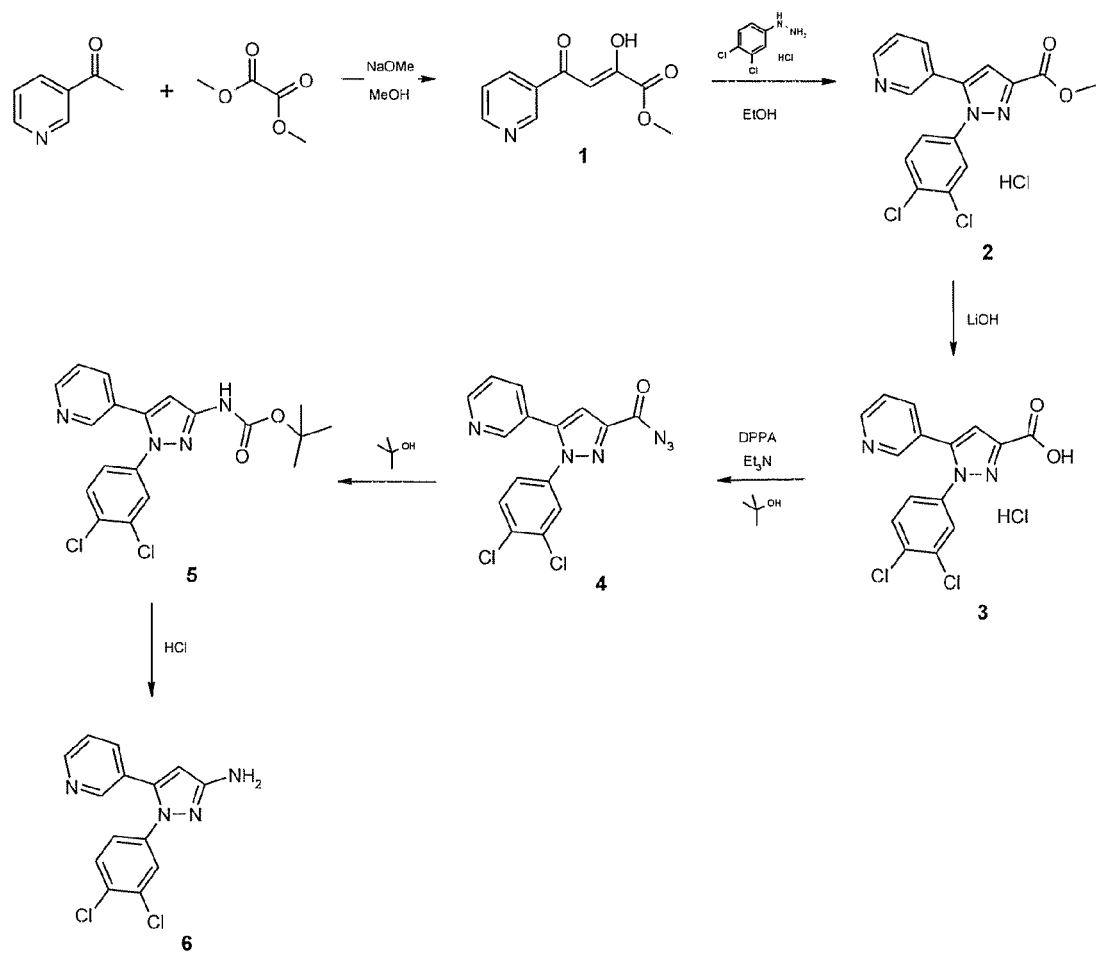
FIG. 7 illustrates the formation of a compound of the present invention having a central pyrazole ring structure.

This example shows the formation of the pyrazole ring having different substituents. Referring to FIG. 7, the individual intermediates were formed under the following reaction conditions.

2-Hydroxy-4-oxo-4-pyridin-3-ylbut-2-enoic acid methyl ester (1). Acetyl pyridine (1.81 mL, 16.5 mmol) and methyl oxalate (3.12 g, 26.4 mmol) were dissolved in MeOH (30 mL, anhydrous). Sodium methoxide (6.9 mL, 25% in MeOH) was added over 10 min. Reaction solidified and was complete after 15 minutes. The solid mass was dissolved when acidified with HCl (10%, aqueous). The pH was then adjusted with NH$_4$OH (conc) until precipitation ceased. The resulting solid was taken up in EtOAc. The aqueous layer was removed and extracted twice with EtOAc. The combined EtOAc layers were washed with water and brine, dried over MgSO$_4$, filtered, and concentrated in vacuo. Collected 1 (2.90 g, 85%) as an off-white solid.

1-(3,4-Dichlorophenyl)-5-pyridin-3-yl-1H-pyrazole-3-carboxylic acid methyl ester hydrochloride (2). To a solution of 1 (2.90 g, 14.0 mmol) in EtOH (60 mL, anhydrous) was added 3,4-dichlorophenyl hydrazine hydrochloride (3.29 g, 15.4 mmol). The solution was heated to reflux for 30 min and then cooled to 0° C. The precipitate was collected by filtration and washed with H$_2$O and MeOH to yield 2 (3.79 g, 70%) as an off-white powder.

1-(3,4-Dichlorophenyl)-5-pyridin-3-yl-1H-pyrazole-3-carboxylic acid methyl ester hydrochloride (3). A suspension of 2 (2.0 g, 5.74 mmol) in THF (40 mL) and H$_2$O (11 mL) was treated with NaOH pellets (581 mg, 14.5 mmol) and heated to reflux for 1 h. The THF was removed in vacuo and the pH of the remaining aqueous portion was adjusted to 1.5 with HCl (10%, aqueous). The resulting solid was dissolved in EtOAc. The aqueous layer was removed and extracted with EtOAc-MeOH (4:1). The combined organic layers were dried (brine and MgSO$_4$) and concentrated in vacuo to yield 3 (1.61 g, 84%) as a white solid.

1-(3,4-Dichlorophenyl)-5-pyridin-3-yl-1H-pyrazole-3-carbonyl azide (4). A solution of 3 (100 mg, 0.27 mmol) and t-butyl alcohol (28.4 µL, 0.30 mmol) in DMF (5 mL, anhydrous) was cooled to 0° C. Diphenylphosphoryl azide (64 µL, 0.30 mmol) was added to the solution. Triethylamine (103 µL, 0.60 mmol) was then added over 10 min. The solution was stirred 1 h at 0° C. and allowed to warm to room temperature and stir 16 h. The reaction was quenched with H$_2$O and extracted with EtOAc. The combined organic layers were washed with H$_2$O, dried (brine and MgSO$_4$), filtered, and concentrated in vacuo. The resulting oil was purified by flash chromatography by eluting with hexane-EtOAc (1:1). Collected 4 (86 mg, 90%) as a yellow crystalline solid.

[1-(3,4-Dichlorophenyl)-5-pyridin-3-yl-1H-pyrazol-3-yl] carbomic acid tert-butyl (5). A solution of 4 (98 mg, 0.24 mmol) and t-butyl alcohol (3 mL,) were heated to reflux for 4 h. The solution was cooled and concentrated. The resulting oil was purified by flash chromatography. Collected 4 (74 mg, 76%) as a clear oil.

1-(3,4-Dichlorophenyl)-5-pyridin-3-yl-1H-pyrazol-3-yl amine (6). The BOC-protected compound (5, 74 mg, 0.18 mmol) was dissolved in MeOH (10 mL, anhydrous) and HCl (g) was bubbled through for 10 min. The solution was stirred 3 h at room temperature. Concentrated in vacuo. The remaining oil was dissolved in $H_2O$ and neutralized with $NaHCO_3$ (sat. aqueous). The aqueous solution was extracted with $CHCl_3$; the combined organic layers were dried (brine and $MgSO_4$), filtered, and concentrated. The resulting oil was purified by flash chromatography (chloroform-MeOH—$NH_4OH$ 95:5:0.5) to yield 6 (39 mg, 70%) as a yellow crystalline solid.

Example 3

Figure 8A:
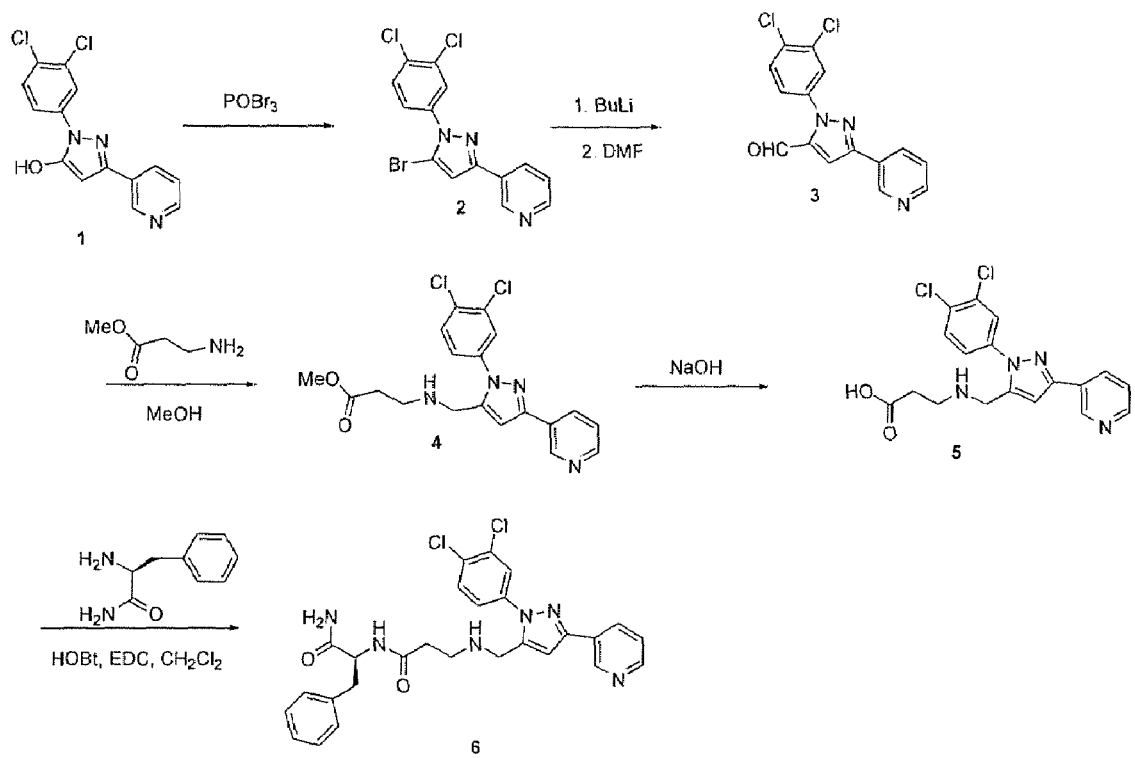
FIG. 8a illustrates the synthesis of alkyl linking groups within compounds of the present invention through an ethyl-methylamine linking group.

This example demonstrates the synthesis of alkyl linking groups within compounds of the present invention through the ethyl-methylamine linking group example. Referring to FIG. 8a, the individual intermediates were formed under the following reaction conditions.

(2). Hydroxypyrazole 1 (7.0 g, 22.9 mmol) and $POBr_3$ (100 g, 348 mmol) were placed in a 115° C. oil bath with stirring. The slurry was heated until just before all the hydroxypyrazole (1) totally dissolved. The reaction was then cooled to RT and slowly poured into EtOAc (250 mL, 0° C.). Crushed ice was slowly added to the EtOAc solution. The pH of the aqueous layer was adjusted to 10 with NaOH pellets. The biphasic solution was further diluted with water and the organic layer was removed. The remaining aqueous layer was extracted with EtOAc (×3) and the organic layers were combined, dried (brine and $MgSO_4$), and concentrated in vacuo. The resulting solid was purified by flash chromatography (chloroform-methanol-$NH_4OH$ 99.9:0.1:0.1 to 99.8:0.2:0.1) to afford bromopyrazole 2 (3.44 g, 40%) as an off-white solid.

(3). Bromopyrazole 2 (9.13 g, 24.7 mmol) was dissolved in THF (190 mL, anhydrous) and cooled to −78° C. n-BuLi (9.32 mL, 2.5 M in hexane) was slowly added. The solution was stirred for 15 min at −78° C. N-methyl formanilide (30.0 mL, 321 mmol) was slowly added to the −78° C. solution, which was then allowed to slowly warm to RT while stirring 16 h. The reaction was quenched with water and extracted with EtOAc (×3). The combined organic layers were dried (brine and $MgSO_4$) and concentrated in vacuo. The resulting solid was purified by flash chromatography with a gradient of hexane-EtOAc (2:1 to 1:1) to afford 3 (1.10 g, 14%) as an off-white solid.

(4). β-Alanine ethyl ester HCl (279 mg, 2.52 mmol), 3 (400 mg, 1.26 mmol), and DIEA (437 μL, 2.52 mmol) were stirred in MeOH (4.0 mL, anhydrous) along with molecular sieves for 16 h. The reaction mixture was filtered and the filtrate was concentrated in vacuo. Water was added to the resulting paste and the aqueous mixture was extracted with EtOAc (×4); the combined EtOAc layers were dried (brine and $MgSO_4$) and concentrated in vacuo. The resulting oil was purified by flash chromatography by eluting with a gradient of EtOAc to EtOAc-MeOH (10:1). The product 4 (180 mg, 35%) was isolated as a white solid.

(5). To a solution of pyrazole 4 (85 mg, 0.210 mmol) in THF (2 mL) and water (2 mL) was added LiOH (10 mg). The resulting biphasic mixture was stirred at RT for 4 h. The reaction was diluted with water (4 mL) and the pH was adjusted to 6 with HCl (10% aqueous). The cloudy solution was cooled to 5° C. for 16 h. The precipitate was collected by filtration and then dried by concentrating in vacuo with toluene. The acid 5 (70 mg, 85%) was isolated as a white solid.

(6). To a solution of acid 5 (70 mg, 0.179 mmol) in DMF (6.0 mL, anhydrous) was added DPPA (42.4 μL, 0.197 mmol) and DIEA (34.2 μL, 0.197 mmol). The resulting solution was then stirred at RT for 18 h. L-Phe-$NH_2$ (147 mg, 0.895 mmol) was added and stirred at 60° C. for 8 h. The reaction was diluted with water and extracted with EtOAc (×4). The combined EtOAc layers were washed with water (×2), dried (brine and $MgSO_4$), and concentrated in vacuo. The resulting oil was purified by flash chromatography with a gradient of chloroform-MeOH—$NH_4OH$ (98:2:0.5 to 95:5:0.5). The product 6 (40 mg, 41%) was isolated as a white foam.

Figure 8B:
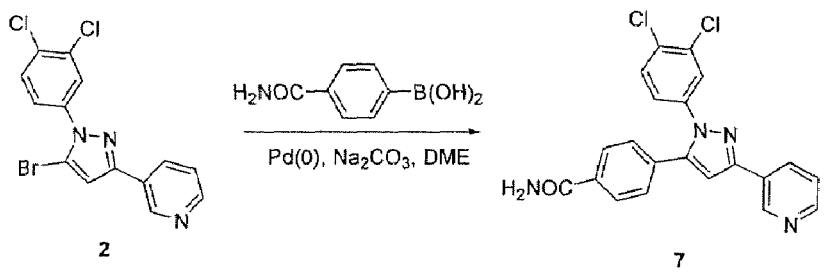
FIG. 8b illustrates the synthesis of a compound of the present invention having a phenyl linking group added to a pyrazole ring.

Similarly, the phenyl linking group of the compounds of the present invention could be synthesized within this scheme using the boronic acid coupling reaction. Referring to FIG. 8b, the phenyl linking group can be added to the pyrazole ring using the following synthetic methods.

(7). Bromopyrazole 2 (100 mg, 0.270 mmol), DME (2.33 mL), water (175 μL), $Na_2CO_3$ (142 mg, 1.34 mmol) and (4-aminocarbonyl phenyl)boronic acid (97 mg, 0.588 mmol) were stirred together. Nitrogen was bubbled through the reaction for 30 min. $Pd(PPh_3)_4$ (31 mg, 0.0268 mmol) was added and the reaction was heated to 90° C. for 40 h. The reaction was diluted with water and extracted with EtOAc (×3). The combined organic layers were dried (brine and $MgSO_4$) and concentrated in vacuo. The resulting oil was purified by flash chromatography ($CHCl_3$-MeOH; 20:1). Product 7 (23 mg, 20%) was isolated as a solid.

Example 4

Figure 9:
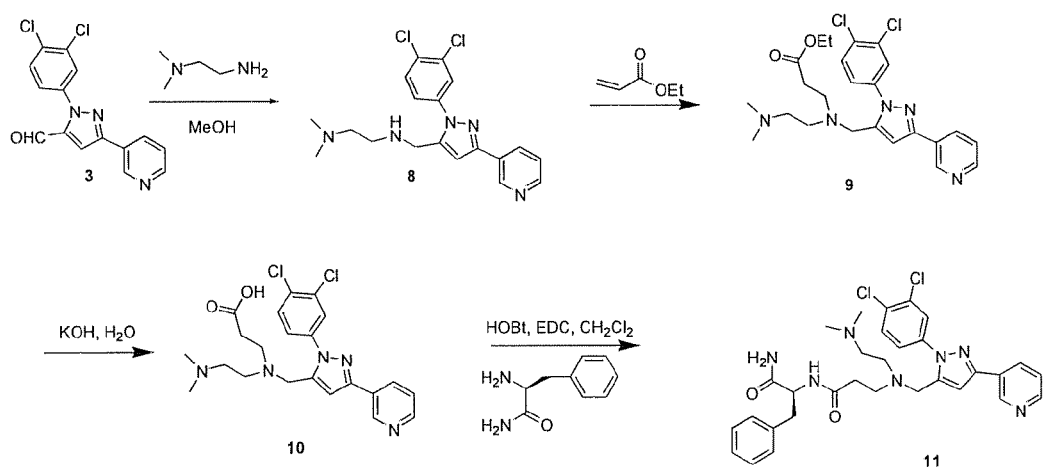
FIG. 9 illustrates the synthesis of prenylation inhibitors of the present invention with amine linking groups having different alkyl substituents.

This example demonstrates the synthesis of prenylation inhibitors of the present invention with amine linking groups having different alkyl substituents. Referring to FIG. 9, the individual intermediates were formed under the following reaction conditions.

(8). N,N-Dimethylethylenediamine (39 μL, 0.35 mmol) and 3 (95 mg, 0.30 mmol) were dissolved in MeOH (20 mL, anhydrous) and stirred for 2 h at rt. $NaBH_3CN$ (78 mg, 1.25 mmol) was added and stirred for 16 h before removing the solvent in vacuo. The residue was taken up in water and extracted with EtOAc. The organic layer was concentrated in vacuo. The residue was purified by flash chromatography (EtOAc-MeOH; 4:1 with 1% $NH_4OH$) to give the product 8 (54 mg, 46%).

(10). Ethyl acrylate (50 μL, 0.463 mmol), 8 (54 mg, 0.14 mmol), and EtOH (10 mL, anhydrous) were added to a sealed tube. The reaction was reacted under microwave conditions at 150° C. for 40 min. The solvent was removed in vacuo. The residue was purified by flash chromatography (EtOAc-MeOH; 7:3 with 1% $NH_4OH$). 9 was then subjected to hydrolysis with KOH to give 10 (22 mg, 35%).

(11). HOBt (14 mg, 0.10 mmol), 10 (22 mg, 0.05 mmol), L-Phe-$NH_2$ (16.4 mg, 0.10 mmol), EDCI (20 mg, 0.1 mmol) and DIEA (0.1 ml, 0.57 mmol) were stirred in $CH_2Cl_2$ (3.0 mL, anhydrous) for 16 h. The reaction mixture-was washed with $H_2O$. The organic layer was washed with brine and concentrated in vacuo. The crude reaction mixture was purified by flash chromatography (EtOAc-MeOH; 7:3 with 1% $NH_4OH$) to afford 11 (10 mg, 32%).

Example 5

Figure 10:
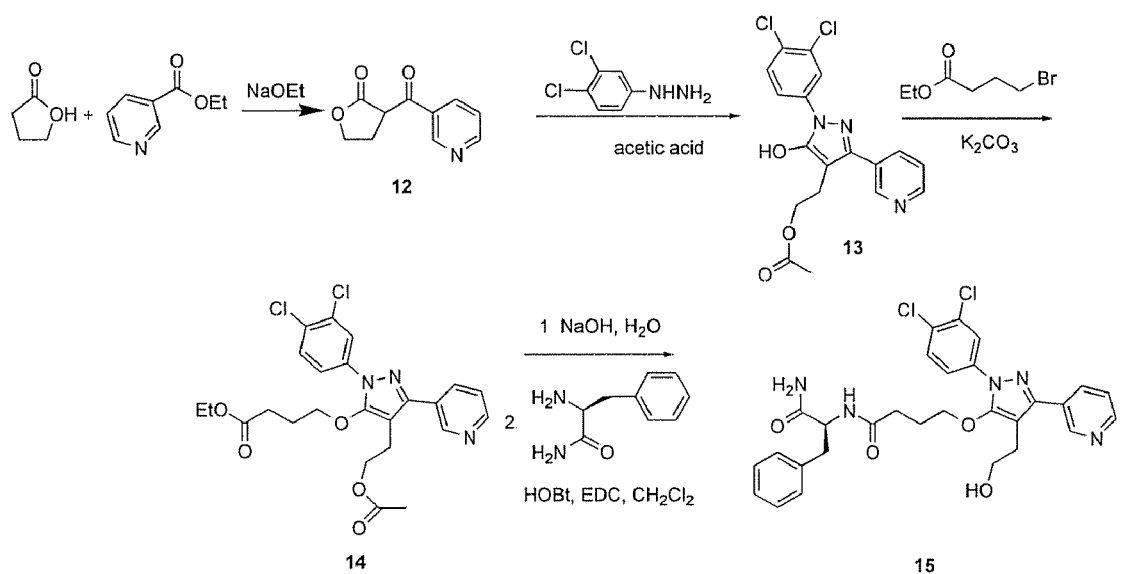
FIG. 10 illustrates the synthesis of prenylation inhibitors of the present invention having a central pyrazole ring with a substituted alkyl group.

This example demonstrates the synthesis of prenylation inhibitors of the present invention with different substituent on the pyrazole ring. Referring to FIG. 10, the individual intermediates were formed under the following reaction conditions.

(12). NaOEt (21% w/v EtOH; 2.04 g, 30 mmol) was added to a dry flask under $N_2$. The mixture was cooled to 0° C. During the cooling process, ethyl nicotinate (4.53 g, 30 mmol) was added in one portion. γ-Butyrolactone (2.58 g, 30 mmol) was added dropwise over 30 min. The mixture was stirred at 0° C. for 1 h. Upon removal of the ice bath the reaction was allowed to warm to rt and was heated to ~65° C. overnight. The solvent was removed in vacuo and the residue was diluted with $H_2O$, and extracted with diethyl ether to remove any unreacted starting material. The aqueous phase was acidified with 1N HCl and extracted with DCM. The organic layer was washed with $H_2O$, brine, and dried ($Na_2SO4$), to yield 12 (2.87 g, 50%) as a brown oil.

(13). To a solution of keto-lactone 12 (2.39 g, 12.5 mmol) in acetic acid (100 mL) was added 3,4-dichlorophenylhydrazine HCl (2.93 g, 13.75 mmol) in one portion. The mixture was heated at reflux overnight and then cooled to RT. The mixture was diluted with de-ionized $H_2O$ and extracted with EtOAc. The organic layer was washed with saturated sodium bicarbonate (×2) and de-ionized $H_2O$ (×2), and dried over $Na_2SO_4$. Rotary evaporation and flash chromatography afforded 13 as a light yellow solid (1.49 g, 34%).

(14). To a solution of acetoxyethylpyrazole 13 (844 mg, 2.41 mmol) in anhydrous DMF (20 mL) was added $K_2CO_3$ (501 mg, 3.62 mmol) and ethyl-4-bromobutyrate (470 mg, 2.41 mmol). The reaction mixture was heated to 80° C. and stirred overnight. The reaction mixture was diluted with $H_2O$ and extracted with EtOAc. The organic layer was washed with $H_2O$, brine, dried ($Na_2SO_4$, and concentrated in vacuo. The residue was purified by flash chromatography (hexane-EtOAc, 3:1) to yield 14 (1.0 g, 82%) as a yellow oil.

(15). Pyrazole 14 (1.00 g, 1.98 mmol) was dissolved in a mixture of THF, MeOH, and 10% w/v NaOH solution (8:4:4). This solution was stirred at rt overnight. The reaction mixture was concentrated in vacuo and the residue was diluted with $H_2O$. The aqueous solution was acidified to pH 4 with HCl (10% solution). The product was extracted with 9:1 EtOAc/MeOH (×3). The combined organic layers were washed with $H_2O$, dried ($Na_2SO_4$), and concentrated in vacuo to afford the acid (803 mg, 1.84 mmol) which was dissolved in $CH_2Cl_2$ (25 mL). HOBt (373 mg, 2.76 mmol) was added to the solution and was stirred for 20 minutes at rt. L-Phe-$NH_2$ (453 mg, 2.76 mmol), EDCI (707 mg, 3.68 mmol), and DIEA (641 μL, 3.68 mmol) were added and the solution was stirred at rt overnight. The reaction mixture was washed with $H_2O$. The organic layer was washed with brine and concentrated in vacuo. Flash chromatography afforded impure 15 as a cream solid. The solid was diluted with $H_2O$, filtered, and dried to yield 15 (651 mg, 61%) as a white solid.

Example 6

Figure 11:
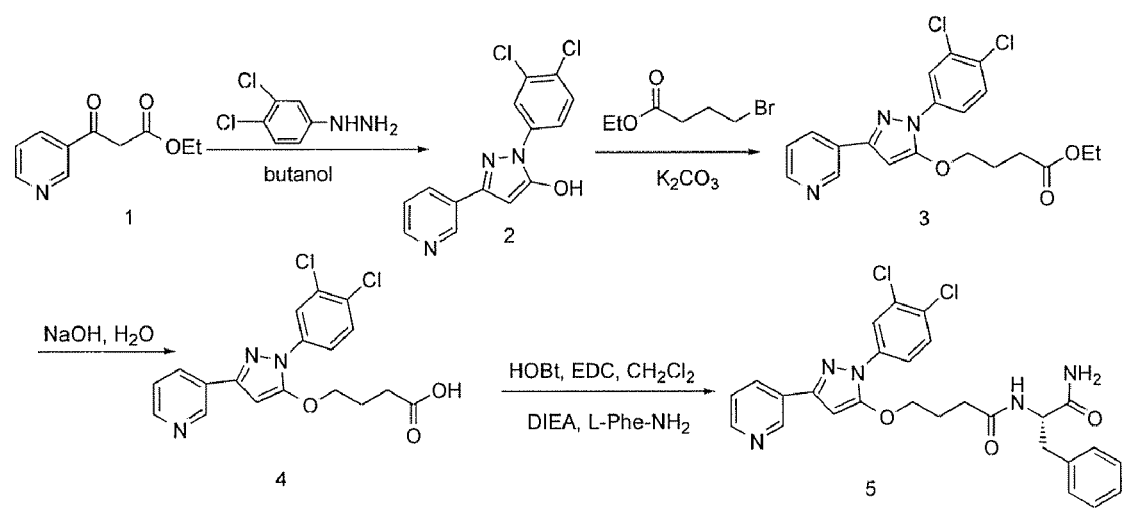
FIG. 11 illustrates the synthesis of prenylation inhibitors of the present invention having an ether linker on a central pyrazole ring.

This example demonstrates the synthesis of an ether linkage within the prenylation inhibitors of the present invention. Referring to FIG. 11, the ether linkage is formed on the pyrazole ring by the following reactions.

(1). Sodium (38 g, 1.65 mmol) was slowly added to 900 mL of ethanol and left to stir at RT for 4 h. Solvent was removed in vacuo. Ethyl acetate (200 mL) was added to the sodium ethoxide followed by ethyl nicotinate (22.6 mL, 0.166 mol) in 150 mL of ethyl acetate. The reaction was heated to reflux for 16 h. Water (200 mL) was added to the reaction mixture. The aqueous layer was acidified to pH 6 with HCl and extracted with ether. Solvent was removed in vacuo to give a brown oil which was purified by column chromatography (2:1, hexanes-EtOAc), to give 1 (101 g, 52%).

(2). Keto ester 1 (51.6 g, 267 mmol) and 3,4-dichloophenyl-hydrazine hydrochloride (57.1 g, 267 mmol) were dissolved in 800 mL of acetic acid and heated at 100 C. for 1 h. The reaction was cooled and left to stand at RT overnight. The crystals that formed were filtered off and washed with cold acetic acid to give 2 as an off-white solid (75 g, 92%).

(3). Ethyl 4-bromobutyrate (28.8 g, 147.6 mmol), 2 (37.5 g, 123.0 mmol), $K_2CO_3$ (20.4 g, 147.6 mmol) were added to 1 L of DMF. The reaction was heated at 70° C. for 16 h. Water was added, extracted with ethyl acetate and dried over $MgSO_4$. Column chromatography (1:1 hexanes-EtOAc) gave 3 as a white solid (27.8 g, 54%).

(4). NaOH (35 mL, 10% w/v) was added to 3 (2.2 g, 5.6 mmol) in THF/MeOH (2:1, 90 mL) and heated at reflux for 2 h. The reaction mixture was acidified to pH 6 with HCl. The solid that crashed out of solution was filtered, washed with water and extracted with ethyl acetate. The organic layers were concentrated in vacuo to give 4 (2.1 g, 95%).

(5). To a solution of 4 (100 mg, 0.25 mmol) in $CH_2Cl_2$ (10 ml) were added HOBt (69 mg, 0.5 mmol), EDCI (98 mg, 0.5 mmol), L-phenylalaninamide (61 mg, 0.38 mmol), and DIEA (130 μl, 0.75 mmol) sequentially. The reaction mixture was stirred at RT for 15 h. The reaction mixture was diluted with $CH_2Cl_2$ (10 mL) and washed with $NaHCO_3$ (5%, 10 mL) and brine (10 mL). The aqueous phase was extracted with $CH_2Cl_2$ (3×10 mL). The organic phase was dried over $MgSO_4$ and concentrated in vacuo to give a white solid. Column chromatography (EtOAc) gave 5 as a white solid (94 mg, 70%).

Example 7

Figure 12:
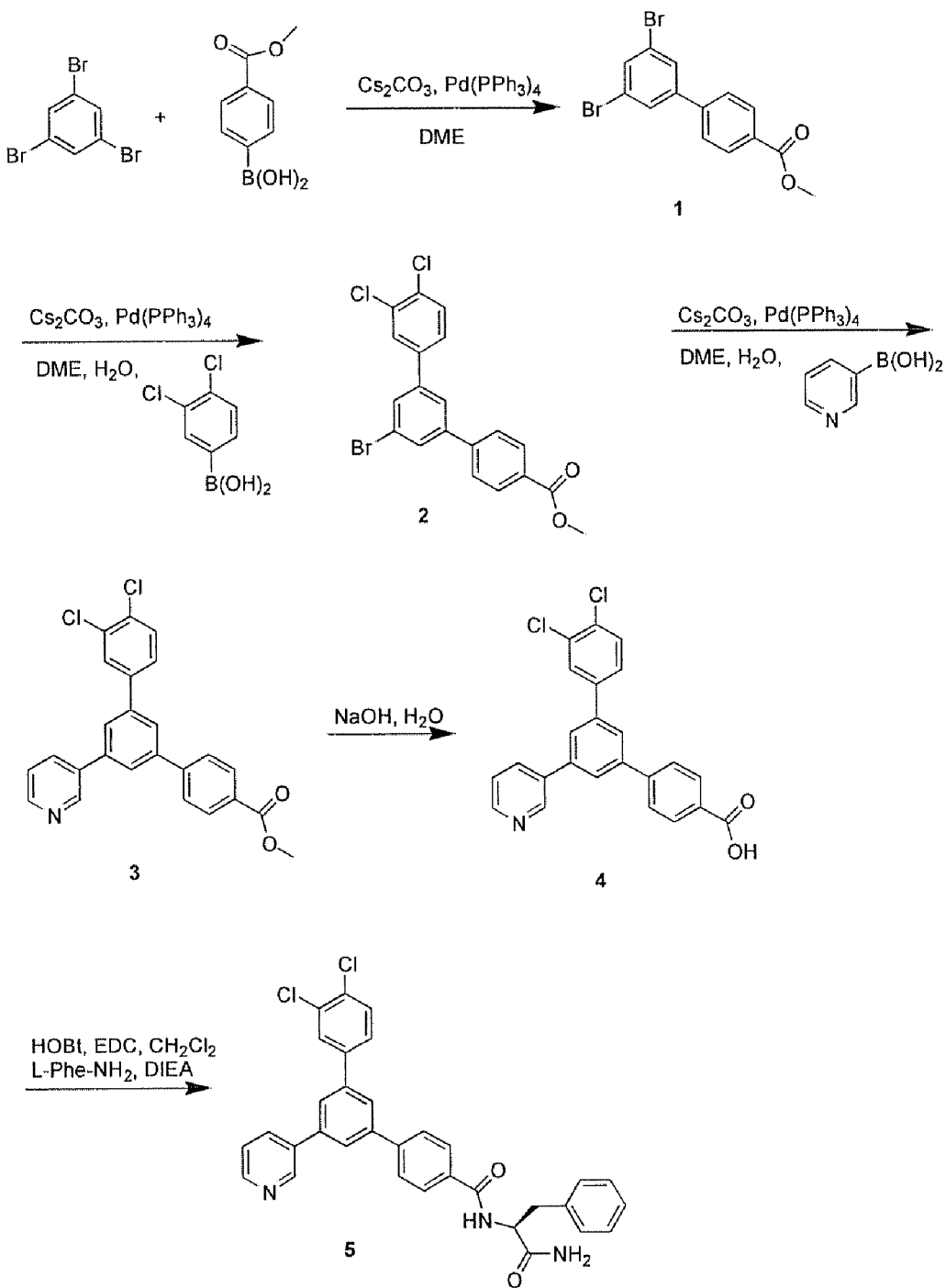
FIG. 12 illustrates the synthesis of a prenylation inhibitor of the present invention having a central phenyl ring to which a phenyl linking group is attached.

This example shows the synthesis of a prenylation inhibitor of the present invention having a central phenyl ring to which a phenyl linking group is attached. Referring to FIG. 12, these phenyl groups are incorporated within the prenylation inhibitors of the present invention by the following reactions.

(1). 1,3,5-Tribromobenzene (5.0 g, 15.9 mmol), 4-methoxy-carbonylphenylboronic acid (5.71 g, 31.8 mmol), and cesium carbonate (10.35 g, 31.8 mmol) were added to DME (20 mL). The flask was evacuated and flushed with nitrogen three times. $Pd(PPh_3)_4$ was added, the reaction vessel was covered with aluminum foil and the reaction mixture was allowed to stir at RT for 16 h. The reaction mixture was diluted with $H_2O$ (50 mL), and extracted with EtOAc (3×40 mL). The extractions were combined, washed with brine, and dried over $MgSO_4$. Concentration in vacuo, yielded a light brown solid. Column chromatography (hexanes), yielded an off-white solid. (725 mg, 12%).

(2). 3,4-Dichlorophenyl boronic acid (360 mg, 1.35 mmol), 1 (250 mg, 0.69 mmol), cesium carbonate (440 mg, 1.35 mmol), and $H_2O$ (2 mL,) were added to DME (10 mL,). The reaction vessel was evacuated and flushed with nitrogen three times. $Pd(PPh_3)_4$ was added, the reaction vessel was covered in aluminum foil and the reaction mixture was allowed to stir at RT for 16 h. The reaction was diluted with $H_2O$ (50 mL), and extracted with EtOAc (3×40 mL). The extractions were combined, washed with brine, and dried over MgSO$_4$. Concentration in vacuo, yielded a light yellow solid. Column chromatography (99:1 hexanes-EtOAc) afforded a white solid, (98 mg, 33%).

(3). Pyridine-3-boronic acid (46 mg, 0.38 mmol), 2 (98 mg, 0.19 mmol), cesium carbonate (124 mg, 0.38 mmol) and H$_2$O (0.4 mL), were added to DME (2 mL). The reaction vessel was evacuated and flushed with nitrogen three times. Pd(PPh$_3$)$_4$ was added and the reaction vessel was covered in aluminum foil. The reaction mixture was heated at 70° C. for 16 h. The reaction mixture was cooled to RT and diluted with H$_2$O (50 mL), and extracted with EtOAc (3×40 mL). The extractions were combined, washed with brine, and dried over MgSO$_4$. Concentration in vacuo, yielded a brown solid. Column chromatography (4:1 hexanes-EtOAc) afforded a light-brown solid, (9.3 mg, 11.3%).

(4). Hydrolysis of 3 using conditions similar to those described previously gave 4 which was used without further purification.

(5). Coupling of 4 with Phe-NH$_2$ using the conditions previously described afforded 5.

Example 8

Figure 13:
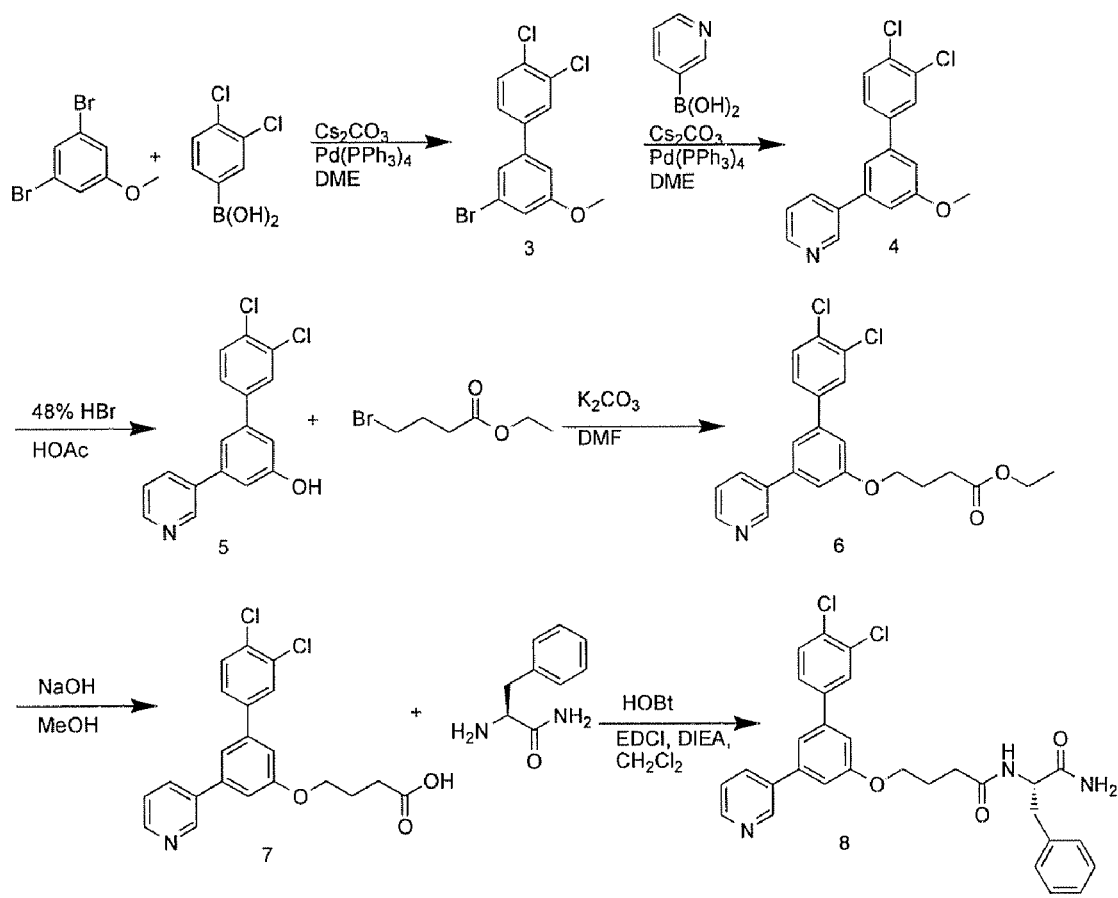
FIG. 13 illustrates the synthesis of a prenylation inhibitor of the present invention having a central phenyl ring attached to an ether linking group.

This example shows the synthesis of a prenylation inhibitor of the present invention having a central phenyl ring attached to an ether linking group. Referring to FIG. 13, this ether group is combined with the central phenyl group by the following reactions.

(3). 3-4-Dichlorophenylboronic acid (3.0 g, 11.3 mmol), 3,5-dibromoanisole (2.0 g, 7.5 mmol), Cs$_2$CO$_3$ (4.9 g, 15.0 mmol) were added to 60 mL of DME. A stream of nitrogen was gently bubbled through the reaction mixture for 15 min to deaerate the reaction mixture. Pd(PPh$_3$)$_4$ (868 mg, 0.752 mmol) was added and the reaction mixture was reacted at RT for 16 h. The reaction mixture was diluted with EtOAc (100 mL) and extracted with water (300 mL). The organic phase was dried over MgSO$_4$ and concentrated in vacuo to give a dark residue. Column chromatography afforded impure 3 as a white solid (1.6 g).

(4). 3-Pyridylboronic acid (1.18 g, 9.64 mmol), 3 (1.6 g, 4.82 mmol), Cs$_2$CO$_3$ (3.14 g, 9.64 mmol) were added to 40 mL of DME. A stream of nitrogen was gently bubbled through the reaction mixture for 15 min to deaerate the reaction mixture. Pd(PPh$_3$)$_4$ (557 mg, 0.482 mmol) was added and the reaction mixture was heated at reflux for 16 h. The reaction mixture was diluted with EtOAc (30 mL) and extracted with water (100 mL). The organic phase was dried over MgSO$_4$ and concentrated in vacuo to give a dark residue. Column chromatography afforded 4 as a white solid (390 mg, 25%).

(5). 4 (50 mg, 0.152 mmol) was dissolved in HBr (aq. 48%, 100 µL) and acetic acid (5 mL) and heated to 110° C. for 48 h. The reaction mixture was diluted with water (20 mL) and basified to pH 7 with 10% sodium hydroxide. The organic phase is concentrated down to a residue and brought up in CH$_2$Cl$_2$ and filtered to give a gray solid (41 mg, 86%).

(6). To a solution of 5 (40 mg, 0.13 mmol) in DMF (5 mL) was added K$_2$CO$_3$ (35 mg, 0.25 mmol) and ethyl-4-bromobutyrate (23 µL, 0.15 mmol). The solution was heated to 60° C. for 60 h. H$_2$O was added and the product was extracted with CH$_2$Cl$_2$ (5×20 mL). The organic layer was dried over MgSO$_4$ and solvent was removed in vacuo to give crude 6 as an oil. This was used without further purification.

(7). Hydrolysis of 6 using conditions similar to those described previously gave 7 that was used without further purification.

(8). Coupling of 7 with Phe-NH$_2$ using the conditions previously described afforded 8.

Example 9

Figure 14:
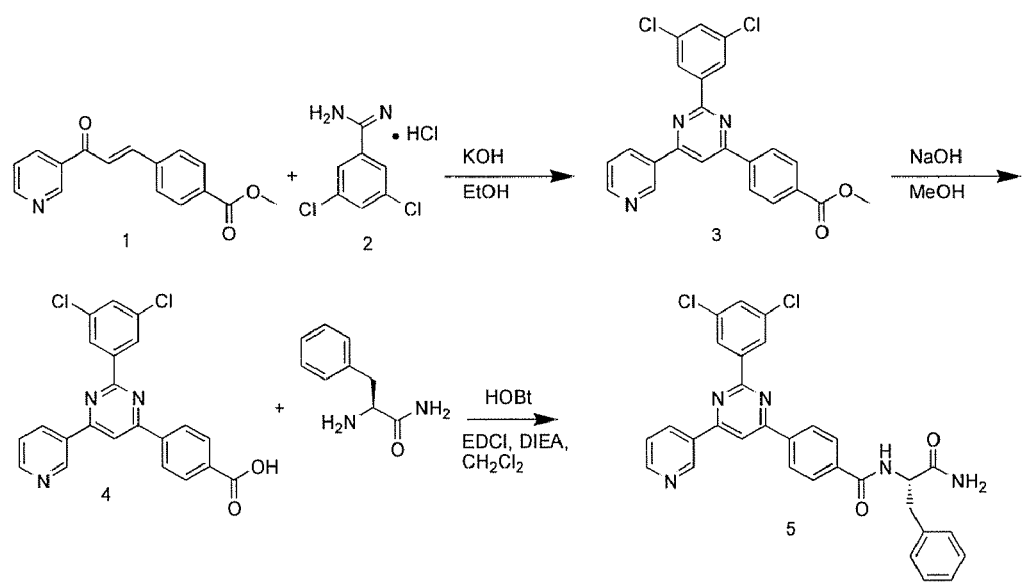
FIG. 14 illustrates the synthesis of a prenylation inhibitor of the present invention having a central pyrimidine ring matched with a phenyl linking group.

This example shows the synthesis of a prenylation inhibitor of the present invention having a central pyrimidine ring matched with a phenyl linking group. Referring to FIG. 14, this phenyl group is combined with the central pyrimidine group by the following reactions.

(1). 3-Acetyl pyridine (4.4 g, 40.0 mmol) was added to 150 mL of dry CH$_2$Cl$_2$. TiCl$_4$ (1.0 M, 40.0 mL, 40.0 mmol) was added at 0° C. followed by triethylamine (5.57 mL, 40.0 mmol). The reaction mixture was stirred for 30 min before the dropwise addition of methy 4-formylbenzoate (5.0 g, 30.5 mmol, 50 mL CH$_2$Cl$_2$). The reaction mixture was allowed to warm to RT and stirred for a further 16 h. Solvent was removed in vacuo and the residue was washed with CH$_2$Cl$_2$ to give 1 as a yellow solid (5.0 g, 61%).

(3). The chalcone 1 (500 mg, 1.87 mmol), 3,5-dichlorobenzamidine hydrochloride 2 (422 mg, 1.87 mmol) and KOH (104 mg, 1.87 mmol) were added to 10 mL of EtOH. The reaction mixture was heated at reflux for 2 h. The reaction mixture was filtered and washed with EtOH (30 mL) and water (30 mL). This afforded a yellow solid 3 (281 mg, 34%) which was dried in vacuo.

(4). To a solution of 3 (130 mg, 0.30 mmol) in MeOH (10 mL) was added NaOH (200 mg, 5.0 mmol). The solution was heated at reflux for 1 h. The reaction mixture was diluted with CH$_2$Cl$_2$/EtOH (3:1, 30 mL) and acidified to pH 6 with 10% HCl. The aqueous phase was extracted with CH$_2$Cl$_2$/EtOH (3:1, 3×30 mL). The organic phase was dried over MgSO$_4$ and concentrated in vacuo to give a white solid (29 mg, 23%).

(5). HOBt (9.3 mg, 76 µmol), 4 (29 mg, 69 µmol) were added to 5 mL of CH$_2$Cl$_2$ and stirred for 10 min. EDCI (14.4 mg, 76 µmol), L-phenylalaninamide (22.5 mg, 0.14 mmol), and DIEA (9.75 mg, 13.1 µl, 76 µmol) were added and the reaction mixture was stirred at RT for 14 h. The reaction mixture was diluted with CH$_2$Cl$_2$/EtOH 3:1 (50 mL) and washed with NaHCO$_3$ (5%, 50 mL) and brine (50 mL). The aqueous phase was extracted with CH$_2$Cl$_2$/EtOH (3:1, 3×50 mL). The organic phase was dried over MgSO$_4$ and concentrated in vacuo to give a white solid. The crude reaction mixture was purified by flash chromatography (EtOAc→4:1 EtOAc-MeOH) to give 5 (6.7 mg, 17%).

Example 10

Figure 15:
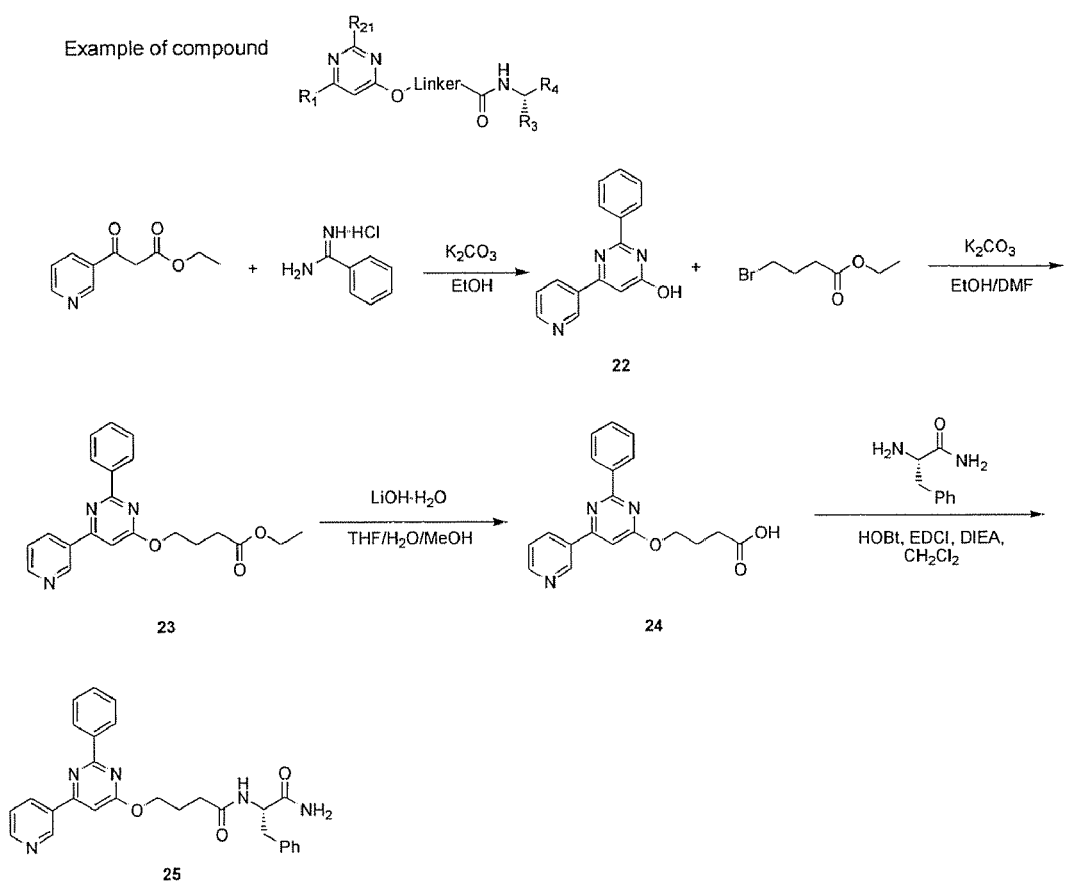
FIG. 15 illustrates the synthesis of a prenylation inhibitor of the present invention having a central pyrimidine ring with an ether linking group.

Similar to Example 9 above, this example shows the synthesis of a prenylation inhibitor of the present invention having a central pyrimidine ring with an ether linking group. Referring to FIG. 15, this ether group is combined with the central pyrimidine group by the following reactions.

(22). To a solution of ethyl nicotinoylacetate (1.58 g, 6.12 mmol) and benzamidine hydrochloride (962 mg, 6.12 mmol) in EtOH (15 mL) was added K$_2$CO$_3$ (1.69 g, 12.7 mmol). The reaction mixture was heated to 70° C. for 16 h. The mixture was diluted with EtOAc and filtered to remove K$_2$CO$_3$. The solid was washed repeatedly with EtOAc. The organic layers were combined and the solvent was removed in vacuo. The crude solid was washed with hexanes and used without further purification.

(23). Ethyl bromobutyrate (0.89 mL, 6.1 mmol), 22 (1.50 g, 6.1 mmol), and K$_2$CO$_3$ (1.27 g, 9.2 mmol) were combined in EtOH/DMF (4:1, 20 mL,). The reaction mixture was heated at 70° C. for 16 h, cooled to RT, filtered to remove K$_2$CO$_3$ and concentrated in vacuo to give a dark residue. Column chromatography gave 23 (740 mg, 33%).

(24). To a solution of 23 (700 mg, 1.93 mmol) in THF/H$_2$O/MeOH 2:2:1 (20 mL) was added LiOH.H$_2$O (324 mg, 7.71 mmol). The solution was heated at reflux for 1 h. The reaction mixture was concentrated in vacuo and diluted with H₂O (15 mL). The solution was acidified to pH ~6 with c.HCl and extracted with CH₂Cl₂/EtOH (3:1, 3×20 mL). The organic phase was dried over MgSO₄ and concentrated in vacuo to give an orange-yellow solid (580 mg, 90%).

(25). A solution of HOBt (94 mg, 61 μmol), EDCI (117 mg, 0.612 mmol), 24 (103 mg, 31 μmol) and DIEA (160 μL, 92 μmol) in CH₂Cl₂ (10 mL) was stirred at 0° C. for 30 min. L-phenylalaninamide (81 mg, 61 μmol) was added and the reaction mixture was stirred at RT for 16 h. The reaction mixture was diluted with CH₂Cl₂/MeOH (3:1, 50 mL) and washed with H₂O (50 mL). The aqueous phase was extracted with CH₂Cl₂/MeOH (3:1, 3×50 mL). The organic phase was dried over MgSO₄ and concentrated in vacuo to give a light yellow solid. The crude reaction mixture was washed repeatedly with CH₂Cl₂ to give 25 (75 mg, 51%).

Example 11

Figure 16:
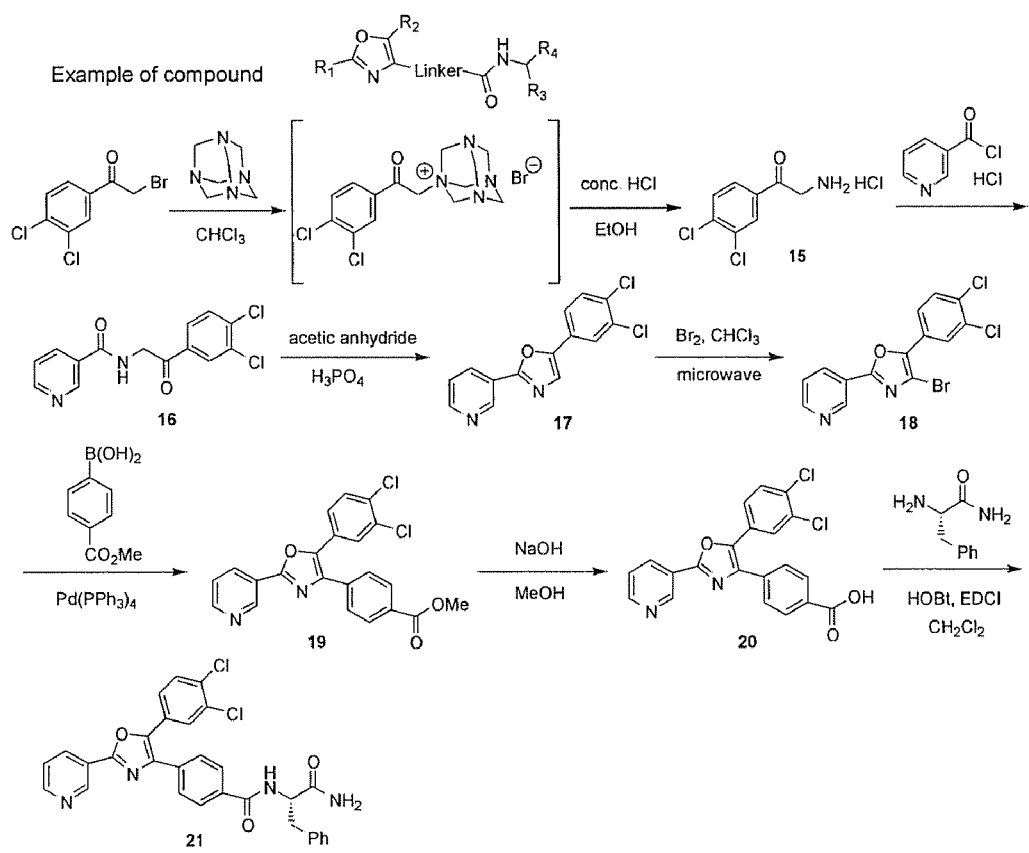
FIG. 16 illustrates the synthesis of a prenylation inhibitor of the present invention having a central oxazole ring and a phenyl linking group.

This example demonstrates the synthesis of a prenylation inhibitor of the present invention having a central oxazole ring and a phenyl linking group. Referring to FIG. 16, this phenyl group is combined with the central oxazole group by the following reactions.

(15). To a solution of 3,4-dichlorophenacetyl bromide (2.67 g, 10.0 mmol) in CHCl₃ (40 mL) was added hexamethylenetetramine (1.4 g, 10.0 mmol). The reaction mixture was heated at 60° C. for 0.5 h. The solid that formed was filtered and washed repeatedly with CHCl₃. The white solid was then suspended in EtOH (50 mL). c.HCl (5 mL) was added and the mixture was heated at reflux for 16 h. The mixture was cooled in an ice-bath and the solid that formed was filtered and washed with EtOH. The crude material (2.7 g) was used without further purification.

(16). Nicotinoyl chloride hydrochloride (1.56 g, 8.76 mmol) and 15 (1.96 g, 8.19 mmol) were suspended in pyridine (8 mL). The mixture was heated at 100° C. for 2.5 h, cooled to RT and poured into H₂O (20 mL). The orange solid thus formed was filtered, washed with H₂O and dried in vacuo to give 16 (1.18 g, 50%).

(17). To a solution of 16 (1.02 g, 3.32 mmol) in acetic anhydride (10 mL) was added phosphoric acid (85%, 850 μl). The brown solution was heated at reflux for 3 h. The reaction mixture was reduced to a residue under reduced pressure, redissolved in CH₂Cl₂/EtOH 3:1 and extracted with NaHCO₃ (5%). The organic phase was dried over MgSO₄ and concentrated in vacuo. Column chromatography afforded 17 (338 mg, 35%).

(18). To a solution of 17 (170 mg, 0.58 mmol) in CHCl₃ (3 mL) was added bromine (90 μl, 280 mg, 1.75 mmol). The mixture was subject to microwave heating for 20 min (CEM Explorer, power 200 W, temperature 105° C., pressure 100 PSI). The reaction mixture was dried down under reduced pressure to give 18 as a yellow solid (185 mg, 86%).

(19). 4-Methoxycarbonylphenylboronic acid (188 mg, 1.03 mmol), 18 (189 mg, 0.51 mmol), Cs₂CO₃ (667 mg, 2.04 mmol) were added to 15 mL of DME and 2 mL, of H₂O. A stream of nitrogen was gently bubbled through the reaction mixture for 15 min to deaerate the reaction mixture. Pd(PPh₃)₄ (15 mg, 13 μmol) was added and the reaction mixture was heated at reflux for 16 h. The reaction mixture was diluted with CH₂Cl₂ (50 mL) and extracted with NaHCO₃ (50 mL, 5%). The organic phase was dried over MgSO₄ and concentrated in vacuo to give a dark residue. Column chromatography afforded 19 as a white solid (60 mg, 27%).

(20). To a solution of 19 (68 mg, 0.16 mmol) in MeOH/CH₂Cl₂ (4:1, 10 mL) was added NaOH (128 mg, 3.2 mmol). The yellow solution was heated at reflux for 1 h. The reaction mixture was diluted with MeOH/CH₂Cl₂ (1:1, 50 mL) and acidified to pH 6 with 5% HCl. The aqueous phase was extracted with CH₂Cl₂/MeOH (3:1, 3×30 mL). The organic phase was dried over MgSO₄ and concentrated in vacuo to give a white solid (67 mg, 100%).

(21). To a solution of 20 (67 mg, 0.16 mmol) in CH₂Cl₂ (10 ml) were added HOBt (49 mg, 0.32 mmol), EDCI (61 mg, 0.32 mmol), L-phenylalaninamide (52 mg, 0.32 mmol), and DIEA (41 mg, 56 μl, 0.32 mmol) sequentially. The reaction mixture was stirred at RT for 15 h. The reaction mixture was diluted with CH₂Cl₂/EtOH 3:1 (50 mL) and washed with NaHCO₃ (5%, 50 mL) and brine (50 mL). The aqueous phase was extracted with CH₂Cl₂/EtOH 3:1 (3×50 mL). The organic phase was dried over MgSO₄ and concentrated in vacuo to give a white solid. The crude reaction mixture was washed with hexane and MeOH to give 21 (45 mg, 50%).

Example 12

Figure 17:
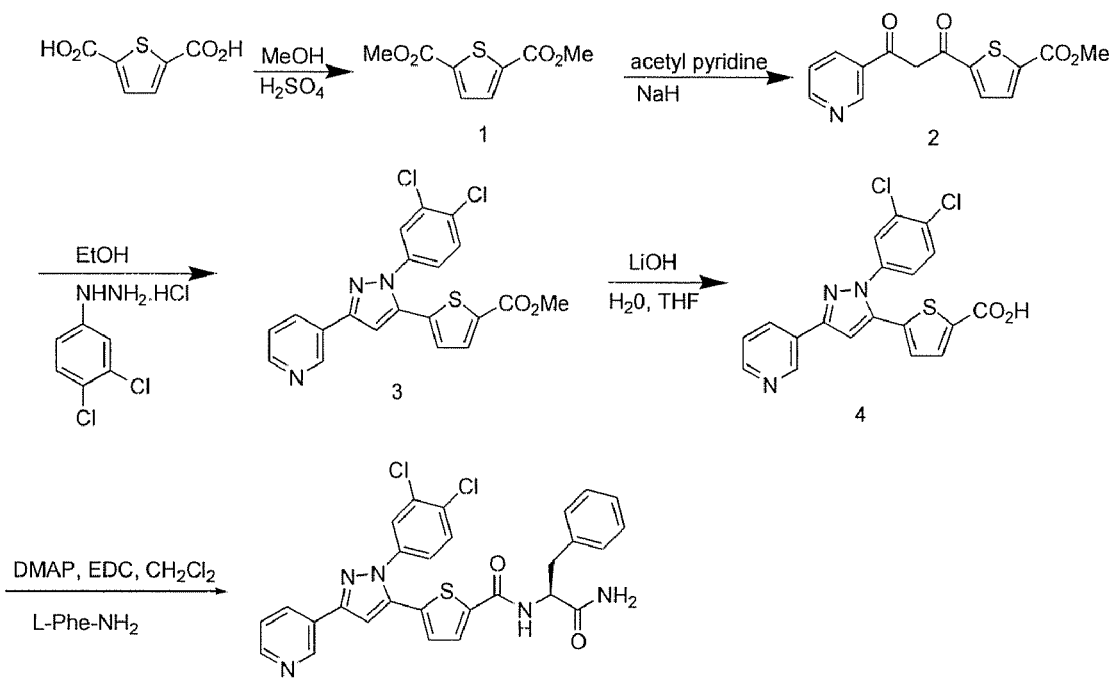
FIG. 17 illustrates the synthesis of a prenylation inhibitor of the present invention having a central pyrazole ring and a thiophene linking group.

This example demonstrates the synthesis of a prenylation inhibitor of the present invention having a central pyrazole ring and a thiophene linking group. Referring to FIG. 17, this thiophene group is combined with the central pyrazole group by the following reactions.

(1). 3,5-Thiophenedicarboxylic acid (21.2 g, 123 mmol) was dissolved in methanol (70 mL, anhydrous) and dichloroethane (70 mL, anhydrous). c.H₂SO₄ (10.6 mL) was added and the reaction mixture was heated at reflux for 40 h. Solvent was removed in vacuo and the solid was suspended in EtOAc, washed with saturated NaHCO₃ (2×200 mL) and brine and dried over MgSO₄. Solvent was removed in vacuo to yield 1 as a white powder (22.4 g, 91%).

(2). To NaH (7.68 g, 192 mmol, 60% dispersion in oil) was added acetyl pyridine (14.1 mL, 128 mmol) dissolved in THF (360 mL, anhydrous). The reaction mixture was heated at reflux for 1 h, cooled to RT and 1 (22.4 g, 112 mmol) was added over 30 min. The reaction was allowed to stir at RT for 48 h. Saturated NH₄Cl (100 mL) was added and concentrated under vacuum to give a solid. The solid was washed with H₂O and EtOAc and dried under vacuum at 60° C. The solid was then suspended in boiling methanol and filtered to give 2 as brown solid (15.4 g, 28%).

(3). 3,4-Dichlorophenylhydrazine hydrochloride (11.6 g, 54.4 mmol), and 2 (15.4 g, 49.4 mmol) were suspended in methanol (450 mL, anhydrous) and heated at reflux for 20 h. The solvent was removed in vacuo, the residue was dissolved in NaHCO₃, extracted with EtOAc (3×150 mL) and dried over MgSO₄. Column chromatography (2:1 hexanes-EtOAc to EtOAc) gave 3 (10.6 g, 59%) as a yellow solid.

(4). Methyl ester 3 (156 mg, 0.36 mmol) was dissolved in THF (3 mL) and H₂O (3 mL). LiOH (17 mg, 7.1 mmol) was added and the solution was stirred at RT for 20 h. Solvent was removed in vacuo and the residue was dissolved in H₂O. The aqueous layer was washed with CHCl₃ and then acidified with HCl (10% solution). The solid that precipitated out was collected, washed with H₂O and dried to give 4 (70 mg, 46%).

(5). To a solution of 4 (70 mg, 0.17 mmol) in CH₂Cl₂ (3 mL) were added DMAP (catalytic amount), EDCI (48 mg, 0.25 mmol), and L-phenylalaninamide (72 mg, 0.44 mmol). The reaction mixture was stirred at RT for 16 h. The reaction mixture was diluted with CH₂Cl₂ (10 mL) and washed with NaHCO₃ (5%, 10 mL) and brine (10 mL). The aqueous phase was extracted with CH₂Cl₂ (3×10 mL). The organic phase was dried over MgSO₄ and concentrated in vacuo to give a white solid. Column chromatography (EtOAc) gave 5 as a white solid (33 mg, 35%).

Example 13

Figure 18:
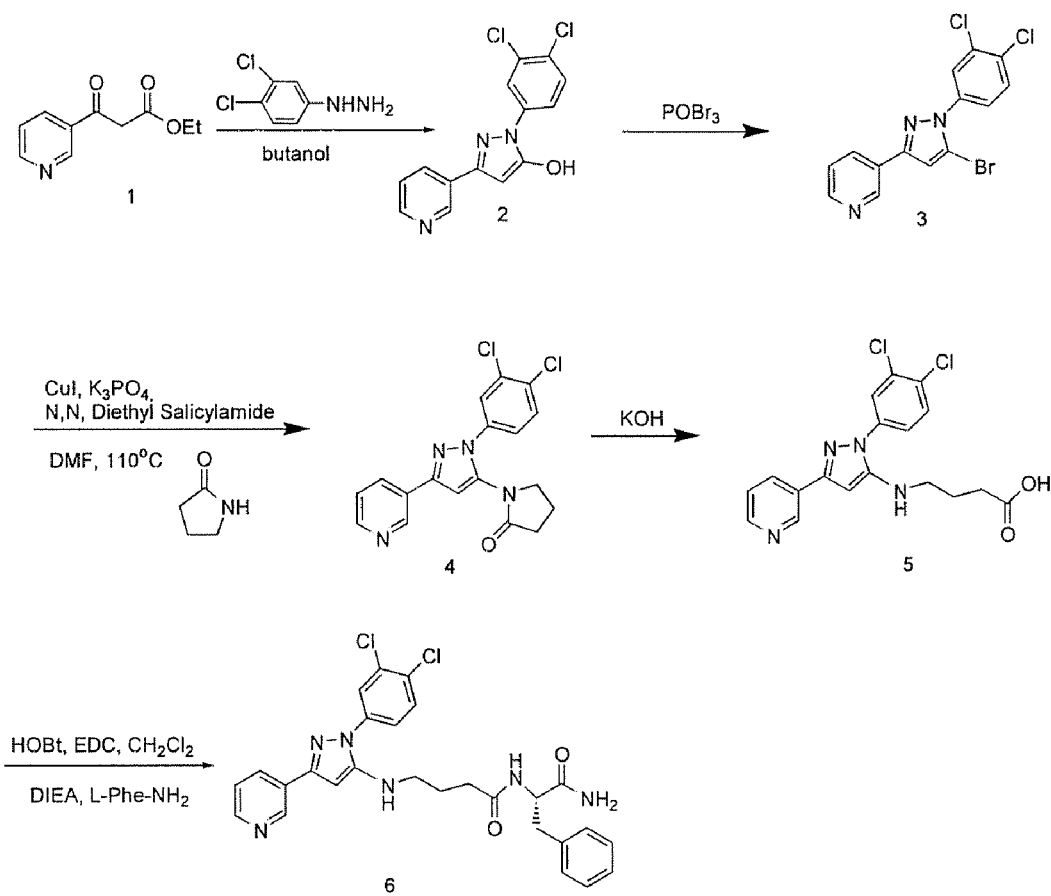
FIG. 18 illustrates the synthesis of a prenylation inhibitor of the present invention having a central pyrazole ring arid an amine linking group.

This example demonstrates the synthesis of a prenylation inhibitor of the present invention having a central pyrazole ring and an amine linking group. Referring to FIG. 18, this amine group is combined with the central pyrazole group by the following reactions.

(1). Sodium (38 g, 1.65 mmol) was slowly added to 900 mL of ethanol and left to stir at RT for 4 h. Solvent was removed in vacuo. Ethyl acetate (200 mL) was added to the sodium ethoxide followed by ethyl nicotinate (22.6 mL, 0.166 mol) in 150 mL of ethyl acetate. The reaction was heated to reflux for 16 h. Water (200 mL) was added to the reaction mixture. The aqueous layer was acidified to pH 6 with HCl and extracted with ether. Solvent was removed in vacuo to give a brown oil which was purified by column chromatography (2:1, hexanes-EtOAc), to give 1 (16.7 g, 52%).

(2). Keto ester 1 (51.6 g, 267 mmol) and 3,4-dichloophenylhydrazine hydrochloride (57.1 g, 267 mmol) were dissolved in 800 mL of acetic acid and heated at 100 C for 1 h. The reaction was cooled and left to stand at RT overnight. The crystals that formed were filtered off and washed with cold acetic acid to give 2 as an off-white solid (75 g, 92%).

(3). Hydroxypyrazole 2 (1.78 g, 5.8 mmol) and $POBr_3$ (23.4 g, 81.5 mmol) were placed in a 115° C. oil bath with stirring. The slurry was heated until just before all of 2 totally dissolved. The reaction was then cooled to RT and slowly poured into EtOAc (100 mL, 0° C.). Crushed ice was slowly added to the EtOAc solution. The pH of the aqueous layer was adjusted to 10 with NaOH pellets. The biphasic solution was further diluted with water and the organic layer was removed. The remaining aqueous layer was extracted with EtOAc (×3) and the organic layers were combined, dried (brine and $MgSO_4$), and concentrated in vacuo. The resulting solid was purified by flash chromatography (chloroform-methanol-$NH_4OH$ 99.9:0.1:0.1 to 99.8:0.2:0.1) to afford bromopyrazole 3 (1.28 g, 59%) as an off-white solid.

(4). CuI (12 mg, 63 µmol), N,N-diethylsalicylamide (40 mg, 0.2 mmol), 5-bromo-1-(3,4-dichlorophenyl)-3-pyridylpyrazole (250 mg, 0.68 mmol), and potassium phosphate (288 mg, 1.36 mmol) were added to an oven dried round-bottomed flask. The flask was evacuated and backfilled with nitrogen three times. A solution of 2-pyrrolidinone (170 mg, 2.0 mmol) in DMF (5 mL, anhydrous) was added via syringe at RT. The reaction was heated at 100° C. for 48 h. Solvent was removed in vacuo and the residue was partitioned between ethyl acetate and water. The organic layer was washed with brine, and dried over $MgSO_4$. Column Chromatography afforded 4 as an oily white solid (75 mg, 33% yield).

(5). Pyrazole 4 (165 mg, 0.44 mmol) was dissolved in methanol (10 mL). KOH (560 mg, 10.0 mmol) in $H_2O$ (2 mL) was added and the reaction mixture was stirred at 60° C. for 4 h. Solvent was removed in vacuo and the residue was partitioned between EtOAc and $H_2O$. The aqueous layer was acidified with acetic acid to pH 5 and extracted with EtOAc. The organic layer was washed with brine and dried over $MgSO_4$. Solvent was removed in vacuo to yield 5 (100 mg, 59%).

(6). To a solution of 5 (19 mg, 0.05 mmol) in $CH_2Cl_2$ (3 mL) were added HOBt (14 mg, 0.1 mmol), EDCI (19 mg, 0.1 mmol), L-phenylalaninamide (16 mg, 0.1 mmol), and DIEA (50 µl, 0.3 mmol). The reaction mixture was stirred at RT for 16 h. The reaction mixture was diluted with $CH_2Cl_2$ (10 mL) and washed with brine (5 mL). The aqueous phase was extracted with $CH_2Cl_2$ (3×10 mL). The organic phase was dried over $MgSO_4$ and concentrated in vacuo. Column chromatography (9:1, EtOAc-MeOH) gave 6 as a yellow solid (21 mg, 78%).

Example 14

This example illustrates a method for preparing and purifying GGPTase I.

GGPTase I was prepared and purified according to the method described by Zhang et al., *J. Biol. Chem.*, 1994, 9, 23465-23470, which is incorporated herein in its entirety by this reference.

Production of Recombinant Virus

Sf9 cells were obtained from the American Tissue Culture Collection. The cells were maintained in Grace's medium (Gibco), supplemented with about 3.3 mg/ml lactalbumin hydrolystate (Difco), about 3.3 mg/ml yeastolate (Difco), about 10% (v/v) fetal bovine serum (HyClone Laboratories, Logan, Utah), antibiotic-antimycotic mixture (Gibco), and about 0.1% Pluronic F-68 (Gibco) in 125 ml Spinner flask (available from Techne, Princeton, N.J.). To generate recombinant baculovirus, about $2\times10^6$ Sf9 cells were transfected with about 0.5 µg of BaculoGold wild-type viral DNA (available from PharMingen) and about 2 µg of either pVL-Fα (for α subunit expression) or pVL-Gβ (for GGPTase-Iβ subunit expression) using calcium-phosphate precipitation according to the manufacturer's instructions (PharMingen). The virus from each transfection was harvested after about 4 days and screened using a plaque assay as described by Summers and Smith, *A Manual of Methods for Baculovirus Vectors and Insect Cell Culture Procedures*, Texas Agricultural Experimentation Station, Bulletin #1555 (1987). Recombinant viruses obtained from this screen were subjected to two further rounds of plaque amplification to obtain purified viruses.

Production and Purification of Recombinant GGPTase-I

The purified recombinant viruses containing the cDNA sequences for the α subunit of FPTase and GGPTase, and the β subunit of GGPTase-I were used to co-infect about $1.5\times10^6$ Sf9 cells at multiplicities of infection of 5. Cells were harvested at about 65 hours post-infection by centrifugation at about 800×g for about 15 minutes. The cells were washed once with phosphate-buffered saline and the resulting cell pellet flash-frozen in liquid nitrogen. Cell extracts were prepared by thawing the cell suspension in 5 volumes of about 20 mM Tris-HCl, pH 7.7, about 1 mM EDTA, 1 mM EGTA, about 1 mM and a protease inhibitor mixture (Moomaw et al., *Methods Enzymol.*, 1995, 250, 12-21), incubating the cell suspension oil ice for about one hour, and disrupting using six strokes of a Dounce homogenizer. The resulting extract was centrifuged for about 1 hour at about 30,000×g, and the supernatant (designated as the soluble extract) was fractionated on a 5.0×10.0 cm column of DEAE-Sephacel (available from Pharmacia). The DEAE-Sephacel was first equilibrated with 50 mM Tris-Cl, pH 7.7, 1 mM DTT (Buffer A) at 4° C. The soluble extract containing about 160 mg protein was loaded into the DEAE column, which was then washed with about 50 ml Buffer A and eluted with a 200 ml gradient of 0-500 mM NaCl in Buffer A. Fractions of 3 ml were collected. The fractions containing the peak of GGPTase-I activity were pooled, concentrated and exchanged into Buffer A, and then loaded into a Q-HP column (1.0×20 cm, available from Pharmacia). The column was washed with about 20 ml of buffer A and eluted with a 200 ml gradient of 0-500 mM NaCl in Buffer A. The peak fractions, containing essentially homogeneous GGPTase-I, were pooled, flash-frozen in aliquots and stored at −80° C.

Example 15

This example illustrates a method for determining GGPTase-I activity.

GGPTase-I activity was determined by the method of Casey et al, *Proc. Natl. Acad. Sci. USA,* 1991, 88, 8631-8635. This method measures the transfer of isoprenoid from $^3$H-geranylgeranyl diphosphate (GGPP) into a Ras protein with a C-terminal leucine-for-serine substitution (designated as Ras-CVLL).

Example 16

This example illustrates GGPTase I and FPTase inhibitory activities of some of the compounds of the present invention.

Assays for the inhibition studies of GGPTase I were performed in a manner analogous to that described by Casey, et al., *Proc. Natl. Acad Sci. USA,* 1991, 88, 8631-8635, with the following modifications. For those assays, the reaction mixtures contained the following components in 50 µl:0.25 µM [$^3$H]GGPP (sp. act. 8-10 Ci/mmol), 2.5 µM Ras-CVLL, 50 mM Tris-Cl, pH 7.7, 20 mM KCl, 5 mM MgCl$_2$, 5 µM ZnCl$_2$, 1 mM DTT, 0.5 mM Zwittergent 3-14 and the desired amount of the compound to be tested for inhibitory potential. After pre-equilibrating the assay mixture at 30° C. in the absence of the enzyme, the reaction was initiated by addition of the enzyme (75 ng). Following an about 10 minute incubation at about 30° C., the reactions were terminated by addition of about 0.5 ml of about 4% SDS. About 40 mg of bovine brain membranes was added to the samples to enhance recovery during precipitation. Product was precipitated by addition of about 0.5 ml of 30% TCA, allowed to stand at room temperature for about 15 minutes, and processed by filtration through glass-fiber filters as described previously (Reiss et al., *Methods: Companion to Methods in Enzymology,* 1991, 1, 241-245). Reactions were never allowed to proceed to more than 10% completion based on the limiting substrate. Assays for the inhibition studies of FPTase were performed analogous the GGPTase I inhibition studies, except [$^3$H]GGPP was replaced with 0.25 µM of [$^3$H]FPP (sp. act. 8-10 ci/mmol) and Ras-CVLL, was replaced with 1 µM H-Ras.

Using the method described above, the GGPTase I inhibitory activities of some of the compounds of the present invention were evaluated. Compounds of Table 1 were found to have inhibitory activity. Mixtures of regioisomers and/or enantiomers are used unless indicated otherwise (for example, the position of substituents on a cyclic or heterocyclic moiety within the backbone of the compounds of the present invention).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the formula:

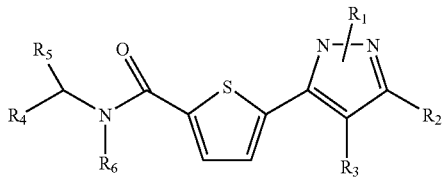

or a pharmaceutically-acceptable salt thereof,
wherein
$R_1$ is phenyl, benzyl, methyl, ethyl, propyl, 3,4-dimethylphenyl, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, ethanol, or 3,4-methylenedioxyphenyl;

$R_2$ is pyridine;

$R_3$ is H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is H, $NH_2$, $CON(CH_3)_2$, $CO_2H$, $CN$, $CH_2OH$, $CONH_2$, $CSNH_2$, $CONHOH$, $C(NH)NH_2$, $CONHNH_2$, $CONHCH_3$, $CH_2OCH_3$, $CONH$-cyclohexyl, $CO_2CH_3$, or

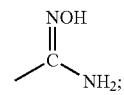

$R_5$ is isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-cyclohexane, 4-chlorobenzyl, phenyl, 2-hydroxybenzyl, 4-tertbutoxybenzyl, 4-aminobenzyl, $CH_2OH$, $(CH_2)_3NHC(NH)NH_2$ or $CH_2CH(CH_3)_2$; and, $R_6$ is H, methyl, ethyl, propyl, isopropyl, $CH_2CO_2H$, $CH_2CO_2Et$, benzyl, or $CH_2$-(2-methoxynaphthyl); or, $R_5$ and $R_6$ together form:

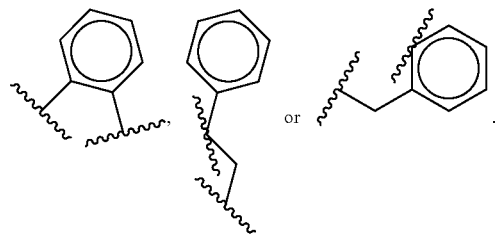

2. A pharmaceutical composition comprising a compound of claim 1 or a pharmaceutically-acceptable salt thereof, and a pharmaceutically- acceptable carrier.

* * * * *